US010851152B2

(12) United States Patent
Koide et al.

(10) Patent No.: US 10,851,152 B2
(45) Date of Patent: Dec. 1, 2020

(54) POLYMERIZED PEPTIDE AND GEL HAVING COLLAGEN-LIKE STRUCTURE

(71) Applicants: WASEDA UNIVERSITY, Tokyo (JP); KOLA-GEN PHARMA INC., Kyoto (JP)

(72) Inventors: Takaki Koide, Tokyo (JP); Shinichiro Ichise, Tokyo (JP); Shungo Takeuchi, Tokyo (JP); Hiroshi Nose, Kyoto (JP)

(73) Assignee: KOLA-GEN PHARMA, INC., Kyoto (JP)

( * ) Notice: Subject to any disclaimer, the term of this patent is extended or adjusted under 35 U.S.C. 154(b) by 271 days.

(21) Appl. No.: 15/579,286

(22) PCT Filed: Jun. 23, 2016

(86) PCT No.: PCT/JP2016/068667
§ 371 (c)(1),
(2) Date: Dec. 4, 2017

(87) PCT Pub. No.: WO2016/208673
PCT Pub. Date: Dec. 29, 2016

(65) Prior Publication Data
US 2018/0319867 A1 Nov. 8, 2018

(30) Foreign Application Priority Data

Jun. 25, 2015 (JP) .................................. 2015-127450

(51) Int. Cl.
| | |
|---|---|
| *C07K 14/78* | (2006.01) |
| *C12M 3/00* | (2006.01) |
| *A61L 15/00* | (2006.01) |
| *A61K 38/00* | (2006.01) |
| *C07K 1/02* | (2006.01) |
| *C07K 14/00* | (2006.01) |
| *C08J 3/075* | (2006.01) |
| *A61L 15/32* | (2006.01) |
| *C12N 5/00* | (2006.01) |

(52) U.S. Cl.
CPC .............. *C07K 14/78* (2013.01); *A61K 38/00* (2013.01); *A61L 15/00* (2013.01); *C07K 1/02* (2013.01); *C07K 14/00* (2013.01); *C08J 3/075* (2013.01); *C12M 3/00* (2013.01); *A61L 15/325* (2013.01); *C12N 5/0018* (2013.01)

(58) Field of Classification Search
CPC ....... A61K 38/00; A61L 15/00; A61L 15/325; C07K 14/00; C07K 14/78; C07K 1/02; C08J 3/075; C12M 3/00; C12N 5/0018
See application file for complete search history.

(56) References Cited

U.S. PATENT DOCUMENTS

| | | | |
|---|---|---|---|
| 4,407,767 | A | 10/1983 | Seaborn |
| 5,412,076 | A | 5/1995 | Gagnieu |
| 5,763,579 | A | 6/1998 | Gagnieu et al. |
| 6,992,172 | B1 | 1/2006 | Chang et al. |
| 2013/0084638 | A1 | 4/2013 | Iwazawa et al. |

FOREIGN PATENT DOCUMENTS

| | | |
|---|---|---|
| EP | 1014176 | 6/2000 |
| JP | 2005263784 | 9/2005 |
| WO | 2004085473 | 10/2004 |
| WO | 2008103041 | 8/2008 |
| WO | 2015031950 A1 | 3/2015 |

OTHER PUBLICATIONS

Supplementary European Search Report mailed in EP 16814442 dated Dec. 10, 2018.
Barth, Dirk, The Role of Cystine Knots in Collagen Folding and Stability, Part II. Conformational Properties of (Pro-Hyp-Gly)n Model Trimers with N- and C-Terminal Collagen Type III Cystine Knots, Chem. Eur. J. , 2003, vol. 9, pp. 3703-3714.
Boudko, Sergei, Nucleation and Propagation of the Collagen Triple Helix in Single-chain and Trimerized Peptides: Transition from Third to First Order Kinetics, J. Mol. Biol. , 2002, vol. 317, pp. 459-470.
Wegener, Henrik, The cysteine rich region of type VII collagen is a cystine knot with a new topology, J. Biol. Chem., 2014, vol. 289, No. 8, pp. 4861-4869.
International Search Report dated Dec. 29, 2016 in PCT/JP2016/068667.
Koide: "Designed triple-helical peptides as tools for collagen biochemistry and matrix engineering" PhiL. Trans. R. Soc. 3 (2007) 362,1281-1291.
Sakakibara et al.: "Synthesis of (Pro-Hyp-Gly)n of defined molecular weights Evidence for the stabilization of collagen triple helix by hydroxypyroline", Biochimica et Biophysica Acta, 303 (1973) 198-202.

*Primary Examiner* — Marcela M Cordero Garcia
(74) *Attorney, Agent, or Firm* — Fox Rothschild, LLP; Amy A. Dobbelaere

(57) ABSTRACT

The present invention is produced as a polymerized peptide prepared by oxidatively cross-linking collagen-like peptides having the triple-helical structure containing three peptide chains each containing multiple cysteine (Cys) residues. This polymerized peptide can be processed into a hydrogel and a thin membrane sheet before use, and is capable of imparting a particular physiological function such as cellular adhesion by incorporating functional amino acid sequences present on biological polymers. Further, the present invention provides a method for producing the abovementioned polymerized peptide and the like; and use applications employing the same, such as cell culturing, wound dressing, and compositions including regenerative medical materials and research materials.

11 Claims, 24 Drawing Sheets
Specification includes a Sequence Listing.

CCCC2

CCC2

CC2

YCC2

(n=5, mean±S.D., ;p<0.01, *; p<0.001)

Collagen I  CCC2-GPOGPR(short)  CCC2-GPOGPR(short)
(Ligand-free)

SEQUENCE LISTING

```
<160> NUMBER OF SEQ ID NOS: 41

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence: Synthetic
      YCC2 polypeptide
<220> FEATURE:
<221> NAME/KEY: MOD_RES
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
```

```
<221> NAME/KEY: MOD_RES
<222> LOCATION: (20)..(20)
<223> OTHER INFORMATION: 4-Hydroxyproline
<220> FEATURE:
<221> NAME/KEY: MOD_RES
<222> LOCATION: (26)..(26)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline
<220> FEATURE:
<221> NAME/KEY: MOD_RES
<222> LOCATION: (35)..(35)
<223> OTHER INFORMATION: 4-Hydroxyproline
<220> FEATURE:
<221> NAME/KEY: MOD_RES
<222> LOCATION: (38)..(38)
<223> OTHER INFORMATION: 4-Hydroxyproline

<400> SEQUENCE: 1

Tyr Cys Cys Pro Pro Gly Pro Pro Gly Pro Pro Gly Pro Pro Gly Pro
1               5                   10                  15
Pro Gly Pro Pro Gly Pro Arg Gly Pro Pro Gly Pro Pro Gly Pro Pro
            20                  25                  30
Gly Pro Pro Gly Pro Pro Gly Cys Cys Tyr
        35                  40

<210> SEQ ID NO 2
<211> LENGTH: 40
<212> TYPE: PRT
<213> ORGANISM: Artificial Sequence
<220> FEATURE:
<223> OTHER INFORMATION: Description of Artificial Sequence: Synthetic
      CC2 polypeptide
<220> FEATURE:
<221> NAME/KEY: MOD_RES
<222> LOCATION: (4)..(4)
<223> OTHER INFORMATION: 4-Hydroxyproline
<220> FEATURE:
<221> NAME/KEY: MOD_RES
<222> LOCATION: (7)..(7)
<223> OTHER INFORMATION: 4-Hydroxyproline
<220> FEATURE:
<221> NAME/KEY: MOD_RES
<222> LOCATION: (10)..(10)
<223> OTHER INFORMATION: 4-Hydroxyproline
<220> FEATURE:
<221> NAME/KEY: MOD_RES
<222> LOCATION: (13)..(13)
<223> OTHER INFORMATION: 4-Hydroxyproline
<220> FEATURE:
<221> NAME/KEY: MOD_RES
<222> LOCATION: (16)..(16)
<223> OTHER INFORMATION: 4-Hydroxyproline
<220> FEATURE:
<221> NAME/KEY: MOD_RES
<222> LOCATION: (19)..(19)
<223> OTHER INFORMATION: 4-Hydroxyproline
<220> FEATURE:
<221> NAME/KEY: MOD_RES
<222> LOCATION: (25)..(25)
<223> OTHER INFORMATION: 4-Hydroxyproline
<220> FEATURE:
<221> NAME/KEY: MOD_RES
<222> LOCATION: (28)..(28)
<223> OTHER INFORMATION: 4-Hydroxyproline
<220> FEATURE:
<221> NAME/KEY: MOD_RES
<222> LOCATION: (31)..(31)
<223> OTHER INFORMATION: 4-Hydroxyproline
```

```
<220> FEATURE:
<221> NAME/KEY: MOD_RES
<222> LOCATION: (34)..(34)
<223> OTHER INFORMATION: 4-Hydroxyproline
<220> FEATURE:
<221> NAME/KEY: MOD_RES
<222> LOCATION: (37)..(37)
<223> OTHER INFORMATION: 4-Hydroxyproline

<400> SEQUENCE: 2

Cys Cys Pro Pro Gly Pro Pro Gly Pro Pro Gly Pro Pro Gly Pro Pro
1               5                   10                  15

Gly Pro Pro Gly Pro Arg Gly Pro Pro Gly Pro Pro Gly Pro Pro Gly
            20                  25                  30

Pro Pro Gly Pro Pro Gly Cys Cys
            35                  40

<210> SEQ ID NO 3
<211> LENGTH: 38
<212> TYPE: PRT
<213> ORGANISM: Artificial Sequence
<220> FEATURE:
<223> OTHER INFORMATION: Description of Artificial Sequence: Synthetic
      CC1 polypeptide
<220> FEATURE:
<221> NAME/KEY: MOD_RES
<222> LOCATION: (2)..(2)
<223> OTHER INFORMATION: 4-Hydroxyproline
<220> FEATURE:
<221> NAME/KEY: MOD_RES
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
<221> NAME/KEY: MOD_RES
<222> LOCATION: (23)..(23)
<223> OTHER INFORMATION: 4-Hydroxyproline
<220> FEATURE:
<221> NAME/KEY: MOD_RES
<222> LOCATION: (26)..(26)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline
<220> FEATURE:
<221> NAME/KEY: MOD_RES
<222> LOCATION: (35)..(35)
<223> OTHER INFORMATION: 4-Hydroxyproline

<400> SEQUENCE: 3

Pro Pro Gly Pro Pro Gly Pro Pro Gly Pro Pro Gly Pro Pro Gly Pro
1               5                   10                  15

Pro Gly Pro Arg Gly Pro Pro Gly Pro Pro Gly Pro Pro Gly Pro Pro
```

Gly Pro Pro Gly Cys Cys
          35

<210> SEQ ID NO 4
<211> LENGTH: 38
<212> TYPE: PRT
<213> ORGANISM: Artificial Sequence
<220> FEATURE:
<223> OTHER INFORMATION: Description of Artificial Sequence: Synthetic
      C2 polypeptide
<220> FEATURE:
<221> NAME/KEY: MOD_RES
<222> LOCATION: (3)..(3)
<223> OTHER INFORMATION: 4-Hydroxyproline
<220> FEATURE:
<221> NAME/KEY: MOD_RES
<222> LOCATION: (6)..(6)
<223> OTHER INFORMATION: 4-Hydroxyproline
<220> FEATURE:
<221> NAME/KEY: MOD_RES
<222> LOCATION: (9)..(9)
<223> OTHER INFORMATION: 4-Hydroxyproline
<220> FEATURE:
<221> NAME/KEY: MOD_RES
<222> LOCATION: (12)..(12)
<223> OTHER INFORMATION: 4-Hydroxyproline
<220> FEATURE:
<221> NAME/KEY: MOD_RES
<222> LOCATION: (15)..(15)
<223> OTHER INFORMATION: 4-Hydroxyproline
<220> FEATURE:
<221> NAME/KEY: MOD_RES
<222> LOCATION: (18)..(18)
<223> OTHER INFORMATION: 4-Hydroxyproline
<220> FEATURE:
<221> NAME/KEY: MOD_RES
<222> LOCATION: (24)..(24)
<223> OTHER INFORMATION: 4-Hydroxyproline
<220> FEATURE:
<221> NAME/KEY: MOD_RES
<222> LOCATION: (27)..(27)
<223> OTHER INFORMATION: 4-Hydroxyproline
<220> FEATURE:
<221> NAME/KEY: MOD_RES
<222> LOCATION: (30)..(30)
<223> OTHER INFORMATION: 4-Hydroxyproline
<220> FEATURE:
<221> NAME/KEY: MOD_RES
<222> LOCATION: (33)..(33)
<223> OTHER INFORMATION: 4-Hydroxyproline
<220> FEATURE:
<221> NAME/KEY: MOD_RES
<222> LOCATION: (36)..(36)
<223> OTHER INFORMATION: 4-Hydroxyproline

<400> SEQUENCE: 4

Cys Pro Pro Gly Pro Pro Gly Pro Pro Gly Pro Pro Gly Pro Pro Gly
1               5                   10                  15

Pro Pro Gly Pro Arg Gly Pro Pro Gly Pro Pro Gly Pro Pro Gly Pro
            20                  25                  30

Pro Gly Pro Pro Gly Cys
        35

<210> SEQ ID NO 5
<211> LENGTH: 42
<212> TYPE: PRT
<213> ORGANISM: Artificial Sequence
<220> FEATURE:
<223> OTHER INFORMATION: Description of Artificial Sequence: Synthetic
      CCC2 polypeptide
<220> FEATURE:
<221> NAME/KEY: MOD_RES

```
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
<221> NAME/KEY: MOD_RES
<222> LOCATION: (20)..(20)
<223> OTHER INFORMATION: 4-Hydroxyproline
<220> FEATURE:
<221> NAME/KEY: MOD_RES
<222> LOCATION: (26)..(26)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline
<220> FEATURE:
<221> NAME/KEY: MOD_RES
<222> LOCATION: (35)..(35)
<223> OTHER INFORMATION: 4-Hydroxyproline
<220> FEATURE:
<221> NAME/KEY: MOD_RES
<222> LOCATION: (38)..(38)
<223> OTHER INFORMATION: 4-Hydroxyproline

<400> SEQUENCE: 5

Cys Cys Cys Pro Pro Gly Pro Pro Gly Pro Pro Gly Pro Pro Gly Pro
1               5                   10                  15
Pro Gly Pro Pro Gly Pro Arg Gly Pro Pro Gly Pro Pro Gly Pro Pro
            20                  25                  30
Gly Pro Pro Gly Pro Pro Gly Cys Cys Cys
        35                  40

<210> SEQ ID NO 6
<211> LENGTH: 48
<212> TYPE: PRT
<213> ORGANISM: Artificial Sequence
<220> FEATURE:
<223> OTHER INFORMATION: Description of Artificial Sequence: Synthetic
      GGGCCC polypeptide
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
```

```
<221> NAME/KEY: MOD_RES
<222> LOCATION: (20)..(20)
<223> OTHER INFORMATION: 4-Hydroxyproline
<220> FEATURE:
<221> NAME/KEY: MOD_RES
<222> LOCATION: (23)..(23)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline
<220> FEATURE:
<221> NAME/KEY: MOD_RES
<222> LOCATION: (35)..(35)
<223> OTHER INFORMATION: 4-Hydroxyproline
<220> FEATURE:
<221> NAME/KEY: MOD_RES
<222> LOCATION: (38)..(38)
<223> OTHER INFORMATION: 4-Hydroxyproline
<220> FEATURE:
<221> NAME/KEY: MOD_RES
<222> LOCATION: (41)..(41)
<223> OTHER INFORMATION: 4-Hydroxyproline

<400> SEQUENCE: 6

Cys Cys Cys Gly Gly Gly Pro Pro Gly Pro Pro Gly Pro Pro Gly Pro
1               5                   10                  15

Pro Gly Pro Pro Gly Phe Pro Gly Glu Arg Gly Pro Pro Gly Pro Pro
            20                  25                  30

Gly Pro Pro Gly Pro Pro Gly Pro Pro Gly Gly Gly Cys Cys Cys
        35                  40                  45

<210> SEQ ID NO 7
<211> LENGTH: 44
<212> TYPE: PRT
<213> ORGANISM: Artificial Sequence
<220> FEATURE:
<223> OTHER INFORMATION: Description of Artificial Sequence: Synthetic
      CCCC2 polypeptide
<220> FEATURE:
<221> NAME/KEY: MOD_RES
<222> LOCATION: (6)..(6)
<223> OTHER INFORMATION: 4-Hydroxyproline
<220> FEATURE:
<221> NAME/KEY: MOD_RES
<222> LOCATION: (9)..(9)
<223> OTHER INFORMATION: 4-Hydroxyproline
<220> FEATURE:
<221> NAME/KEY: MOD_RES
<222> LOCATION: (12)..(12)
<223> OTHER INFORMATION: 4-Hydroxyproline
<220> FEATURE:
<221> NAME/KEY: MOD_RES
<222> LOCATION: (15)..(15)
<223> OTHER INFORMATION: 4-Hydroxyproline
<220> FEATURE:
<221> NAME/KEY: MOD_RES
<222> LOCATION: (18)..(18)
<223> OTHER INFORMATION: 4-Hydroxyproline
<220> FEATURE:
<221> NAME/KEY: MOD_RES
<222> LOCATION: (21)..(21)
<223> OTHER INFORMATION: 4-Hydroxyproline
<220> FEATURE:
<221> NAME/KEY: MOD_RES
<222> LOCATION: (27)..(27)
<223> OTHER INFORMATION: 4-Hydroxyproline
<220> FEATURE:
<221> NAME/KEY: MOD_RES
<222> LOCATION: (30)..(30)
<223> OTHER INFORMATION: 4-Hydroxyproline
```

```
<220> FEATURE:
<221> NAME/KEY: MOD_RES
<222> LOCATION: (33)..(33)
<223> OTHER INFORMATION: 4-Hydroxyproline
<220> FEATURE:
<221> NAME/KEY: MOD_RES
<222> LOCATION: (36)..(36)
<223> OTHER INFORMATION: 4-Hydroxyproline
<220> FEATURE:
<221> NAME/KEY: MOD_RES
<222> LOCATION: (39)..(39)
<223> OTHER INFORMATION: 4-Hydroxyproline

<400> SEQUENCE: 7

Cys Cys Cys Cys Pro Pro Gly Pro Pro Gly Pro Pro Gly Pro Pro Gly
1               5                   10                  15

Pro Pro Gly Pro Pro Gly Pro Arg Gly Pro Pro Gly Pro Pro Gly Pro
                20                  25                  30

Pro Gly Pro Pro Gly Pro Pro Gly Cys Cys Cys Cys
            35                  40

<210> SEQ ID NO 8
<211> LENGTH: 38
<212> TYPE: PRT
<213> ORGANISM: Artificial Sequence
<220> FEATURE:
<223> OTHER INFORMATION: Description of Artificial Sequence: Synthetic
      Y2 polypeptide
<220> FEATURE:
<221> NAME/KEY: MOD_RES
<222> LOCATION: (3)..(3)
<223> OTHER INFORMATION: 4-Hydroxyproline
<220> FEATURE:
<221> NAME/KEY: MOD_RES
<222> LOCATION: (6)..(6)
<223> OTHER INFORMATION: 4-Hydroxyproline
<220> FEATURE:
<221> NAME/KEY: MOD_RES
<222> LOCATION: (9)..(9)
<223> OTHER INFORMATION: 4-Hydroxyproline
<220> FEATURE:
<221> NAME/KEY: MOD_RES
<222> LOCATION: (12)..(12)
<223> OTHER INFORMATION: 4-Hydroxyproline
<220> FEATURE:
<221> NAME/KEY: MOD_RES
<222> LOCATION: (15)..(15)
<223> OTHER INFORMATION: 4-Hydroxyproline
<220> FEATURE:
<221> NAME/KEY: MOD_RES
<222> LOCATION: (18)..(18)
<223> OTHER INFORMATION: 4-Hydroxyproline
<220> FEATURE:
<221> NAME/KEY: MOD_RES
<222> LOCATION: (24)..(24)
<223> OTHER INFORMATION: 4-Hydroxyproline
<220> FEATURE:
<221> NAME/KEY: MOD_RES
<222> LOCATION: (27)..(27)
<223> OTHER INFORMATION: 4-Hydroxyproline
<220> FEATURE:
<221> NAME/KEY: MOD_RES
<222> LOCATION: (30)..(30)
<223> OTHER INFORMATION: 4-Hydroxyproline
<220> FEATURE:
<221> NAME/KEY: MOD_RES
<222> LOCATION: (33)..(33)
<223> OTHER INFORMATION: 4-Hydroxyproline
<220> FEATURE:
<221> NAME/KEY: MOD_RES
<222> LOCATION: (36)..(36)
<223> OTHER INFORMATION: 4-Hydroxyproline

<400> SEQUENCE: 8
```

```
Tyr Pro Pro Gly Pro Gly Pro Pro Gly Pro Gly Pro Pro Gly
1               5                   10                  15

Pro Pro Gly Pro Arg Gly Pro Pro Gly Pro Pro Gly Pro Pro Gly Pro
            20                  25                  30

Pro Gly Pro Pro Gly Tyr
        35
```

<210> SEQ ID NO 9
<211> LENGTH: 38
<212> TYPE: PRT
<213> ORGANISM: Artificial Sequence
<220> FEATURE:
<223> OTHER INFORMATION: Description of Artificial Sequence: Synthetic
      YCC2-Scr polypeptide
<220> FEATURE:
<221> NAME/KEY: MOD_RES
<222> LOCATION: (7)..(7)
<223> OTHER INFORMATION: 4-Hydroxyproline
<220> FEATURE:
<221> NAME/KEY: MOD_RES
<222> LOCATION: (10)..(10)
<223> OTHER INFORMATION: 4-Hydroxyproline
<220> FEATURE:
<221> NAME/KEY: MOD_RES
<222> LOCATION: (12)..(12)
<223> OTHER INFORMATION: 4-Hydroxyproline
<220> FEATURE:
<221> NAME/KEY: MOD_RES
<222> LOCATION: (16)..(16)
<223> OTHER INFORMATION: 4-Hydroxyproline
<220> FEATURE:
<221> NAME/KEY: MOD_RES
<222> LOCATION: (19)..(19)
<223> OTHER INFORMATION: 4-Hydroxyproline
<220> FEATURE:
<221> NAME/KEY: MOD_RES
<222> LOCATION: (21)..(21)
<223> OTHER INFORMATION: 4-Hydroxyproline
<220> FEATURE:
<221> NAME/KEY: MOD_RES
<222> LOCATION: (25)..(25)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline
<220> FEATURE:
<221> NAME/KEY: MOD_RES
<222> LOCATION: (34)..(34)
<223> OTHER INFORMATION: 4-Hydroxyproline

<400> SEQUENCE: 9

```
Tyr Cys Cys Gly Pro Pro Pro Gly Pro Pro Gly Pro Pro
1               5                   10              15

Gly Gly Pro Pro Pro Gly Arg Pro Pro Gly Pro Pro Gly Gly Pro
                20                  25                  30

Pro Pro Gly Cys Cys Tyr
        35
```

<210> SEQ ID NO 10
<211> LENGTH: 36
<212> TYPE: PRT
<213> ORGANISM: Artificial Sequence
<220> FEATURE:
<223> OTHER INFORMATION: Description of Artificial Sequence: Synthetic
      CCC2-GPOGPR (short) polypeptide
<220> FEATURE:
<221> NAME/KEY: MOD_RES

```
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
<221> NAME/KEY: MOD_RES
<222> LOCATION: (23)..(23)
<223> OTHER INFORMATION: 4-Hydroxyproline
<220> FEATURE:
<221> NAME/KEY: MOD_RES
<222> LOCATION: (26)..(26)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline

<400> SEQUENCE: 10

Cys Cys Cys Pro Pro Gly Pro Pro Gly Pro Pro Gly Pro Pro Gly Pro
1               5                   10                  15

Pro Gly Pro Arg Gly Pro Pro Gly Pro Pro Gly Pro Pro Gly Pro Pro
            20                  25                  30

Gly Cys Cys Cys
        35

<210> SEQ ID NO 11
<211> LENGTH: 36
<212> TYPE: PRT
<213> ORGANISM: Artificial Sequence
<220> FEATURE:
<223> OTHER INFORMATION: Description of Artificial Sequence: Synthetic
      CCC2-GFOGER (short) polypeptide
<220> FEATURE:
<221> NAME/KEY: MOD_RES
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
<221> NAME/KEY: MOD_RES
<222> LOCATION: (23)..(23)
<223> OTHER INFORMATION: 4-Hydroxyproline
<220> FEATURE:
```

<221> NAME/KEY: MOD_RES
<222> LOCATION: (26)..(26)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline

<400> SEQUENCE: 11

Cys Cys Cys Pro Pro Gly Pro Pro Gly Pro Pro Gly Pro Pro Gly Phe
1               5                   10                  15

Pro Gly Glu Arg Gly Pro Pro Gly Pro Pro Gly Pro Pro Gly Pro Pro
            20                  25                  30

Gly Cys Cys Cys
        35

<210> SEQ ID NO 12
<211> LENGTH: 42
<212> TYPE: PRT
<213> ORGANISM: Artificial Sequence
<220> FEATURE:
<223> OTHER INFORMATION: Description of Artificial Sequence: Synthetic
      YCC2-GFOGER polypeptide
<220> FEATURE:
<221> NAME/KEY: MOD_RES
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
<221> NAME/KEY: MOD_RES
<222> LOCATION: (20)..(20)
<223> OTHER INFORMATION: 4-Hydroxyproline
<220> FEATURE:
<221> NAME/KEY: MOD_RES
<222> LOCATION: (26)..(26)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline
<220> FEATURE:
<221> NAME/KEY: MOD_RES
<222> LOCATION: (35)..(35)
<223> OTHER INFORMATION: 4-Hydroxyproline
<220> FEATURE:
<221> NAME/KEY: MOD_RES
<222> LOCATION: (38)..(38)
<223> OTHER INFORMATION: 4-Hydroxyproline

<400> SEQUENCE: 12

Tyr Cys Cys Pro Pro Gly Pro Pro Gly Pro Pro Gly Pro Pro Gly Pro

```
                1               5                   10                  15
            Pro Gly Phe Pro Gly Glu Arg Gly Pro Pro Gly Pro Pro
                            20                  25                  30
            Gly Pro Pro Gly Pro Pro Gly Cys Cys Tyr
                            35                  40
```

<210> SEQ ID NO 13
<211> LENGTH: 48
<212> TYPE: PRT
<213> ORGANISM: Artificial Sequence
<220> FEATURE:
<223> OTHER INFORMATION: Description of Artificial Sequence: Synthetic
      YCC2-GVMGFO polypeptide
<220> FEATURE:
<221> NAME/KEY: MOD_RES
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
<221> NAME/KEY: MOD_RES
<222> LOCATION: (23)..(23)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline
<220> FEATURE:
<221> NAME/KEY: MOD_RES
<222> LOCATION: (35)..(35)
<223> OTHER INFORMATION: 4-Hydroxyproline
<220> FEATURE:
<221> NAME/KEY: MOD_RES
<222> LOCATION: (38)..(38)
<223> OTHER INFORMATION: 4-Hydroxyproline
<220> FEATURE:
<221> NAME/KEY: MOD_RES
<222> LOCATION: (41)..(41)
<223> OTHER INFORMATION: 4-Hydroxyproline
<220> FEATURE:
<221> NAME/KEY: MOD_RES
<222> LOCATION: (44)..(44)
<223> OTHER INFORMATION: 4-Hydroxyproline

<400> SEQUENCE: 13

```
            Tyr Cys Cys Pro Pro Gly Pro Pro Gly Pro Pro Gly Pro Pro Gly Pro
            1               5                   10                  15
            Pro Gly Pro Arg Gly Gln Pro Gly Val Met Gly Phe Pro Gly Pro Pro
                            20                  25                  30
            Gly Pro Pro Gly Pro Pro Gly Pro Pro Gly Pro Pro Gly Cys Cys Tyr
                            35                  40                  45
```

<210> SEQ ID NO 14
<211> LENGTH: 57

```
<212> TYPE: PRT
<213> ORGANISM: Artificial Sequence
<220> FEATURE:
<223> OTHER INFORMATION: Description of Artificial Sequence: Synthetic
      YCC2-KGHRGF polypeptide
<220> FEATURE:
<221> NAME/KEY: MOD_RES
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
<221> NAME/KEY: MOD_RES
<222> LOCATION: (20)..(20)
<223> OTHER INFORMATION: 4-Hydroxyproline
<220> FEATURE:
<221> NAME/KEY: MOD_RES
<222> LOCATION: (23)..(23)
<223> OTHER INFORMATION: 4-Hydroxyproline
<220> FEATURE:
<221> NAME/KEY: MOD_RES
<222> LOCATION: (35)..(35)
<223> OTHER INFORMATION: 4-Hydroxyproline
<220> FEATURE:
<221> NAME/KEY: MOD_RES
<222> LOCATION: (38)..(38)
<223> OTHER INFORMATION: 4-Hydroxyproline
<220> FEATURE:
<221> NAME/KEY: MOD_RES
<222> LOCATION: (41)..(41)
<223> OTHER INFORMATION: 4-Hydroxyproline
<220> FEATURE:
<221> NAME/KEY: MOD_RES
<222> LOCATION: (44)..(44)
<223> OTHER INFORMATION: 4-Hydroxyproline
<220> FEATURE:
<221> NAME/KEY: MOD_RES
<222> LOCATION: (47)..(47)
<223> OTHER INFORMATION: 4-Hydroxyproline
<220> FEATURE:
<221> NAME/KEY: MOD_RES
<222> LOCATION: (50)..(50)
<223> OTHER INFORMATION: 4-Hydroxyproline
<220> FEATURE:
<221> NAME/KEY: MOD_RES
<222> LOCATION: (53)..(53)
<223> OTHER INFORMATION: 4-Hydroxyproline

<400> SEQUENCE: 14

Tyr Cys Cys Pro Pro Gly Pro Pro Gly Pro Pro Gly Pro Pro Gly Pro
1               5                   10                  15

Pro Gly Pro Pro Gly Pro Pro Gly Pro Lys Gly His Arg Gly Phe Ser
            20                  25                  30

Gly Leu Pro Gly Pro Pro Gly Pro Pro Gly Pro Pro Gly Pro Pro Gly
        35                  40                  45

Pro Pro Gly Pro Pro Gly Cys Cys Tyr
    50                  55

<210> SEQ ID NO 15
<211> LENGTH: 48
```

```
<212> TYPE: PRT
<213> ORGANISM: Artificial Sequence
<220> FEATURE:
<223> OTHER INFORMATION: Description of Artificial Sequence: Synthetic
      CCC2-GPOGPR polypeptide
<220> FEATURE:
<221> NAME/KEY: MOD_RES
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
<221> NAME/KEY: MOD_RES
<222> LOCATION: (20)..(20)
<223> OTHER INFORMATION: 4-Hydroxyproline
<220> FEATURE:
<221> NAME/KEY: MOD_RES
<222> LOCATION: (23)..(23)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline
<220> FEATURE:
<221> NAME/KEY: MOD_RES
<222> LOCATION: (35)..(35)
<223> OTHER INFORMATION: 4-Hydroxyproline
<220> FEATURE:
<221> NAME/KEY: MOD_RES
<222> LOCATION: (38)..(38)
<223> OTHER INFORMATION: 4-Hydroxyproline
<220> FEATURE:
<221> NAME/KEY: MOD_RES
<222> LOCATION: (41)..(41)
<223> OTHER INFORMATION: 4-Hydroxyproline
<220> FEATURE:
<221> NAME/KEY: MOD_RES
<222> LOCATION: (44)..(44)
<223> OTHER INFORMATION: 4-Hydroxyproline

<400> SEQUENCE: 15

Cys Cys Cys Pro Pro Gly Pro Pro Gly Pro Pro Gly Pro Pro Gly Pro
1               5                   10                  15

Pro Gly Pro Pro Gly Pro Pro Gly Pro Arg Gly Pro Pro Gly Pro Pro
                20                  25                  30

Gly Pro Pro Gly Pro Pro Gly Pro Pro Gly Pro Pro Gly Cys Cys Cys
                35                  40                  45

<210> SEQ ID NO 16
<211> LENGTH: 48
<212> TYPE: PRT
<213> ORGANISM: Artificial Sequence
<220> FEATURE:
<223> OTHER INFORMATION: Description of Artificial Sequence: Synthetic
      CCC2-GFOGER polypeptide
<220> FEATURE:
<221> NAME/KEY: MOD_RES
```

```
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
<221> NAME/KEY: MOD_RES
<222> LOCATION: (20)..(20)
<223> OTHER INFORMATION: 4-Hydroxyproline
<220> FEATURE:
<221> NAME/KEY: MOD_RES
<222> LOCATION: (23)..(23)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline
<220> FEATURE:
<221> NAME/KEY: MOD_RES
<222> LOCATION: (35)..(35)
<223> OTHER INFORMATION: 4-Hydroxyproline
<220> FEATURE:
<221> NAME/KEY: MOD_RES
<222> LOCATION: (38)..(38)
<223> OTHER INFORMATION: 4-Hydroxyproline
<220> FEATURE:
<221> NAME/KEY: MOD_RES
<222> LOCATION: (41)..(41)
<223> OTHER INFORMATION: 4-Hydroxyproline
<220> FEATURE:
<221> NAME/KEY: MOD_RES
<222> LOCATION: (44)..(44)
<223> OTHER INFORMATION: 4-Hydroxyproline

<400> SEQUENCE: 16

Cys Cys Cys Pro Pro Gly Pro Pro Gly Pro Pro Gly Pro Pro Gly Pro
1               5                   10                  15

Pro Gly Pro Pro Gly Phe Pro Gly Glu Arg Gly Pro Pro Gly Pro Pro
            20                  25                  30

Gly Pro Pro Gly Pro Pro Gly Pro Pro Gly Pro Pro Gly Cys Cys Cys
        35                  40                  45

<210> SEQ ID NO 17
<211> LENGTH: 48
<212> TYPE: PRT
<213> ORGANISM: Artificial Sequence
<220> FEATURE:
<223> OTHER INFORMATION: Description of Artificial Sequence: Synthetic
      CCC2-GVMGFO polypeptide
<220> FEATURE:
<221> NAME/KEY: MOD_RES
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
```

```
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
<220> FEATURE:
<221> NAME/KEY: MOD_RES
<222> LOCATION: (23)..(23)
<223> OTHER INFORMATION: 4-Hydroxyproline
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline
<220> FEATURE:
<221> NAME/KEY: MOD_RES
<222> LOCATION: (35)..(35)
<223> OTHER INFORMATION: 4-Hydroxyproline
<220> FEATURE:
<221> NAME/KEY: MOD_RES
<222> LOCATION: (38)..(38)
<223> OTHER INFORMATION: 4-Hydroxyproline
<220> FEATURE:
<221> NAME/KEY: MOD_RES
<222> LOCATION: (41)..(41)
<223> OTHER INFORMATION: 4-Hydroxyproline
<220> FEATURE:
<221> NAME/KEY: MOD_RES
<222> LOCATION: (44)..(44)
<223> OTHER INFORMATION: 4-Hydroxyproline

<400> SEQUENCE: 17

Cys Cys Cys Pro Pro Gly Pro Pro Gly Pro Pro Gly Pro Pro Gly Pro
1               5                   10                  15

Pro Gly Pro Arg Gly Gln Pro Gly Val Met Gly Phe Pro Gly Pro Pro
            20                  25                  30

Gly Pro Pro Gly Pro Pro Gly Pro Pro Gly Pro Pro Gly Cys Cys Cys
        35                  40                  45

<210> SEQ ID NO 18
<211> LENGTH: 48
<212> TYPE: PRT
<213> ORGANISM: Artificial Sequence
<220> FEATURE:
<223> OTHER INFORMATION: Description of Artificial Sequence: Synthetic
      CCC2-KGHRGF polypeptide
<220> FEATURE:
<221> NAME/KEY: MOD_RES
<222> LOCATION: (5)..(5)
<223> OTHER INFORMATION: 4-Hydroxyproline
<220> FEATURE:
<221> NAME/KEY: MOD_RES
<222> LOCATION: (8)..(8)
<223> OTHER INFORMATION: 4-Hydroxyproline
<220> FEATURE:
<221> NAME/KEY: MOD_RES
<222> LOCATION: (11)..(11)
<223> OTHER INFORMATION: 4-Hydroxyproline
<220> FEATURE:
<221> NAME/KEY: MOD_RES
<222> LOCATION: (14)..(14)
<223> OTHER INFORMATION: 4-Hydroxyproline
<220> FEATURE:
<221> NAME/KEY: MOD_RES
<222> LOCATION: (17)..(17)
<223> OTHER INFORMATION: 4-Hydroxyproline
```

```
<220> FEATURE:
<221> NAME/KEY: MOD_RES
<222> LOCATION: (29)..(29)
<223> OTHER INFORMATION: 4-Hydroxyproline
<220> FEATURE:
<221> NAME/KEY: MOD_RES
<222> LOCATION: (32)..(32)
<223> OTHER INFORMATION: 4-Hydroxyproline
<220> FEATURE:
<221> NAME/KEY: MOD_RES
<222> LOCATION: (35)..(35)
<223> OTHER INFORMATION: 4-Hydroxyproline
<220> FEATURE:
<221> NAME/KEY: MOD_RES
<222> LOCATION: (38)..(38)
<223> OTHER INFORMATION: 4-Hydroxyproline
<220> FEATURE:
<221> NAME/KEY: MOD_RES
<222> LOCATION: (41)..(41)
<223> OTHER INFORMATION: 4-Hydroxyproline
<220> FEATURE:
<221> NAME/KEY: MOD_RES
<222> LOCATION: (44)..(44)
<223> OTHER INFORMATION: 4-Hydroxyproline

<400> SEQUENCE: 18

Cys Cys Cys Pro Pro Gly Pro Pro Gly Pro Pro Gly Pro Pro Gly Pro
1               5                   10                  15

Pro Gly Pro Lys Gly His Arg Gly Phe Ser Gly Leu Pro Gly Pro Pro
            20                  25                  30

Gly Pro Pro Gly Pro Pro Gly Pro Pro Gly Pro Pro Gly Cys Cys Cys
        35                  40                  45

<210> SEQ ID NO 19
<211> LENGTH: 34
<212> TYPE: PRT
<213> ORGANISM: Artificial Sequence
<220> FEATURE:
<223> OTHER INFORMATION: Description of Artificial Sequence: Synthetic
      Soluble GFOGER polypeptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: 4-Hydroxyproline
<220> FEATURE:
<221> NAME/KEY: MOD_RES
<222> LOCATION: (6)..(6)
<223> OTHER INFORMATION: 4-Hydroxyproline
<220> FEATURE:
<221> NAME/KEY: MOD_RES
<222> LOCATION: (9)..(9)
<223> OTHER INFORMATION: 4-Hydroxyproline
<220> FEATURE:
<221> NAME/KEY: MOD_RES
<222> LOCATION: (12)..(12)
<223> OTHER INFORMATION: 4-Hydroxyproline
<220> FEATURE:
<221> NAME/KEY: MOD_RES
<222> LOCATION: (15)..(15)
<223> OTHER INFORMATION: 4-Hydroxyproline
<220> FEATURE:
<221> NAME/KEY: MOD_RES
<222> LOCATION: (21)..(21)
<223> OTHER INFORMATION: 4-Hydroxyproline
<220> FEATURE:
<221> NAME/KEY: MOD_RES
<222> LOCATION: (24)..(24)
<223> OTHER INFORMATION: 4-Hydroxyproline
<220> FEATURE:
<221> NAME/KEY: MOD_RES
<222> LOCATION: (27)..(27)
<223> OTHER INFORMATION: 4-Hydroxyproline
<220> FEATURE:
```

```
<221> NAME/KEY: MOD_RES
<222> LOCATION: (30)..(30)
<223> OTHER INFORMATION: 4-Hydroxyproline
<220> FEATURE:
<221> NAME/KEY: MOD_RES
<222> LOCATION: (33)..(33)
<223> OTHER INFORMATION: 4-Hydroxyproline
<220> FEATURE:
<223> OTHER INFORMATION: C-term NH2

<400> SEQUENCE: 19

Gly Pro Pro Gly Pro Pro Gly Pro Pro Gly Pro Gly Phe Pro Gly
1               5                   10                  15

Glu Arg Gly Pro Pro Gly Pro Pro Gly Pro Pro Gly Pro Pro Gly Pro
                20                  25                  30

Pro Gly

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      Soluble GVMGFO polypeptide
<220> FEATURE:
<221> NAME/KEY: MOD_RES
<222> LOCATION: (3)..(3)
<223> OTHER INFORMATION: 4-Hydroxyproline
<220> FEATURE:
<221> NAME/KEY: MOD_RES
<222> LOCATION: (6)..(6)
<223> OTHER INFORMATION: 4-Hydroxyproline
<220> FEATURE:
<221> NAME/KEY: MOD_RES
<222> LOCATION: (9)..(9)
<223> OTHER INFORMATION: 4-Hydroxyproline
<220> FEATURE:
<221> NAME/KEY: MOD_RES
<222> LOCATION: (12)..(12)
<223> OTHER INFORMATION: 4-Hydroxyproline
<220> FEATURE:
<221> NAME/KEY: MOD_RES
<222> LOCATION: (18)..(18)
<223> OTHER INFORMATION: 4-Hydroxyproline
<220> FEATURE:
<221> NAME/KEY: MOD_RES
<222> LOCATION: (24)..(24)
<223> OTHER INFORMATION: 4-Hydroxyproline
<220> FEATURE:
<221> NAME/KEY: MOD_RES
<222> LOCATION: (27)..(27)
<223> OTHER INFORMATION: 4-Hydroxyproline
<220> FEATURE:
<221> NAME/KEY: MOD_RES
<222> LOCATION: (30)..(30)
<223> OTHER INFORMATION: 4-Hydroxyproline
<220> FEATURE:
<221> NAME/KEY: MOD_RES
<222> LOCATION: (33)..(33)
<223> OTHER INFORMATION: 4-Hydroxyproline
<220> FEATURE:
<221> NAME/KEY: MOD_RES
<222> LOCATION: (36)..(36)
<223> OTHER INFORMATION: 4-Hydroxyproline
<220> FEATURE:
<223> OTHER INFORMATION: C-term NH2

<400> SEQUENCE: 20

Gly Pro Pro Gly Pro Pro Gly Pro Pro Gly Pro Pro Gly Pro Arg Gly
1               5                   10                  15

Gln Pro Gly Val Met Gly Phe Pro Gly Pro Pro Gly Pro Pro Gly Pro
                20                  25                  30
```

Pro Gly Pro Pro Gly
         35

<210> SEQ ID NO 21
<211> LENGTH: 52
<212> TYPE: PRT
<213> ORGANISM: Artificial Sequence
<220> FEATURE:
<223> OTHER INFORMATION: Description of Artificial Sequence: Synthetic
      Soluble KGHRGF polypeptide
<220> FEATURE:
<221> NAME/KEY: MOD_RES
<222> LOCATION: (3)..(3)
<223> OTHER INFORMATION: 4-Hydroxyproline
<220> FEATURE:
<221> NAME/KEY: MOD_RES
<222> LOCATION: (6)..(6)
<223> OTHER INFORMATION: 4-Hydroxyproline
<220> FEATURE:
<221> NAME/KEY: MOD_RES
<222> LOCATION: (9)..(9)
<223> OTHER INFORMATION: 4-Hydroxyproline
<220> FEATURE:
<221> NAME/KEY: MOD_RES
<222> LOCATION: (12)..(12)
<223> OTHER INFORMATION: 4-Hydroxyproline
<220> FEATURE:
<221> NAME/KEY: MOD_RES
<222> LOCATION: (15)..(15)
<223> OTHER INFORMATION: 4-Hydroxyproline
<220> FEATURE:
<221> NAME/KEY: MOD_RES
<222> LOCATION: (18)..(18)
<223> OTHER INFORMATION: 4-Hydroxyproline
<220> FEATURE:
<221> NAME/KEY: MOD_RES
<222> LOCATION: (21)..(21)
<223> OTHER INFORMATION: 4-Hydroxyproline
<220> FEATURE:
<221> NAME/KEY: MOD_RES
<222> LOCATION: (33)..(33)
<223> OTHER INFORMATION: 4-Hydroxyproline
<220> FEATURE:
<221> NAME/KEY: MOD_RES
<222> LOCATION: (36)..(36)
<223> OTHER INFORMATION: 4-Hydroxyproline
<220> FEATURE:
<221> NAME/KEY: MOD_RES
<222> LOCATION: (39)..(39)
<223> OTHER INFORMATION: 4-Hydroxyproline
<220> FEATURE:
<221> NAME/KEY: MOD_RES
<222> LOCATION: (42)..(42)
<223> OTHER INFORMATION: 4-Hydroxyproline
<220> FEATURE:
<221> NAME/KEY: MOD_RES
<222> LOCATION: (45)..(45)
<223> OTHER INFORMATION: 4-Hydroxyproline
<220> FEATURE:
<221> NAME/KEY: MOD_RES
<222> LOCATION: (48)..(48)
<223> OTHER INFORMATION: 4-Hydroxyproline
<220> FEATURE:
<221> NAME/KEY: MOD_RES
<222> LOCATION: (51)..(51)
<223> OTHER INFORMATION: 4-Hydroxyproline
<220> FEATURE:
<223> OTHER INFORMATION: C-term NH2

<400> SEQUENCE: 21

Gly Pro Pro Gly Pro Pro Gly Pro Pro Gly Pro Pro Gly Pro Pro Gly
1               5                   10                  15

Pro Pro Gly Pro Pro Gly Ile Lys Gly His Arg Gly Phe Ser Gly Leu
            20                  25                  30

Pro Gly Pro Pro Gly Pro Pro Gly Pro Pro Gly Pro Pro Gly Pro Pro

-continued

```
                   35                  40                  45
Gly Pro Pro Gly
    50

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      RGD pep peptide
<220> FEATURE:
<223> OTHER INFORMATION: C-term NH2

<400> SEQUENCE: 22

Gly Arg Gly Asp Ser
1               5

<210> SEQ ID NO 23
<211> LENGTH: 34
<212> TYPE: PRT
<213> ORGANISM: Artificial Sequence
<220> FEATURE:
<223> OTHER INFORMATION: Description of Artificial Sequence: Synthetic
      CC2-GPOGPR (short) polypeptide
<220> FEATURE:
<221> NAME/KEY: MOD_RES
<222> LOCATION: (4)..(4)
<223> OTHER INFORMATION: 4-Hydroxyproline
<220> FEATURE:
<221> NAME/KEY: MOD_RES
<222> LOCATION: (7)..(7)
<223> OTHER INFORMATION: 4-Hydroxyproline
<220> FEATURE:
<221> NAME/KEY: MOD_RES
<222> LOCATION: (10)..(10)
<223> OTHER INFORMATION: 4-Hydroxyproline
<220> FEATURE:
<221> NAME/KEY: MOD_RES
<222> LOCATION: (13)..(13)
<223> OTHER INFORMATION: 4-Hydroxyproline
<220> FEATURE:
<221> NAME/KEY: MOD_RES
<222> LOCATION: (16)..(16)
<223> OTHER INFORMATION: 4-Hydroxyproline
<220> FEATURE:
<221> NAME/KEY: MOD_RES
<222> LOCATION: (22)..(22)
<223> OTHER INFORMATION: 4-Hydroxyproline
<220> FEATURE:
<221> NAME/KEY: MOD_RES
<222> LOCATION: (25)..(25)
<223> OTHER INFORMATION: 4-Hydroxyproline
<220> FEATURE:
<221> NAME/KEY: MOD_RES
<222> LOCATION: (28)..(28)
<223> OTHER INFORMATION: 4-Hydroxyproline
<220> FEATURE:
<221> NAME/KEY: MOD_RES
<222> LOCATION: (31)..(31)
<223> OTHER INFORMATION: 4-Hydroxyproline

<400> SEQUENCE: 23

Cys Cys Pro Pro Gly Pro Pro Gly Pro Pro Gly Pro Pro Gly Pro Pro
1               5                   10                  15

Gly Pro Arg Gly Pro Pro Gly Pro Pro Gly Pro Pro Gly Pro Pro Gly
                20                  25                  30

Cys Cys

<210> SEQ ID NO 24
<211> LENGTH: 32
```

```
<212> TYPE: PRT
<213> ORGANISM: Artificial Sequence
<220> FEATURE:
<223> OTHER INFORMATION: Description of Artificial Sequence: Synthetic
      C2-GPOGPR (short) polypeptide
<220> FEATURE:
<221> NAME/KEY: MOD_RES
<222> LOCATION: (3)..(3)
<223> OTHER INFORMATION: 4-Hydroxyproline
<220> FEATURE:
<221> NAME/KEY: MOD_RES
<222> LOCATION: (6)..(6)
<223> OTHER INFORMATION: 4-Hydroxyproline
<220> FEATURE:
<221> NAME/KEY: MOD_RES
<222> LOCATION: (9)..(9)
<223> OTHER INFORMATION: 4-Hydroxyproline
<220> FEATURE:
<221> NAME/KEY: MOD_RES
<222> LOCATION: (12)..(12)
<223> OTHER INFORMATION: 4-Hydroxyproline
<220> FEATURE:
<221> NAME/KEY: MOD_RES
<222> LOCATION: (15)..(15)
<223> OTHER INFORMATION: 4-Hydroxyproline
<220> FEATURE:
<221> NAME/KEY: MOD_RES
<222> LOCATION: (21)..(21)
<223> OTHER INFORMATION: 4-Hydroxyproline
<220> FEATURE:
<221> NAME/KEY: MOD_RES
<222> LOCATION: (24)..(24)
<223> OTHER INFORMATION: 4-Hydroxyproline
<220> FEATURE:
<221> NAME/KEY: MOD_RES
<222> LOCATION: (27)..(27)
<223> OTHER INFORMATION: 4-Hydroxyproline
<220> FEATURE:
<221> NAME/KEY: MOD_RES
<222> LOCATION: (30)..(30)
<223> OTHER INFORMATION: 4-Hydroxyproline

<400> SEQUENCE: 24

Cys Pro Pro Gly Pro Pro Gly Pro Pro Gly Pro Pro Gly Pro Pro Gly
1               5                   10                  15

Pro Arg Gly Pro Pro Gly Pro Pro Gly Pro Pro Gly Pro Pro Gly Cys
                20                  25                  30

<210> SEQ ID NO 25
<211> LENGTH: 31
<212> TYPE: PRT
<213> ORGANISM: Artificial Sequence
<220> FEATURE:
<223> OTHER INFORMATION: Description of Artificial Sequence: Synthetic
      Soluble GPOGPR (short) polypeptide
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (3)..(3)
<223> OTHER INFORMATION: 4-Hydroxyproline
<220> FEATURE:
<221> NAME/KEY: MOD_RES
<222> LOCATION: (6)..(6)
<223> OTHER INFORMATION: 4-Hydroxyproline
<220> FEATURE:
<221> NAME/KEY: MOD_RES
<222> LOCATION: (9)..(9)
<223> OTHER INFORMATION: 4-Hydroxyproline
<220> FEATURE:
<221> NAME/KEY: MOD_RES
<222> LOCATION: (12)..(12)
<223> OTHER INFORMATION: 4-Hydroxyproline
<220> FEATURE:
```

```
<221> NAME/KEY: MOD_RES
<222> LOCATION: (18)..(18)
<223> OTHER INFORMATION: 4-Hydroxyproline
<220> FEATURE:
<221> NAME/KEY: MOD_RES
<222> LOCATION: (21)..(21)
<223> OTHER INFORMATION: 4-Hydroxyproline
<220> FEATURE:
<221> NAME/KEY: MOD_RES
<222> LOCATION: (24)..(24)
<223> OTHER INFORMATION: 4-Hydroxyproline
<220> FEATURE:
<221> NAME/KEY: MOD_RES
<222> LOCATION: (27)..(27)
<223> OTHER INFORMATION: 4-Hydroxyproline
<220> FEATURE:
<221> NAME/KEY: MOD_RES
<222> LOCATION: (30)..(30)
<223> OTHER INFORMATION: 4-Hydroxyproline

<400> SEQUENCE: 25

Ala Pro Pro Gly Pro Pro Gly Pro Pro Gly Pro Pro Gly Pro Arg Gly
1               5                   10                  15
Pro Pro Gly Pro Pro Gly Pro Pro Gly Pro Pro Gly Pro Pro Gly
            20                  25                  30

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline

<400> SEQUENCE: 26

Gly Phe Pro Gly Glu Arg
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 4-Hydroxyproline

<400> SEQUENCE: 27

Gly Val Met Gly Phe Pro
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Gly His Arg Gly Phe
1               5
```

```
<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Glu Asp Val
1

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Tyr Ile Gly Ser Arg
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Asp Ser Gly Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Tyr Val Val Leu Pro Arg
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Gly Thr Ile Pro Gly
1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34
```

Arg Asn Ile Ala Glu Ile Ile Lys Asp Ile
1               5                   10

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Lys Val Ala Val
1               5

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Gly Glu Ala
1

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: 4-Hydroxyproline
<220> FEATURE:
<221> NAME/KEY: MOD_RES
<222> LOCATION: (10)..(10)
<223> OTHER INFORMATION: 4-Hydroxyproline

<400> SEQUENCE: 37

Arg Gly Gln Pro Gly Val Met Gly Phe Pro
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Gly His Arg Gly Phe Ser Gly Leu
1               5

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)

```
<223> OTHER INFORMATION: Any amino acid
<220> FEATURE:
<221> NAME/KEY: MISC_FEATURE
<222> LOCATION: (1)..(10)
<223> OTHER INFORMATION: This region may encompass 2-10 residues
<220> FEATURE:
<221> NAME/KEY: MOD_RES
<222> LOCATION: (11)..(12)
<223> OTHER INFORMATION: Pro, Hydroxyproline, Arg, Lys, Val, Leu, Ile,
      Ser, Thr, Ala, Gly, Phe, Met, Glu, Asp, Asn, Gln, His, Trp, Tyr or
      N-isobutyl glycine
<220> FEATURE:
<221> NAME/KEY: MOD_RES
<222> LOCATION: (17)..(18)
<223> OTHER INFORMATION: Pro, Hydroxyproline, Arg, Lys, Val, Leu, Ile,
      Ser, Thr, Ala, Gly, Phe, Met, Glu, Asp, Asn, Gln, His, Trp, Tyr or
      N-isobutyl glycine
<220> FEATURE:
<221> NAME/KEY: MOD_RES
<222> LOCATION: (21)..(21)
<223> OTHER INFORMATION: Hydroxyproline
<220> FEATURE:
<221> NAME/KEY: MOD_RES
<222> LOCATION: (23)..(32)
<223> OTHER INFORMATION: Any amino acid
<220> FEATURE:
<221> NAME/KEY: MISC_FEATURE
<222> LOCATION: (23)..(32)
<223> OTHER INFORMATION: This region may encompass 2-10 residues
<220> FEATURE:
<223> OTHER INFORMATION: See specification as filed for detailed
      description of substitutions and preferred embodiments

<400> SEQUENCE: 39

Xaa Xaa Xaa Xaa Xaa Xaa Xaa Xaa Xaa Xaa Xaa Xaa Gly Pro Arg Gly
1               5                   10                  15

Xaa Xaa Gly Pro Pro Gly Xaa Xaa Xaa Xaa Xaa Xaa Xaa Xaa Xaa
            20                  25                  30

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: 4-Hydroxyproline

<400> SEQUENCE: 40

Gly Pro Pro Gly Pro Arg
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Gly His Arg Gly Asp
1               5
```

POLYMERIZED PEPTIDE AND GEL HAVING COLLAGEN-LIKE STRUCTURE

CROSS-REFERENCE TO RELATED APPLICATIONS

This application is a § 371 national stage entry of International Application No. PCT/JP2016/068667, filed Jun. 23, 2016, which claims priority to and the benefit of Japanese Application No. 2015-127450, filed Jun. 25, 2015, both of which are hereby incorporated herein by reference in their entireties.

REFERENCE TO A SEQUENCE LISTING SUBMITTED IN COMPUTER READABLE FORM

This application includes a "Sequence Listing" which is provided in computer readable form (CRF). The file "1625-240_157644_00801_SL.txt" was created on Jan. 31, 2019 and is 35,239 bytes, which is herein incorporated by reference in its entirety.

TECHNICAL FIELD

The present invention relates to a polymerized peptide containing a collagen-like peptide, a gel and a polymerized peptide membrane containing the polymerized peptide, a method for producing the same and uses thereof.

BACKGROUND ART

Collagen is a generic term for proteins in which triple chains of a peptide having a primary structure of an amino acid sequence composed of repeats of -(Xaa-Yaa-Gly)- as a basic unit form a triple-helical structure, and is a major component of an extracellular matrix present between cells of animal tissue. It is abundant in animal connective tissue and constitutes the skeletal structure of the tissue. There are 28 different types of human collagen protein reported. Meanwhile, a physiologically active motif is incorporated in the amino acid sequence of the above primary structure, such that exposure of collagen in the tissue to blood at the time of tissue injury such as wound, for example, causes binding of platelets in the blood having integrin $\alpha 2\beta 1$ and glycoprotein VI (GPVI) to the region of wound, thus triggering the activation of the blood clotting system, having activities such as hemostasis and acceleration of wound healing (Non-Patent Document 1).

For this reason, taking advantage of the strength and physiological activity possessed by collagen, gelatin produced by thermally extracting collagen collected from livestock, fish and the like with water has been widely used for medicines and medical materials meeting the indications of hemostasis and decubitus ulcers; as a raw material for encapsulated formulation; and as a cosmetic raw material and a food material.

However, when the onset of common infections with human beings, such as prion disease, is confirmed in livestock from which collagen is collected, supply of collagen from the livestock is regulated in order to ensure safety, thus making the supply of collagen to related industrial fields unstable.

In addition, natural collagen has various activities such as adhesion of cells having a discoidin domain receptors, a syndecans and fibronectin, as well as the aforesaid action on platelets through the integrin $\alpha 2\beta 1$ and the like (Non-Patent Document 1). For this reason, it is substantially difficult to obtain a collagen having selected activities for desired physiological activities from natural collagen to utilize the same.

In view of these characteristics of collagen, there have been attempts to produce non-natural, collagen-like peptides having a collagen-like structure and activity to be used in applications on research materials, medical materials, etc. (Patent Documents 1 and 2).

PRIOR ART DOCUMENTS

Patent Documents

Patent Document 1: Japanese Un-examined Patent Application Publication No. 2005-263784
Patent Document 2: Japanese Un-examined Patent Application Publication No. 2013-074936

Non-Patent Document

Non-Patent Document 1: Koide T., PhiL. Trans. R. Soc. B (2007) 362, 1281-1291

SUMMARY OF THE INVENTION

Problems to be Solved by the Invention

Collagen is useful as a medical material, and yet its use for humans involves risks of allergy and parasitic zoonosis. Therefore, use of collagen-like peptides such as artificial collagen or artificial gelatin as a medical material has been studied. However, conventional collagen-like peptides have been not always satisfactory in terms of their physical strength and some properties such as denaturation by heat, and inability to be processed into sheets.

Means for Solving the Problems

The present invention provides a medical material and a research material which can mimic or newly endow with the structural/physical properties and physiological functions of collagen, and can be given as a complete artificial product to ensure safety. A collagen-like peptide having a triple-helical structure composed of triple strands of peptide chains containing a plurality of cysteine (Cys) residues is subjected to oxidative cross-linking to be produced as a polymerized peptide. The material containing the present polymerized peptide can be used after being processed into a hydrogel or a sheet. Further, by incorporating a functional amino acid sequence present on a biopolymer such as an integrin-binding sequence, it is possible to endow the material with specific physiological functions such as cell adhesiveness. Furthermore, the present invention provides a method for producing a hydrogel and a sheet-shaped processed product, and uses as a composition of cell cultures, wound dressings, regenerative medical materials, research materials and the like using them.

Specifically, according to the present invention, there is provided a polymerized peptide that has, as a repeating unit, a triple-chain peptide having a triple-helical structure, and is polymerized through oxidative cross-linking, wherein peptide chains composing the triple-chain peptide are identical to or different from one another, and each peptide chain has:
one or more triple helix forming peptidyl groups each having a repeating structure in which -(Xaa-Yaa-Gly)- as a basic unit is repeated at least 5 times; and one or more cross-link forming peptidyl groups each containing at least two cysteine (Cys) residues within 10 residues from each of an amino-terminus and a carboxy-terminus, and wherein each of Xaa and Yaa is independently selected from a proline (Pro or P) residue, a hydroxyproline (Hyp or O) residue, an arginine (Arg or R) residue, a lysine (Lys or K) residue, a valine (Val or V) residue, a leucine (Leu or L) residue, an isoleucine (Ile or I) residue, a serine (Ser or S) residue, a threonine (Thr or T) residue, an alanine (Ala or A) residue, a glycine (Gly or G) residue, a phenylalanine (Phe or F) residue, a methionine (Met or M) residue, a glutamate (Glu or E) residue, an aspartate (Asp or D) residue, an asparagine (Asn or N) residue, a glutamine (Gln or Q) residue, a histidine (His or H) residue, a tryptophan (Trp or W) residue or a tyrosine (Tyr or Y) residue, wherein the proline residue may be modified by an amino group or a fluorine atom, and each of the Xaa position and Yaa position may employ an N-isobutyl glycine residue.

The polymerized peptide of the present invention may be the one in which the peptide chains are at least one selected from the group consisting of:

(i) a peptide chain containing at least one of the triple helix forming peptidyl group (s) and at least one of the cross-link forming peptidyl group(s);

(ii) a peptide chain containing at least one of the triple helix forming peptidyl group(s), at least one of the cross-link forming peptidyl group(s) and at least one peptidyl group having a motif having a bioactivity; and (iii) a peptide chain containing at least one of the triple helix forming peptidyl group (s), at least one of the cross-link forming peptidyl group(s), and at least one peptidyl group having an amino acid residue linking a bioactive motif to a side chain thereof through a linker.

The polymerized peptide of this embodiment may also be described as that having the following structure.

That is, this polymerized peptide is the aforementioned polymerized peptide having an oxidatively cross-linked structural unit of a trimer peptide that is formed of three peptide chains and is represented by the following formula (I).

[Chemical formula 1]

[In the formula (I), $A_1$, $A_2$ and $A_3$ may be identical to or different from one another, and independently represent peptide chains expressed by the following formula (II). $A_1$, $A_2$ and $A_3$ form a trimer having a triple-helical structure, and may be cross-linked through disulfide bonds established between the cysteine (Cys) residues contained in each peptide chain. This trimer is polymerized by oxidative cross-linking established by the disulfide bonds of Cys.

[Chemical formula 2]

(In the formula (II), $R_1$ and $R_4$ individually represent an amino-terminus and a carboxy-terminus, and each of $R_1$ and $R_4$ independently represents a peptidyl group composed of any 2 to 10 amino acid residues containing at least two Cys residues. Z represents at least one selected from:

(i) a peptidyl group only composed of a repeating structure whose basic unit is -(Xaa-Yaa-Gly)-;

(ii) a peptidyl group having the repeating structure whose basic unit is -(Xaa-Yaa-Gly)- and a motif having a bioactivity; or (iii) a peptidyl group having the repeating structure whose basic unit is -(Xaa-Yaa-Gly)-, and a biologically active motif sequence bound, through a linker, to the side chain(s) of at least one amino acid residue contained in such peptide chains Each of $R_2$ and $R_3$ independently represents a peptidyl group having a structure continuously repeating -(Xaa-Yaa-Gly)- as a unit.

As for the number of times -(Xaa-Yaa-Gly)- as the basic unit is repeated in the repeating structure, -(Xaa-Yaa-Gly)- as the basic unit is repeated not less than 0 times in each of $R_2$, Z and $R_3$; and not less than 3 times in $R_2$, Z and $R_3$ in total. m represents an integer of not smaller than 1.)]

In the invention of the above polymerized peptide, the peptide chains may each be represented by the following formula (III).

[Chemical formula 3] (SEQ ID NO: 39 disclosed below)

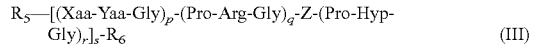

[In the formula (III), $R_5$ and $R_6$ individually represent an amino-terminus and a carboxy-terminus, and each independently represents a peptidyl group composed of any 2 to 10 amino acid residues containing at least two Cys residues. Each of p, q and r represents an integer of not smaller than 0, and a sum total of p, q and r is not smaller than 3. s represents an integer of not smaller than 11

In the invention of the above polymerized peptide, the bioactivity may be a binding activity specific to a biopolymer.

In the invention of the above polymerized peptide, a binding motif of a ligand having the above binding activity specific to a biopolymer may be a polymerized peptide selected from at least one of the binding motifs related to a collagen receptors selected from integrins, discoidin domain receptors (DDRs) or heparan sulfate proteoglycans (HSPGs) and a binding motif corresponding to fibronectin-derived integrin αvβ3.

In the invention of the above polymerized peptide, the binding motif related to integrins may be -Gly-Phe-Hyp-Gly-Glu-Arg- (SEQ ID NO: 26); the binding motif related to discoidin domain receptors may be -Gly-Val-Met-Gly-Phe-Hyp- (SEQ ID NO: 27); the binding motif amino acid sequence related to heparan sulfate proteoglycans may be -Lys-Gly-His-Arg-Gly-Phe- (SEQ ID NO: 28); and the binding motif corresponding to fibronectin-derived integrin αvβ3 may be -Arg-Gly-Asp-.

In the invention of the above polymerized peptide, the aforementioned peptide chains may be selected from the peptides having the amino acid sequences selected from the SEQ ID NOs: 1 to 7, 10 to 18, 23 and 24.

In the invention of the above polymerized peptide, the aforementioned peptide chains may contain amino acid sequences obtained by deleting, replacing or adding one or several amino acids from or to the amino acid sequences of the peptides having the amino acid sequences selected from the SEQ ID NOs: 1 to 7, 10 to 18, 23 and 24.

In the invention of the above polymerized peptide, the aforementioned peptide chains may be selected from the peptides having the amino acid sequences selected from the SEQ ID NOs: 1, 2, 5 to 7, 10 to 18, and 23.

In the invention of the above polymerized peptide, the aforementioned peptide chains may contain amino acid sequences obtained by deleting, replacing or adding one or several amino acids from or to the amino acid sequences of the peptides having the amino acid sequences selected from the SEQ ID NOs: 1, 2, 5 to 7, 10 to 18, and 23.

In the invention of the above polymerized peptide, the aforementioned peptide chains having a biologically active motif may be the one in which a fibronectin-derived integrin-binding motif is linked to the side chain(s) of the Lys residue contained in the peptidyl group through Bis (NHS) PEGS (bis(succinimidyl)penta(ethylene glycol) as a linker.

In the invention of the above polymerized peptide, it may be a copolymerized peptide produced by combining not less than two kinds of the biologically active motifs.

Also, according to the present invention, there is provided a method for producing the polymerized peptide, containing:

dissolving into a solvent identical or different peptide chains each having a repeating structure in which (Xaa-Yaa-Gly) as a basic unit is repeated at least 5 times, containing at least two cysteine (Cys) residues within 10 residues from each of an amino-terminus and a carboxy-terminus;

forming a triple-chain peptide having a triple-helical structure composed of three of the peptides, through self-assembly by cooling; and performing polymerization through oxidative cross-linking with the triple-chain peptide being a structural unit, wherein each of Xaa and Yaa is independently selected from a proline (Pro or P) residue, a hydroxyproline (Hyp or O) residue, an arginine (Arg or R) residue, a lysine (Lys or K) residue, a valine (Val or V) residue, a leucine (Leu or L) residue, an isoleucine (Ile or I) residue, a serine (Ser or S) residue, a threonine (Thr or T) residue, an alanine (Ala or A) residue, a glycine (Gly or G) residue, a phenylalanine (Phe or F) residue, a methionine (Met or M) residue, a glutamate (Glu or E) residue, an aspartate (Asp or D) residue, an asparagine (Asn or N) residue, a glutamine (Gln or Q) residue, a histidine (His or H) residue, a tryptophan (Trp or W) residue or a tyrosine (Tyr or Y) residue, the proline residue may be modified by an amino group or fluorine atom, and each of the Xaa position and Yaa position may employ an N-isobutyl glycine residue.

Further, the present invention provides a polymerized peptide produced by the aforementioned method for producing a polymerized peptide.

Further, the present invention provides a gelling agent containing at least one kind of the aforementioned polymerized peptides.

Further, the present invention provides a gel containing at least one kind of the aforementioned polymerized peptides.

The gel of the present invention may be the one containing one, two, three, four or five kinds of the aforementioned polymerized peptides.

The gel of the present invention may be the one containing a polymerized peptide obtained by combining at least two kinds of triple-chain peptides with the triple-chain peptide being a polymerization unit.

The gel of the present invention may be the one containing a polymerized peptide obtained by combining two, three, four or five kinds of the triple-chain peptides.

The gel of the present invention may be the one further containing at least one kind of a triple-chain peptide containing no cysteine residue.

The gel of the present invention may be the one produced by gelling at least one kind of a triple-chain peptide by oxidatively polymerizing the same.

The gel of the present invention may be the one produced by gelling one, two, three, four or five kinds of a triple-chain peptide by oxidatively polymerizing the same.

The gel of the present invention may be the one produced by mixing a triple-chain peptide composed of a peptide chain having a cysteine residue and a triple-chain peptide composed of a peptide chain having no cysteine residue, and then oxidatively polymerizing the same.

The gel may be a multifunctional polymerized peptide in which each of the peptide chains composing the triple-chain peptide contains the peptide chains containing different numbers of cysteine residues for controlling the stiffness of the gel, and the peptide chains having a bioactive motif.

In the multifunctional gel, the peptide chains for controlling the stiffness of the gel may be peptide chains containing different numbers of cysteine residues for controlling the stiffness of the gel in the vicinity of each of the amino-terminus and carboxy-terminus.

The number of cysteine residues in the peptide chains for controlling the stiffness of the gel for controlling the stiffness is selected from one, two or three, in the vicinity of each of the amino-terminus and carboxy-terminus, wherein the number may be identical or different in the vicinity of each of the amino-terminus and carboxy-terminus.

In the invention of the gel, the gel may be a hydrogel used as a base material for culturing selected cells.

Further, the present invention provides a polymerized peptide membrane produced by drying the gel.

Further, the present invention provides a regenerative medical material containing the polymerized peptide membrane.

In the invention of the regenerative medical material, the regenerative medical material may be a composition for promoting wound healing.

All of the documents referred to herein are incorporated herein, in their entirety, by reference

BRIEF DESCRIPTION OF THE DRAWINGS

FIG. 15C discloses "GFOGER" as SEQ ID NO: 26 and "KGHRGF" as SEQ ID NO: 28.

FIG. 17 discloses "KGHRGF" as SEQ ID NO: 18 and "RGD" as SEQ ID NO: 22.

FIG. 18B discloses "CCC2-GPOGPR (short)" in reference to SEQ ID NO: 10, "CC2-GPOGPR (short)" in reference to SEQ ID NO: 23 and "C2-GPOGPR (short)" in reference to SEQ ID NO: 24.

MODE FOR CARRYING OUT THE INVENTION

1. Polymerized Peptide of Collagen-Like Peptide

A triple-chain peptide of the present invention is usually referred to as a collagen-like peptide. In this specification, a "collagen-like peptide" refers to an unnatural peptide or polypeptide that is either a triple-chain peptide, as is the case of a natural collagen, containing three peptide chains, each having a repeating structure whose basic unit is -(Xaa-Yaa-Gly)- to self-assemble in a solvent and form a helical structure; or a peptide or polypeptide further cross-linked among such triple-chain peptides having the helical structure. However, each of Xaa and Yaa is independently selected from a proline (Pro or P) residue, a hydroxyproline (Hyp or O) residue, an arginine (Arg or R) residue, a lysine (Lys or K) residue, a valine (Val or V) residue, a leucine (Leu or L) residue, an isoleucine (Ile or I) residue, a serine (Ser or S) residue, a threonine (Thr or T) residue, an alanine (Ala or A) residue, a glycine (Gly or G) residue, a phenylalanine (Phe or F) residue, a methionine (Met or M) residue, a glutamate (Glu or E) residue, an aspartate (Asp or D) residue, an asparagine (Asn or N) residue, a glutamine (Gln or Q) residue, a histidine (His or H) residue, a tryptophan (Trp or W) residue or a tyrosine (Tyr or Y) residue. Here, the proline residue may be modified by an amino group or fluorine atom; and each of the Xaa position and Yaa position may employ an N-isobutyl glycine residue.

Figure 1:
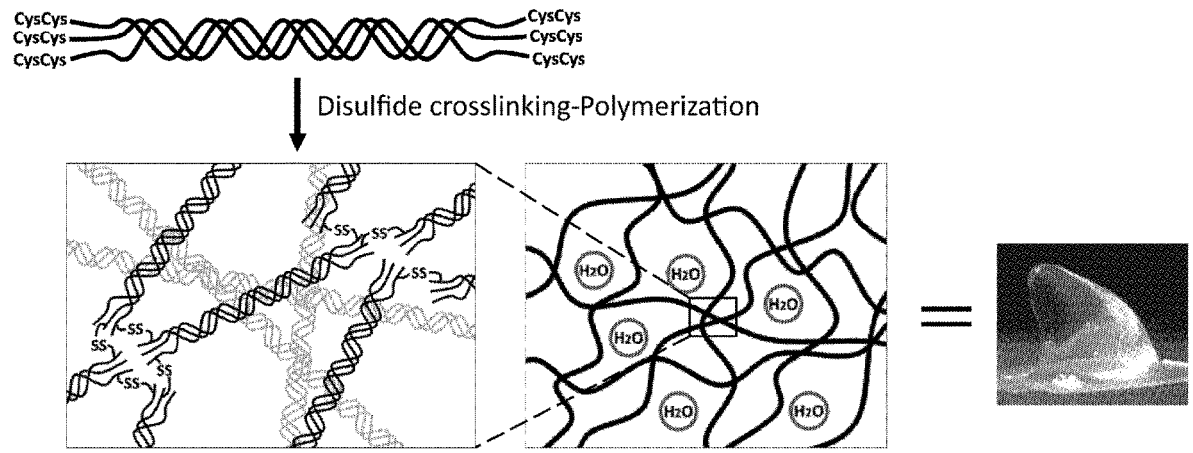
FIG. 1 is a schematic diagram showing a polymerized peptide of collagen-like peptide of the invention; and a gel and a polymerized peptide thin membrane that contain such polymerized peptide.
Figure 2A:
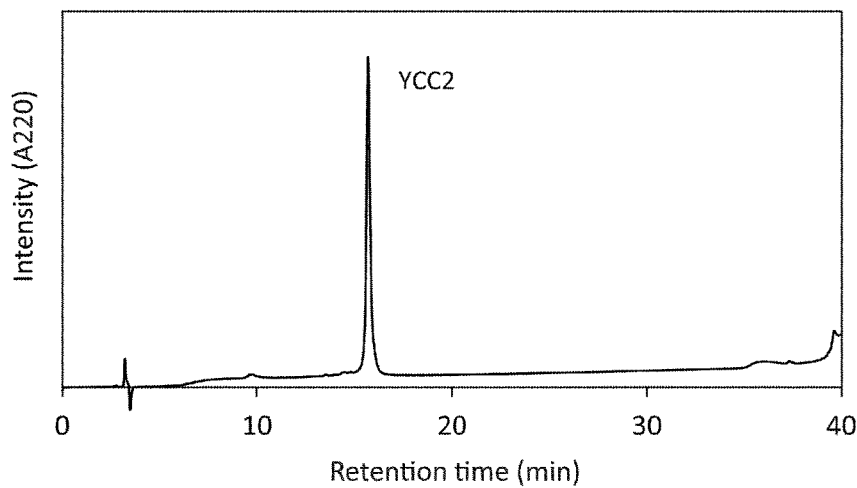
FIG. 2A is a chromatogram by reversed-phase high performance liquid chromatography (RP-HPLC) on a synthesized peptide: a chromatogram of YCC2 (SEQ ID NO: 1).
Figure 2B:
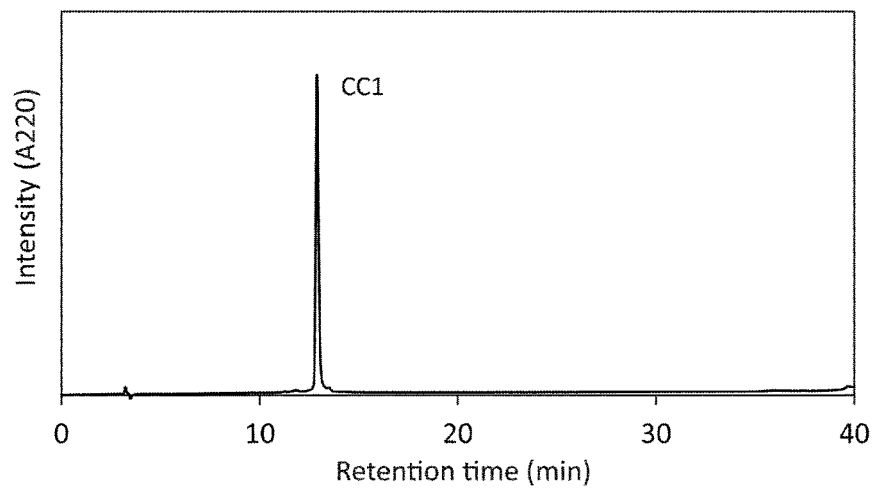
FIG. 2B is a chromatogram by reversed-phase high performance liquid chromatography (RP-HPLC) on a synthesized peptide: a chromatogram of CC1 (SEQ ID NO: 3).
Figure 2C:
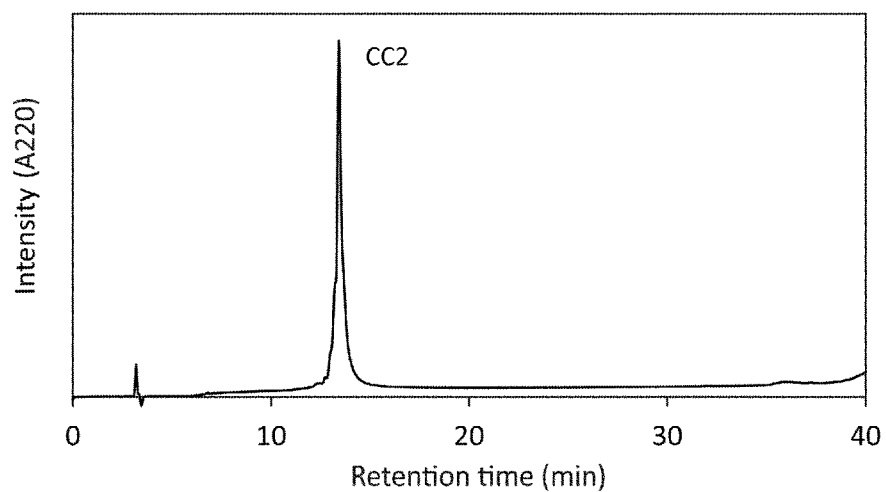
FIG. 2C is a chromatogram by reversed-phase high performance liquid chromatography (RP-HPLC) on a synthesized peptide: a chromatogram of CC2 (SEQ ID NO: 2).
Figure 2D:
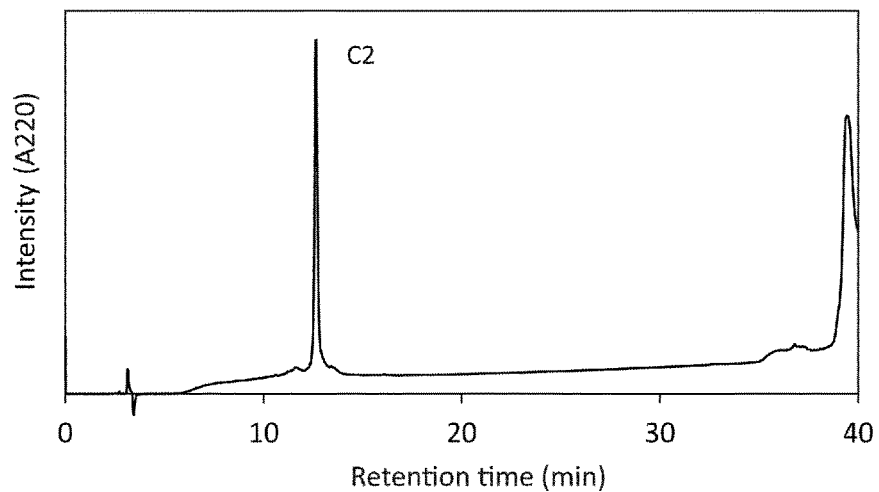
FIG. 2D is a chromatogram by reversed-phase high performance liquid chromatography (RP-HPLC) on a synthesized peptide: a chromatogram of C2 (SEQ ID NO: 4).
Figure 2E:
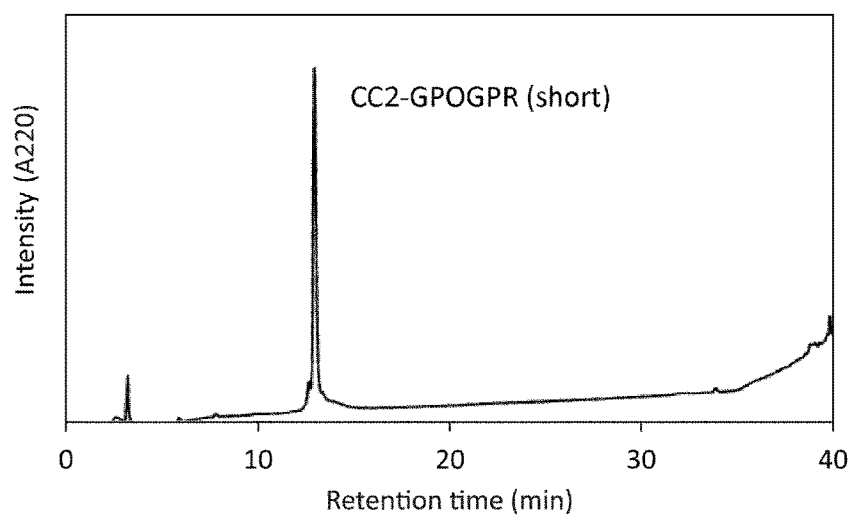
FIG. 2E is a chromatogram by reversed-phase high performance liquid chromatography (RP-HPLC) on a synthesized peptide: a chromatogram of CC2-GPOGPR (short) (SEQ ID NO: 23).
Figure 2F:
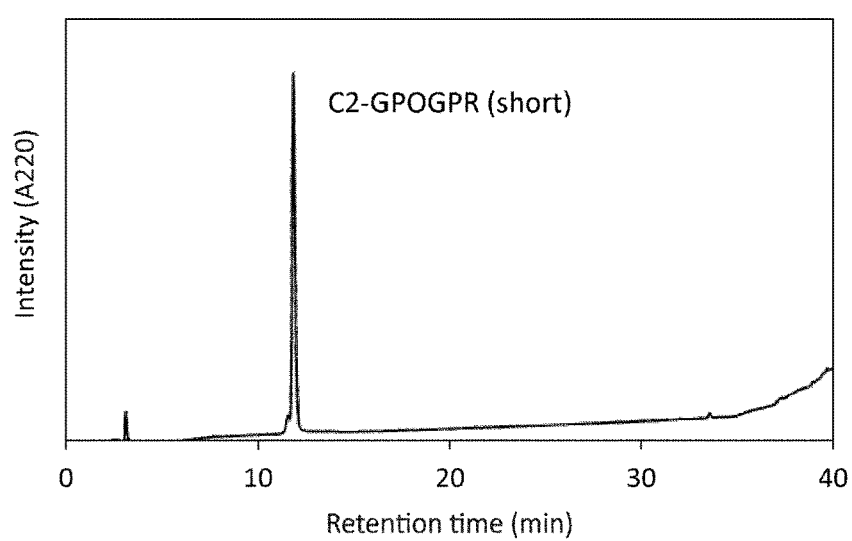
FIG. 2F is a chromatogram by reversed-phase high performance liquid chromatography (RP-HPLC) on a synthesized peptide: a chromatogram of C2-GPOGPR (short) (SEQ ID NO: 24).
Figure 2G:
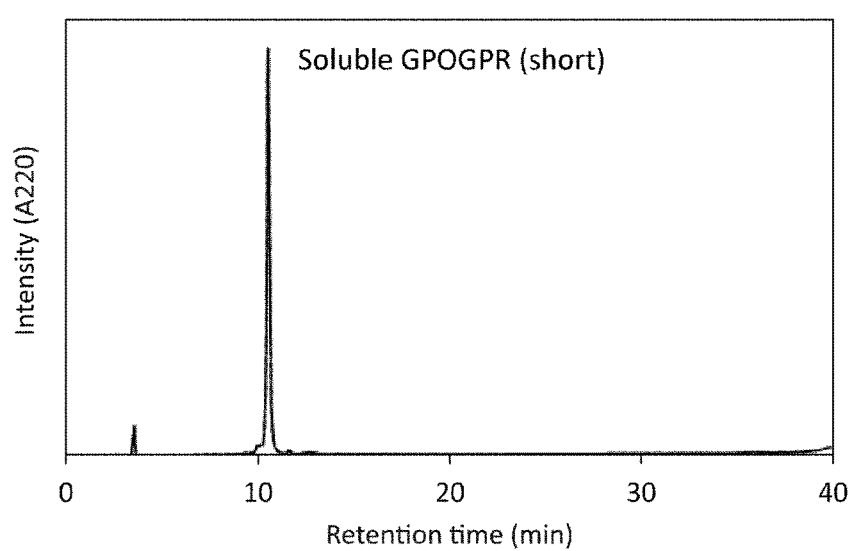
FIG. 2G is a chromatogram by reversed-phase high performance liquid chromatography (RP-HPLC) on a synthesized peptide: a chromatogram of Soluble GPOGPR (short) (SEQ ID NO: 25).
Figure 3A:
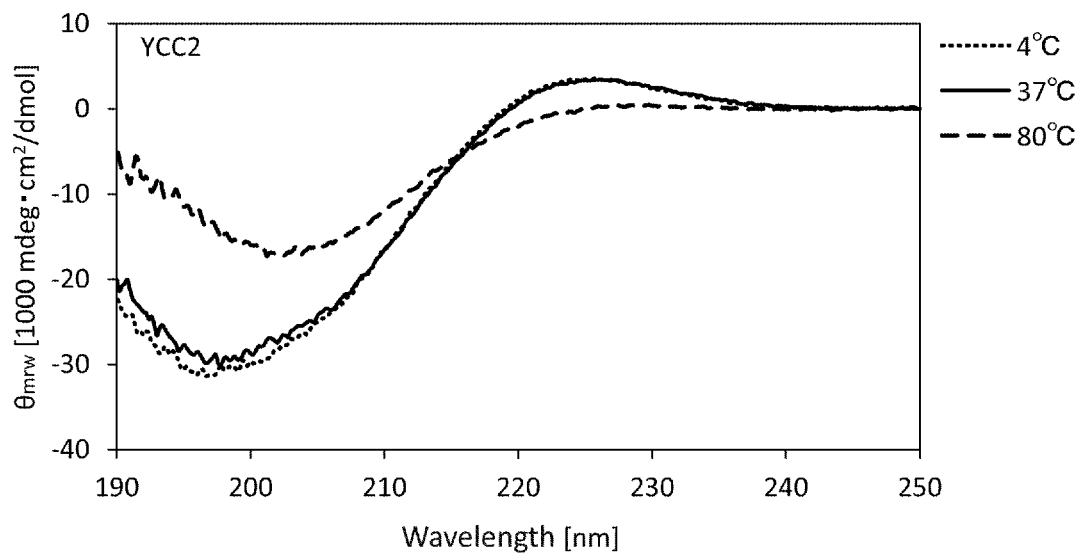
FIG. 3A shows a CD spectrum measurement result of a synthesized peptide chain at 4° C., 37° C. and 80° C.: CD spectrum of YCC2 (SEQ ID NO: 1).
Figure 3B:
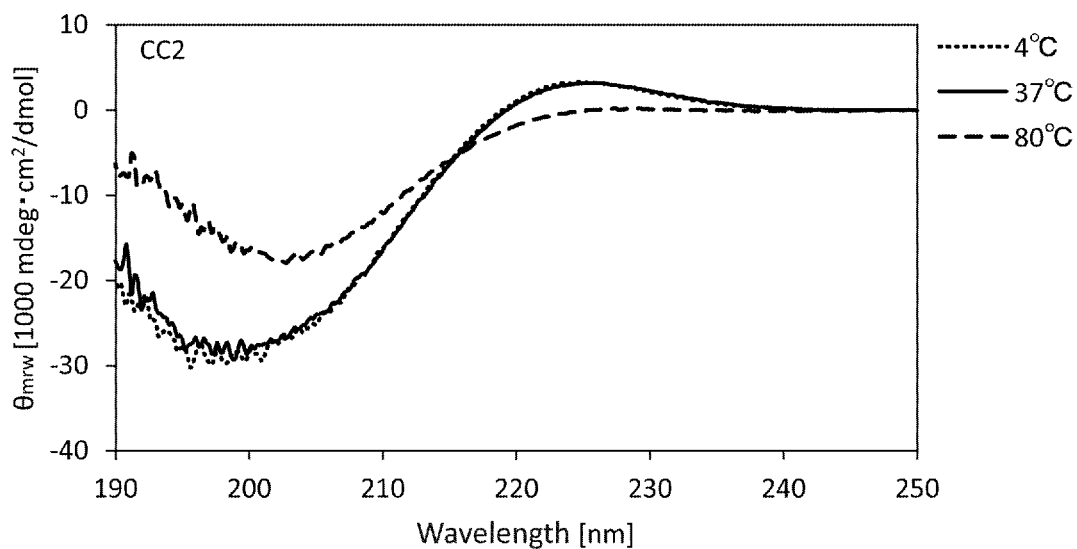
FIG. 3B shows a CD spectrum of a synthesized peptide chain at 4° C., 37° C. and 80° C.: CD spectrum of CC2 (SEQ ID NO: 2).
Figure 3C:
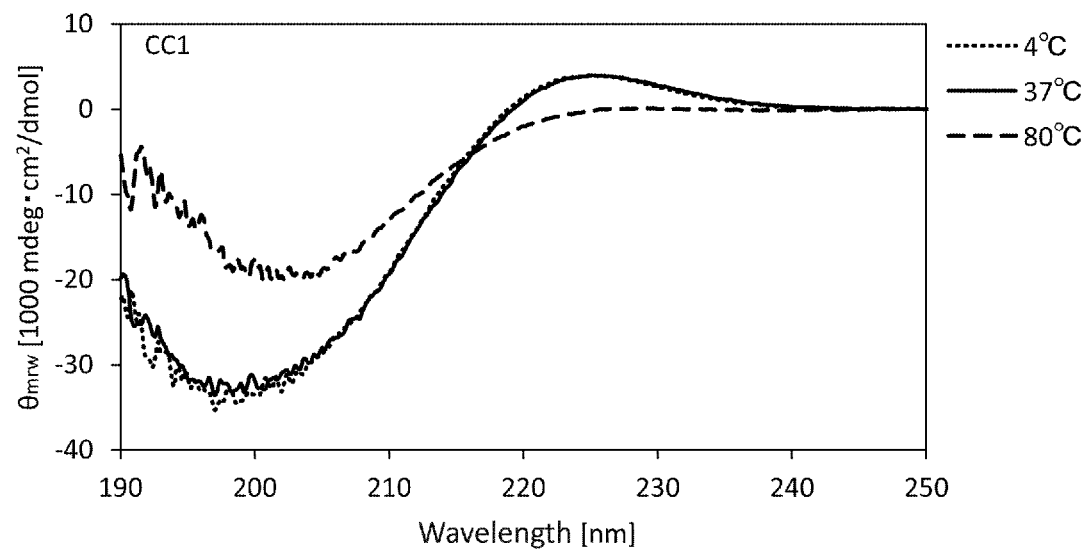
FIG. 3C shows a CD spectrum of a synthesized peptide chain at 4° C., 37° C. and 80° C.: CD spectrum of CC1 (SEQ ID NO: 3).
Figure 3D:
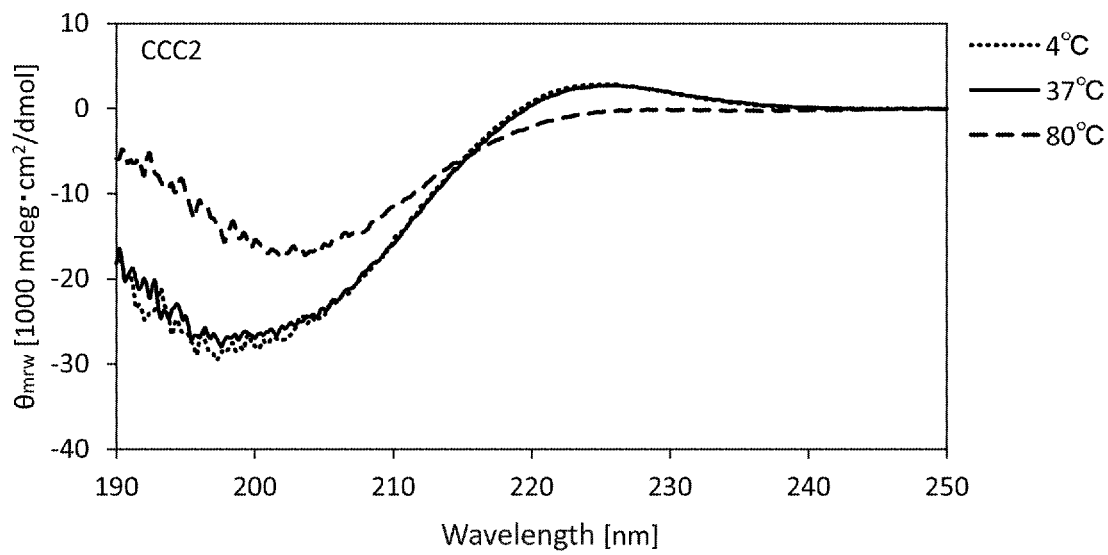
FIG. 3D shows a CD spectrum of a synthesized peptide chain at 4° C., 37° C. and 80° C.: CD spectrum of CCC2 (SEQ ID NO: 5).
Figure 3E:
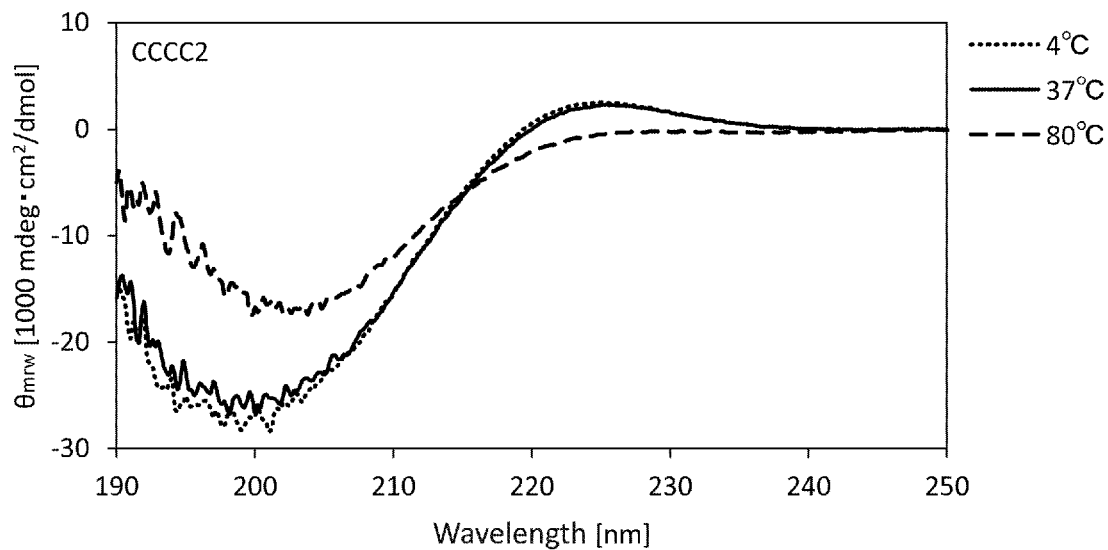
FIG. 3E shows a CD spectrum of a synthesized peptide chain at 4° C., 37° C. and 80° C.: CD spectrum of CCCC2 (SEQ ID NO: 7).
Figure 3F:
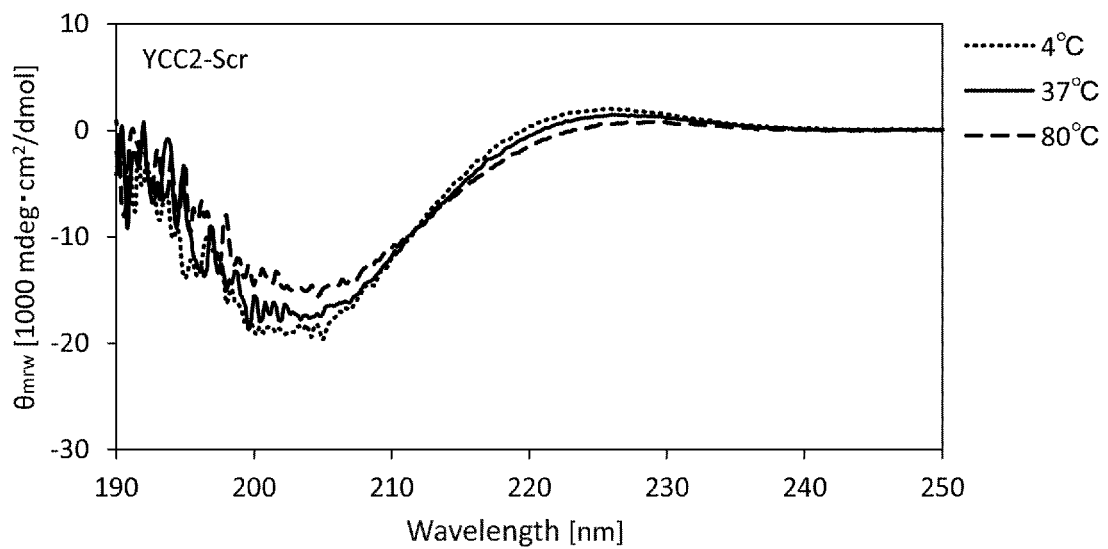
FIG. 3F shows a CD spectrum of a synthesized peptide chain at 4° C., 37° C. and 80° C.: CD spectrum of YCC2-Scr (SEQ ID NO: 9).
Figure 3G:
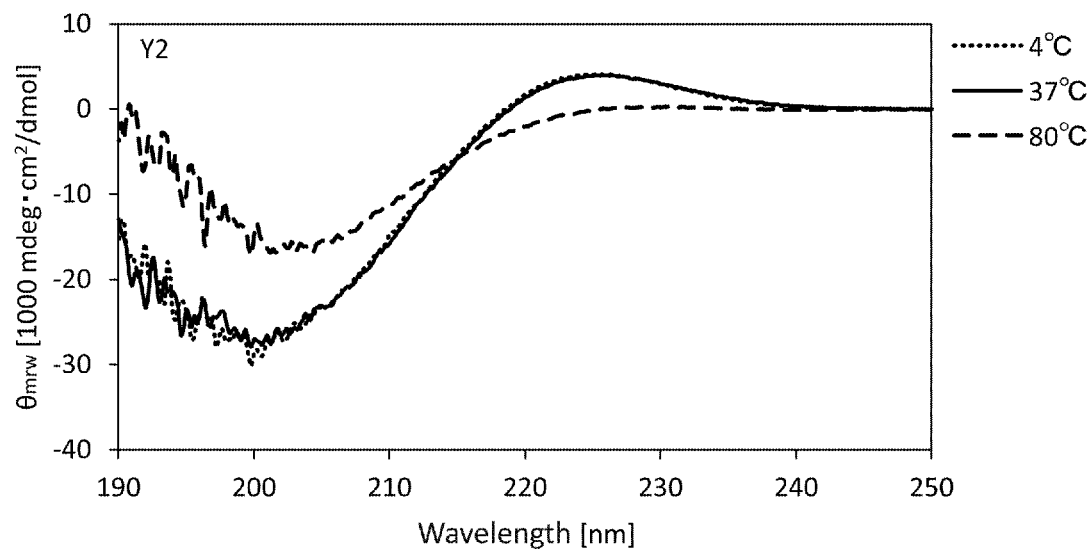
FIG. 3G shows a CD spectrum of a synthesized peptide chain at 4° C., 37° C. and 80° C.: CD spectrum of Y2 (SEQ ID NO: 8).

That is, one embodiment of the present invention is a triple-chain peptide i.e. polymerized peptide prepared by polymerizing a collagen-like peptide (see FIG. 1). This polymerized peptide of a collagen-like peptide has the following structure.

The polymerized peptide of a collagen-like peptide is a polymerized peptide that has, as a repeating unit, a triple-chain peptide having a triple-helical structure, and is polymerized by oxidative cross-linking. The peptide chains composing such triple-chain peptide may be either identical to or different from one another. Each peptide chain has a repeating structure in which -(Xaa-Yaa-Gly)- as the basic unit is repeated at least 5 times, and contains at least two cysteine (Cys) residues within 10 residues from each of the amino-terminus and carboxy-terminus. [each of Xaa and Yaa is independently selected from a proline (Pro or P) residue, a hydroxyproline (Hyp or O) residue, an arginine (Arg or R) residue, a lysine (Lys or K) residue, a valine (Val or V) residue, a leucine (Leu or L) residue, an isoleucine (Ile or I) residue, a serine (Ser or S) residue, a threonine (Thr or T) residue, an alanine (Ala or A) residue, a glycine (Gly or G) residue, a phenylalanine (Phe or F) residue, a methionine (Met or M) residue, a glutamate (Glu or E) residue, an aspartate (Asp or D) residue, an asparagine (Asn or N) residue, a glutamine (Gln or Q) residue, a histidine (His or H) residue, a tryptophan (Trp or W) residue or a tyrosine (Tyr or Y) residue. Here, the proline residue may be modified by an amino group or fluorine atom; and each of the Xaa position and Yaa position may employ an N-isobutyl glycine residue.]

In this specification, a "peptide chain" is a peptide or polypeptide having a primary structure needed to form the triple-helical structure by three peptide chains, may contain cysteine residues for forming oxidative cross-linking, and is at times referred to as "single-chain peptide."

The number of the Cys residues present within 10 residues from each of the amino-terminus and carboxy-terminus of such peptide chain is independent, and may be either identical or different. The number of such Cys residues may be not less than two, three, four or five.

In the structure of the above polymerized peptide, instead of 10 residues, peptidyl groups may be present within 9 residues, 8 residues, 7 residues, 6 residues, 5 residues, 4 residues or 3 residues from each of the amino-terminus and carboxy-terminus containing at least two cysteine (Cys) residues, respectively.

In this specification, a "polymerized peptide" refers to a peptide formed by, for example, polymerizing the "collagen-like peptide" by disulfide bonds formed by the oxidative cross-linking between the cysteine residues contained in such collagen peptide.

The polymerization degree of the polymerized peptide of the invention is not less than 2, and there are no particular restrictions as long as the polymerization degree is that capable of forming a gel, preferably hydrogel containing the polymerized peptide of the invention. However, an average polymerization degree may be less than 100; 100 to 500; 500 to 1,000; 1,000 to 5,000; 5,000 to 10,000; or not less than 10,000.

As for the repeating structure of the collagen-like peptide in which -(Xaa-Yaa-Gly)- serves as the basic unit, the minimum number of repetition varies depending on the amino acid residues composing the basic unit. It has been known that a stable triple-helical structure can be formed when the basic unit is repeated at least 5 times, provided that the basic unit contains 4-fluoroproline (Sakakibara S. (1973) Biochem. Biophys. Acta, 303, 198-202).

When -(Xaa-Yaa-Gly)- as the basic unit is repeated not less than 5 times, the collagen-like peptide is capable of forming a stable triple-helical structure. When -(Xaa-Yaa-Gly)- as the basic unit is repeated not less than 6 times, the collagen-like peptide is capable of forming a more stable triple-helical structure. When -(Xaa-Yaa-Gly)- as the basic unit is repeated not less than 7 times, the collagen-like peptide is capable of forming an even more stable triple-helical structure. When -(Xaa-Yaa-Gly)- as the basic unit is repeated not less than 8 times, the collagen-like peptide is capable of forming an even more stable triple-helical structure. When -(Xaa-Yaa-Gly)- as the basic unit is repeated not less than 9 times, the collagen-like peptide is capable of forming an even more stable triple-helical structure. When -(Xaa-Yaa-Gly)- as the basic unit is repeated not less than 10 times, the collagen-like peptide is capable of forming an even more stable triple-helical structure. When -(Xaa-Yaa-Gly)- as the basic unit is repeated not less than 11 times, the collagen-like peptide is capable of forming an even more stable triple-helical structure. When -(Xaa-Yaa-Gly)- as the basic unit is repeated not less than 12 times, the collagen-like peptide is capable of forming an even more stable triple-helical structure.

That is, with regard to the polymerized peptide of the present invention, -(Xaa-Yaa-Gly)- as the basic unit may be repeated not less than 5 times, 6 times, 7 times, 8 times, 9 times or 10 times.

In this specification and the sequence tables attached thereto, a peptide structure is expressed by the three-letter or single-letter code of amino acids which is commonly known to those skilled in the art. In this specification, amino acids are in L configuration. The amino acids in this specification include not only the 20 types of L-amino acids that are known to be used to translate general proteins in molecular biology; but also modified amino acid residues that are well known in the technical field of the invention, such as 4-hydroxy-L-proline, 4-fluoro-L-proline and N-isobutyl glycine. In this specification, hydroxyproline is 3-hydroxyproline or 4-hydroxy-L-proline; and is expressed as "Hyp" by the three-letter code, and as "O" by the single-letter code.

As for the collagen-like peptide in this specification, a homotrimer refers to a trimer containing three peptides sharing an identical primary structure. Further, a heterotrimer refers to a trimer containing two peptides sharing an identical primary structure and one peptide whose primary structure differs from those of the two peptides; or a trimer containing three peptides whose primary structures differ from one another.

In this specification, a denaturation temperature refers to a temperature at which a half of the triple-helical structure of the collagen-like peptide described in this specification is turned into a random coil structure. The denaturation temperature is, for example, measured by a known method such as higher order structure analysis conducted by circular dichroic spectrum (CD spectrum) measurement (Patent documents 1 and 2). However, the denaturation temperature may also be measured by another known method, and a method for measuring such denaturation temperature shall not be limited to the method described above.

The collagen-like peptide of the present invention is produced using commercially available amino acids. Other than that, the collagen-like peptide of the invention may also be produced by a known chemical method for synthesizing peptides (Patent document 1). Further, a nucleic acid sequence encoding a desired amino acid sequence is produced, followed by incorporating such nucleic acid sequence into an expression vector to prepare a recombinant expression vector by a known method, and then producing a transfectant by introducing such recombinant expression vector into an appropriate host including, for example, a microorganism such as *Escherichia coli*. By culturing the transfectant prepared using an appropriate medium, recombinant peptide chains are produced. Thus, by collecting the recombinant peptide chains produced from the culture, there can be prepared the recombinant peptide chains used in the present invention (e.g. Patent document 2, EP1014176A2, U.S. Pat. No. 6,992,172, WO2004/85473 and WO2008/103041).

These peptide chains can, for example, be subjected to a separation and purification process using a separation technique such as high-performance liquid chromatography, followed by obtaining the peptide chains thus treated to use them to produce the triple-chain peptide.

Further, these peptide chains may cause self-assembly and thus form the triple-chain peptide having the triple-helical structure in a water solvent at the time of production or purification. Alternatively, the peptide chains chemically synthesized in the above manner and/or peptide chains produced by a genetic engineering technique; or a triple-chain peptide formed by self-assembly can, for example, be dissolved in a solvent such as water of a temperature not lower than the denaturation temperature and then cooled, thereby allowing three peptide chains to cause self-assembly and thus form a peptide trimer having a helical structure. In this way, a collagen-like peptide can be produced (Patent documents 1 and 2).

In the present invention, the collagen-like peptide with multiple cysteine residues incorporated into the peptide chains is produced, followed by, for example, oxidatively cross-linking such collagen-like peptide by, for example, air oxidation or an oxidation agent such as dimethyl sulfoxide (DMSO), thereby obtaining a polymerized peptide in which the collagen-like peptide is cross-linked by disulfide bonds. The polymerized peptide of the collagen-like peptide produced by this method has an improved strength, and is capable of imparting a property of not undergoing denaturation even when heated in an aqueous solution, as compared to known collagen-like peptides.

Other than the abovementioned DMSO, examples of the oxidation agent used when producing the polymerized peptide of the invention include, but are not limited to oxygen, iodine, hydrogen peroxide, sodium bromate, potassium bromate, sodium perborate or potassium perborate.

The formation of cross-linking by the disulfide bonds in the invention can be confirmed by, for example, quantifying the remaining thiol groups with Ellman's reagent after the oxidative cross-linking reaction.

Moreover, by drying the hydrogel made of the polymerized peptide that is produced in the water solvent in the invention, there can be provided the following polymerized peptide thin membrane with a further improved strength.

2. Collagen-Like Peptide Polymer Endowed with or not Endowed with Bioactivity

A motif having a bioactivity is to be incorporated into the above peptide chains; and/or a peptide having a motif having a bioactivity is to be bound to the side chains of the peptide chains, thereby obtaining a polymerized peptide having such bioactivity, a gel containing such polymerized peptide, and a thin membrane containing such polymerized peptide. By selecting the motif to be incorporated into the collagen-like peptide, there can be produced a polymerized peptide having a desired and specific bioactivity, unlike natural collagens. Further, by not incorporating these peptides having bioactivities, there can be produced a collagen-like peptide polymer that is not endowed with a bioactivity.

The polymerized peptide of this embodiment may be described as that having the following structure.

That is, this polymerized peptide is the polymerized peptide described in "1. Polymerized peptide of collagen-like peptide," in which the aforementioned peptide chains are now at least one selected from the group consisting of
(i) a peptide chain containing at least one of the triple helix forming peptidyl group (s) and at least one of the cross-link forming peptidyl group(s);
(ii) a peptide chain containing at least one of the triple helix forming peptidyl group(s), at least one of the cross-link forming peptidyl group(s) and at least one peptidyl group(s) having a motif having a bioactivity; and
(iii) a peptide chain containing at least one of the triple helix forming peptidyl group (s), at least one cross-link forming peptidyl group(s), and at least one peptidyl group(s) having an amino acid residue linking a biologically active motif to a side chain thereof by a linker.

Further, the polymerized peptide of this embodiment may also be described as that having the following structure.

That is, this polymerized peptide is the aforementioned polymerized peptide having an oxidatively cross-linked structural unit of a trimer peptide that is formed of three peptide chains and is represented by the following formula (I).

[Chemical formula 4]

$$-(A_1,A_2,A_3)- \quad (I)$$

[In the formula (I), $A_1$, $A_2$ and $A_3$ may be identical to or different from one another, and independently represent peptide chains expressed by the following formula (II). $A_1$, $A_2$ and $A_3$ form a trimer having a triple-helical structure, and may be cross-linked by disulfide bonds established by the cysteine (Cys) residues contained in each peptide chain. This trimer is polymerized by oxidative cross-linking via disulfide bonds established by Cys residues.

[Chemical formula 5]

$$R_1-(R_2-Z-R_3)_m-R_4 \quad (II)$$

(In the formula (II), $R_1$ and $R_4$ respectively represent an amino-terminus and a carboxy-terminus, and each of $R_1$ and $R_4$ independently represents a peptidyl group containing any 2 to 10 amino acid residues containing at least two Cys residues. Z represents at least one selected from the group consisting of
(i) a peptidyl group only containing a repeating structure whose basic unit is -(Xaa-Yaa-Gly)-;
(ii) a peptidyl group having the repeating structure whose basic unit is -(Xaa-Yaa-Gly)- and a motif having a bioactivity; and
(iii) a peptidyl group having the repeating structure whose basic unit is -(Xaa-Yaa-Gly)-, and a biologically active motif sequence bound, by a linker, to the side chain(s) of at least one amino acid residue contained in such peptide chains.

Each of $R_2$ and $R_3$ independently represents a peptidyl group having a structure continuously repeating -(Xaa-Yaa-Gly)- as a unit.

As for the number of times -(Xaa-Yaa-Gly)- as the basic unit is repeated in the repeating structure, -(Xaa-Yaa-Gly)- as the basic unit is repeated not less than 0 times in each of $R_2$, Z and $R_3$; and not less than 3 times in $R_2$, Z and $R_3$ in total. m represents an integer of not smaller than 1.)]

In this specification, a "motif" refers to a small structural part found in amino acid sequences of various proteins. It is an amino acid sequence that is locally and significantly well preserved in natural proteins, and serves as a motif amino acid sequence associated with the expression of functions in these proteins. Such "motif" may also be referred to as a "motif sequence" or "sequence motif."

Next, there are described separately a polymerized peptide that is not endowed with a specific bioactivity; and a polymerized peptide endowed with a specific bioactivity.

(1) Polymerized Peptide of Collagen-Like Peptide not Endowed with Specific Bioactivity One embodiment of the present invention is the polymer of the abovementioned collagen-like peptide, which is a polymerized peptide not endowed with a specific bioactivity. Such polymerized peptide that is not endowed with a specific bioactivity contains a repeating sequence whose basic unit is -(Xaa-Yaa-Gly)-; and peptide chains formed of peptidyl groups containing multiple Cys residues. Three of these peptide chains form a collagen-like peptide having a triple-helical structure, and the polymerized peptide not endowed with a specific bioactivity is a polymerized peptide in which such collagen-like peptide is polymerized via cross-linking by disulfide bonds. Specifically, the polymerized peptide not endowed with a specific bioactivity has the following construction.

That is, the polymerized peptide not endowed with a specific bioactivity is a polymerized peptide having the construction described in "1. Polymerized peptide of collagen-like peptide," in which the aforementioned peptide chains are now each containing at least one triple helix forming peptidyl group described above and at least one cross-link forming peptidyl group.

The collagen-like peptide composing the polymerized peptide of this invention may be either a homotrimer or a heterotrimer.

Since a gel containing the polymerized peptide of the invention does not impart a specific bioactivity, the polymerized peptide thin membrane can, for example, be used as a medical material for adhesion prevention of organs and as a suture material.

If using the gel or polymerized peptide thin membrane containing the polymerized peptide of the invention as a medical material for adhesion prevention of organs, such medical material may, for example, be placed between an organ and the dermis, or between an organ and another organ, in a surgery, thereby preventing an organ from adhering to the dermis and another organ. The medical material of the invention thus placed may gradually become soluble and degraded, and then disappear, by peptidase and phagocytes such as macrophage that are present in vivo. Therefore, no further surgery is required to remove such medical material, thus imposing a smaller burden on the prognosis of a patient, and making it possible to improve QOL (Quality of life).

Further, since the medical material of the present invention is an artificially produced collagen-like peptide, it differs from natural collagens in that the risk of viral or microbial infection is low. Furthermore, since the medical material of the invention is cross-linked by disulfide bonds and thus shall not undergo denaturation even when subjected to a heating treatment, it can, for example, be heated for the purpose of sterilization.

(2) Polymerized Peptide of Collagen-Like Peptide Containing Peptide Chain Incorporating Biologically Active Motif A motif having a bioactivity is to be incorporated into the abovementioned peptide chains, or linked to the side chain of the abovementioned single chain by a linker, thereby obtaining a polymerized peptide of a collagen-like peptide that has a desired bioactivity whose intensity is controlled and/or multiple bioactivities combined.

(1) Polymer of Collagen-Like Peptide with Biologically Active Motif Incorporated into Peptide Chain A polymer of a collagen-like peptide incorporating a biologically active motif has the following construction.

The polymer of a collagen-like peptide incorporating a biologically active motif is a polymerized peptide having the construction described in "1. Polymerized peptide of collagen-like peptide," in which the aforementioned peptide chains are now peptide chains containing at least one triple helix forming peptidyl group described above, at least one cross-link forming peptidyl group, and at least one peptidyl group having a motif having a bioactivity.

In the abovementioned polymerized peptide, the peptide chains may each be expressed by the following formula (III).
[Chemical formula 6] (SEQ ID NO: 39 disclosed below)

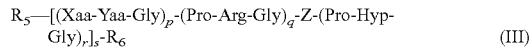

[In the formula (III), $R_5$ and $R_6$ respectively represent an amino-terminus and a carboxy-terminus, and each independently represents a peptidyl group containing any 2 to 10 amino acid residues containing at least two Cys residues. Each of p, q and r represents an integer of not smaller than 0, and a sum total of p, q and r is not smaller than 3. s represents an integer of not smaller than 11

The collagen-like peptide composing the polymerized peptide of this invention may be either a homotrimer or a heterotrimer.

In the invention of the aforementioned polymerized peptide, the bioactivity may be a binding activity specific to a biopolymer. In this specification, a "biopolymer" refers to a protein, polypeptide, peptide, nucleic acid and fragments thereof which are contained in mammals such as human. As a binding activity specific to a biopolymer, examples thereof include, but are not limited to an adhesion or binding activity of various cells to collagen receptors, and an adhesion or binding activity of various cells to fibronectin. As a binding activity specific to a biopolymer, there has been known a particular motif contained in a ligand capable of selectively binding to various receptors present in cell membranes.

As a motif, a binding motif related to a collagen receptor selected from integrins, discoidin domain receptors (DDRs) or heparan sulfate proteoglycans (HSPGs) is, for example, to be incorporated at the time of producing peptide chains, thereby allowing such binding motif to be endowed with a receptor-selective cell adhesion having a selective binding activity, thus making it possible to provide a material for research or a medical material.

Examples of motifs other than the above motif include, but are not limited to a VWF-binding motif, a SPARC/BM-40/osteonectin-binding motif, an aegyptin-binding motif, a LAIR-1-binding motif, a GPVI-binding motif, a PEDF-binding motif, an Hsp47-binding motif, an HLA motif, an HLA super motif, a zinc finger C2H2 type motif, a cytochrome b (amino-terminus)/b6/pet B motif, an immunoglobulin domain motif, a WD domain G-β repeat motif, a PDZ domain motif, a leucine-rich repeat motif, a protein kinase domain motif, a PH domain motif, an EGF-like domain motif, a reverse transcriptase (RNA-dependent DNA polymerase) motif, an Ank repeat motif, a NADH-ubiquinone/plastoquinone (complex I) motif, an EF-hand motif, a retroviral aspartyl protease motif and a seven-transmembrane receptor (rhodopsin family) motif.

Further, specific examples of a cell-adhesion motif include RGD sequence, LDV sequence, REDV sequence (SEQ ID NO: 29), YIGSR sequence (SEQ ID NO: 30), PDSGR sequence (SEQ ID NO: 31), RYVVLPR sequence (SEQ ID NO: 32), LGTIPG sequence (SEQ ID NO: 33), RNIAEIIKDI sequence (SEQ ID NO: 34), IKVAV sequence (SEQ ID NO: 35), LRE sequence, DGEA sequence (SEQ ID NO: 36) and HAV sequence.

When endowing a selective cellular adhesion as a specific bioactivity to the polymerized peptide of the invention, cells as the targets of such bioactivity are cells having receptors capable of binding to the above motif as a binding ligand, specific examples of which include fibroblasts, hepatocytes, undifferentiated chondrocytes, myocytes, platelets, neutrophils, macrophages, Schwann cells, keratinocytes or epithelial cells.

Further, as a motif other than the aforementioned motifs, there may also be employed, for example, motifs found on PROSITE (http://www.expasy.ch/prosite/) and PRINTS (http://bioinf.man.ac.uk/dbbrowser/PRINTS/PRINTS.html).

A binding motif related to the above integrin may be, but is not limited to -Gly-Phe-Hyp-Gly-Glu-Arg- (SEQ ID NO: 26); a binding motif related to the discoidin domain receptor may be, but is not limited to -Gly-Val-Met-Gly-Phe-Hyp- (SEQ ID NO: 27); and a binding motif related to the heparan sulfate proteoglycan may be, but is not limited to -Lys-Gly-His-Arg-Gly-Phe-(SEQ ID NO: 28).

Further, when using the polymerized peptide of the invention as a research base material having a desired selective activity, it can be used in, for example, researches for unraveling the mechanism of the intracellular information transmission system of the cells that are to bind to such base material.

Furthermore, if used as a medical material, the gel or polymerized peptide thin membrane containing the polymerized peptide of the invention can, for example, be placed on a region of wound, a surgical incision made in a surgery, the cornea and the retina. As a result of allowing receptors present on the cell membranes of the fibroblasts to incorporate the aforementioned binding motifs having binding activities, the gel or polymerized peptide thin membrane can, for example, be used as a medical material for promoting wound healing for enhancing the migration and binding of the fibroblasts to a region of wound or a surgical incision, and thus promoting the healing of a wound or surgical incision; or as a medical material for use in cornea and retina regeneration.

(2) Polymer of Collagen-Like Peptide with Biologically Active Motif Linked to Side Chain of Peptide Chain by Linker A polymer of a collagen-like peptide with a biologically active motif linked to the side chains of peptide chains via a linker has the following construction.

The polymer of such collagen-like peptide is a polymerized peptide having the construction described in "1. Polymerized peptide of collagen-like peptide," in which the aforementioned peptide chains may each be a peptidyl group having a repeating structure whose basic unit is -(Xaa-Yaa-Gly)-, and a biologically active motif linked to the side chain(s) of at least one amino acid residues contained in this peptide chain via a linker.

In the invention of the above polymerized peptide, the peptide chains may each be represented by the following formula (III).

[Chemical formula 7] (SEQ ID NO: 39 disclosed below)

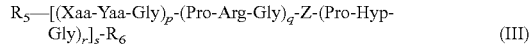

$R_5$—[(Xaa-Yaa-Gly)$_p$-(Pro-Arg-Gly)$_q$-Z-(Pro-Hyp-Gly)$_r$]$_s$-$R_6$ (III)

[In the formula (III), $R_5$ and $R_6$ respectively represent an amino-terminus and a carboxy-terminus, and each independently represents a peptidyl group containing any 2 to 10 amino acid residues containing at least two Cys residues. Each of p, q and r represents an integer of not smaller than 0, and a sum total of p, q and r is not smaller than 3. s represents an integer of not smaller than 11

The collagen peptide composing the polymerized peptide of this invention may be either a homotrimer or a heterotrimer.

In the invention of the above polymerized peptide, the bioactivity may be a binding activity specific to a biopolymer.

In this invention, as the abovementioned motif, a binding motif related to integrin of fibronectin is, for example, to be incorporated or bound at the time of producing the peptide chains or after producing the polymerized peptide, thereby making it possible to provide a material for research or medical material in which the motif has been endowed with a receptor-selective cellular adhesion having a selective binding activity.

A binding motif related to a fibronectin-derived integrin αvβ3 may be, but is not limited to -Arg-Gly-Asp-.

Examples of motifs other than the above motif include, but are not limited to a VWF-binding motif, a SPARC/BM-40/osteonectin-binding motif, an aegyptin-binding motif, a LAIR-1-binding motif, a GPVI-binding motif, a PEDF-binding motif, an Hsp47-binding motif, an HLA motif, an HLA super motif, a zinc finger C2H2 type motif, a cytochrome b (amino-terminus)/b6/pet B motif, an immunoglobulin domain motif, a WD domain G-β repeat motif, a PDZ domain motif, a leucine-rich repeat motif, a protein kinase domain motif, a PH domain motif, an EGF-like domain motif, a reverse transcriptase (RNA-dependent DNA polymerase) motif, an Ank repeat motif, a NADH-ubiquinone/plastoquinone (complex I) motif, an EF-hand motif, a retroviral aspartyl protease motif and a seven-transmembrane receptor (rhodopsin family) motif.

Further, specific examples of a cell-adhesion motif include RGD sequence, LDV sequence, REDV sequence (SEQ ID NO: 29), YIGSR sequence (SEQ ID NO: 30), PDSGR sequence (SEQ ID NO: 31), RYVVLPR sequence (SEQ ID NO: 32), LGTIPG sequence (SEQ ID NO: 33), RNIAEIIKDI sequence (SEQ ID NO: 34), IKVAV sequence (SEQ ID NO: 35), LRE sequence, DGEA sequence (SEQ ID NO: 36) and HAV sequence.

When endowing a selective cellular adhesion as a specific bioactivity to the polymerized peptide of the invention, cells as the targets of such bioactivity are cells having receptors capable of binding to the above motif as a binding ligand, specific examples of which include, but are not limited to fibroblasts, hepatocytes, undifferentiated chondrocytes, myocytes, platelets, neutrophils, macrophages, Schwann cells, keratinocytes and epithelial cells.

Further, as a motif other than the aforementioned motifs, there may also be employed, for example, motifs found on PROSITE (http://www.expasy.ch/prosite/) and PRINTS (http://bioinf.man.ac.uk/dbbrowser/PRINTS/PRINTS.html).

When used as a research material having a desired selective activity, the polymerized peptide can, for example, be used to unravel the mechanism of the intracellular information transmission system of the cells that are to adhere to such material.

Furthermore, if used as a medical material, the gel or polymerized peptide thin membrane containing the polymerized peptide of the invention can, for example, be left on a region of wound or a surgical incision made in a surgery. As a result of allowing receptors present on the cell membranes of the fibroblasts to incorporate binding motifs having binding activities, the gel or polymerized peptide thin membrane can, for example, be used as a medical material for promoting wound healing for enhancing the migration and binding of the fibroblasts to a region of wound or a surgical incision, and thus promoting the healing of a wound or surgical incision.

(3) Polymerized Peptide Incorporating Multiple Kinds of Biologically Active Motifs; or with Multiple Kinds of Biologically Active Motifs Bound Thereto As an embodiment of the present invention, by combining peptide chains incorporating the above biologically active motifs and/or peptide chains with the above biologically active motifs linked thereto, there can be prepared a polymerized peptide having selectively combined activities whose intensities have been respectively adjusted to desired levels.

This polymerized peptide having such combined activities i.e. a polymerized peptide having a desired activity or activities can be prepared by mixing collagen-like peptides with different types of activities at an adjusted mixing ratio such that a desired activity or activities may be exhibited, and then polymerizing them by oxidative cross-linking. Using this polymerized peptide, there can be produced, by the abovementioned production method, a gel and polymerized peptide thin membrane containing such polymerized peptide.

In this embodiment, examples of biologically active motifs that are to be used in combination include, but are not limited to a binding motif related to integrins, a binding motif related to discoidin-domain receptors, a binding motif related to heparan sulfates and an RGD motif.

As for these motifs, a binding motif(s) related to a collagen receptor selected from integrins, discoidin domain receptors (DDRs) or heparan sulfate proteoglycans (HSPGs); or an RGD motif of fibronectin are, for example, to be incorporated at the time of producing the peptide chains or after producing the polymerized peptide, thereby making it possible to provide a research material or medical material in which such binding motif(s) have been each endowed with a receptor-selective cell adhesion having a selective binding activity.

Examples of motifs other than the above motif include, but are not limited to a VWF-binding motif, a SPARC/BM-40/osteonectin-binding motif, an aegyptin-binding motif, a LAIR-1-binding motif, a GPVI-binding motif, a PEDF-binding motif, an Hsp47-binding motif, an HLA motif, an HLA super motif, a zinc finger C2H2 type motif, a cytochrome b (amino-terminus)/b6/pet B motif, an immunoglobulin domain motif, a WD domain G-β repeat motif, a PDZ domain motif, a leucine-rich repeat motif, a protein kinase domain motif, a PH domain motif, an EGF-like domain motif, a reverse transcriptase (RNA-dependent DNA polymerase) motif, an Ank repeat motif, a NADH-ubiquinone/plastoquinone (complex I) motif, an EF-hand motif, a retroviral aspartyl protease motif and a seven-transmembrane receptor (rhodopsin family) motif.

Further, specific examples of a cell-adhesion motif include RGD sequence, LDV sequence, REDV sequence (SEQ ID NO: 29), YIGSR sequence (SEQ ID NO: 30), PDSGR sequence (SEQ ID NO: 31), RYVVLPR sequence (SEQ ID NO: 32), LGTIPG sequence (SEQ ID NO: 33), RNIAEIIKDI sequence (SEQ ID NO: 34), IKVAV sequence (SEQ ID NO: 35), LRE sequence, DGEA sequence (SEQ ID NO: 36) and HAV sequence.

When endowing a selective cell adhesion as a specific bioactivity to the polymerized peptide of the invention, cells as the targets of such bioactivity are cells having receptors capable of binding to the above motif as a binding ligand, specific examples of which include, but are not limited to fibroblasts, hepatocytes, undifferentiated chondrocytes, myocytes, platelets, neutrophils, macrophages, Schwann cells, keratinocytes and epithelial cells.

Further, as a motif other than the aforementioned motifs, there may also be employed, for example, motifs found on PROSITE (http://www.expasy.ch/prosite/) and PRINTS (http://bioinf.man.ac.uk/dbbrowser/PRINTS/PRINTS.html).

3. Gelling Agent, Gel, Hydrogel and Polymerized Peptide Thin Membrane Containing Polymerized Peptide of Collagen-Like Peptide of the Invention If produced in a water solvent, the abovementioned polymerized peptide is thus produced as a hydrogel of the polymerized peptide of the invention and water i.e. the polymerized peptide of the invention can be employed as a gelling agent.

Further, the hydrogel of the invention can be used as a postsurgical adhesion prevention agent for organs, a hemostatic agent, an agent for promoting wound healing, and a regenerative medical material such as a material for cornea or retina regeneration.

In addition, by drying the above hydrogel, there can be prepared a polymerized peptide thin membrane as a sheet-shaped membrane. This polymerized peptide thin membrane can, for example, be rehydrated at the time of use so that it can be used as the above material for promoting wound healing, and a regenerative medical material such as an artificial cornea and a cell sheet for an artificial myocardial membrane capable of being transplanted into a body.

As compared to the undried hydrogel made of the polymerized peptide, the polymerized peptide thin membrane of the invention can be stored for a longer period of time under room temperature since it is dry, and can be endowed with a strength higher than that of the original hydrogel even after the interaction between the peptide molecules has changed and the polymerized peptide thin membrane has been rehydrated. That is, the polymerized peptide thin membrane of the invention has an improved strength, and can be used as a heat-resistant medical material capable of being subjected to heat sterilization.

The gel of the present invention may be produced as follows. That is, the aforementioned triple-chain peptide forms the triple-helical structure as a heterotrimer, followed by using an oxidant to oxidatively polymerize, then there can be prepared a gel containing at least one kind of peptide chain. Also, the aforementioned triple-chain peptide may form the triple-helical structure as a homotrimer instead, followed by mixing multiple kinds of homotrimers, and then using an oxidant to oxidatively polymerize, then there can be prepared a gel containing at least one kind of peptide chain.

The production of the above gel prepared by polymerizing multiple kinds of homotrimers by cross-linking is described in greater detail. Multiple kinds of triple-chain peptides may be mixed with the abovementioned triple-chain peptide as a polymerization unit, followed by using an oxidant agent to cross-link, polymerize, a gelling reaction was caused, and thus a gel is produced.

With regard to such gel containing multiple kinds of triple-chain peptides, the tolerability (stiffness) of the gel can, for example, be controlled and/or the expression of bioactivities can, for example, be adjusted, by combining a triple-chain peptide contained in peptide chains for controlling the stiffness of the gel; and a triple-chain peptide contained in peptide chains having biologically active motifs.

In this specification, the "stiffness (stiffness) of the gel" refers to, for example, a tolerability of the gel against degradation by phagocytes such as macrophages in vivo. This stiffness of the gel is affected by, for example, the degree of cross-linking polymerization of the gel, and differences in the branched structures of the peptide chains. For example, a stiff gel may be formed when the cross-links established by the disulfide bonds are contained in the gel by a large quantity.

As a single-chain peptide used in the multiple kinds of triple-chain peptides, there can be listed, for example, peptide chains with different numbers of the cysteine residues contained in the single-chain peptide, for the purpose of controlling the stiffness of the gel. For example, a peptide chain having three cysteines at each of its amino-terminus side and carboxy-terminus side or in the corresponding vicinities of these sides; a peptide chain having two cysteines at each of its amino-terminus side and carboxy-terminus side or in the corresponding vicinities of these sides; and a peptide chain having one cysteine at each of its amino-terminus side and carboxy-terminus side or in the corresponding vicinities of these sides may be combined together, followed by heating and then gradually cooling each peptide chain to form a triple-chain peptide having a triple-helical structure containing these peptide chains. These triple-chain peptides are then mixed together at a given ratio, followed by using an oxidant to cross-link, polymerize and thus a gel containing a multifunctional polymerized peptide can be produced and used.

A gel of a polymerized peptide prepared by employing a high percentage of a peptide(s) containing a large number of cysteine residues tends to exhibit a slow biodegradability in vivo, whereas a gel containing a polymerized peptide prepared by employing a high percentage of a peptide(s) with a small number of cysteine residues exhibits a faster biodegradability.

Further, it is assumed that by using a gel prepared by combining peptides with different numbers of cysteine residues, the intensity of activity expression of the biologically active motifs contained in the peptide chains can be adjusted i.e. by adjusting the degree of cross-linking in the gel, the stiffness of the gel of the invention and the intensity of the expression of the bioactivities can be controlled.

For example, in the case of the gel of the present invention, a peptide chain having three cysteine residues, two cysteine residues or one cysteine residue in the vicinity of each of the amino-terminus and carboxy-terminus; a peptide chain having three cysteine residues at each of the two termini; and a peptide chain having two cysteine residues or one cysteine residue at each of the two termini may be combined together. Here, the gel produced can be used as a medical material, if it contains the peptide chain having two cysteine residues at each of the two termini at a compounding ratio of not higher than 10% by mass, or the peptide chain having one cysteine residue at each of the two termini at a compounding ratio of lower than 70% by mass, preferably not higher than 50% by mass.

Further, for example, if combining the peptide chain having two cysteine residues in the vicinity of each of the amino-terminus and carboxy-terminus; and the peptide chain having one cysteine residue in the vicinity of each of the amino-terminus and carboxy-terminus, there can be produced a usable gel if the gel contains the peptide chain having one cysteine residue at each terminus at a compounding ratio of lower than 30% by mass, preferably not higher than 10% by mass. As for these peptide chains, those having no cysteine residue and those having cysteine residues can also be used in combination.

Examples of the peptide chain having three cysteine residues, two cysteine residues or one cysteine residue in the vicinity of each of the amino-terminus and carboxy-terminus include CCC2-GPOGGPR (short) (SEQ ID NO. 15), CC2-GPOGPR (short) (SEQ. ID No. 23) and C2-GPOGPR (short) (SEQ ID NO. 24).

Further, examples of the peptide chain having no cysteine residue include Soluble GFOGER (SEQ ID NO. 19), Soluble GVMGFO (SEQ ID NO. 20), Soluble KGHRGF (SEQ ID NO. 21) and Soluble GPOGPR (short) (SEQ ID NO. 25).

In addition, a triple-chain peptide containing peptide chains having biologically active motifs is to be combined and mixed with the combination of the triple-chain peptides each containing the peptide chains capable of controlling the stiffness of the gel, for the purpose of forming a polymerized peptide using the aforementioned method. Thus, there can be produced a multifunctional polymerized peptide capable of controlling the stiffness of the gel in vivo; and the kinds of bioactivities as wells as the intensities of their expression. Moreover, by adjusting the stiffness of this polymerized peptide and/or the kinds and amounts of motifs which express in a biological body, the biodegradation rate after transplanting the gel into a biological body can, for example, be adjusted or controlled.

Therefore, in accordance with desired purposes of the gel of the present invention, there can be produced a gel containing a polymerized peptide employing various kinds of peptide chains. That is, for example, a gel employing a large amount of peptides containing a large number of cysteine residues is produced for use in a material of an artificial organ which is better off without being subjected to biodegradation, the examples of such artificial organ including artificial blood vessels or the like. Meanwhile, for example, a gel containing the polymerized peptide of the invention with fewer cysteine residues employed therein is produced for use in a material which is better off if subjected to biodegradation after remaining in vivo for a given period of time, the examples of such material including a postsurgical adhesion prevention agent for organs and an agent for promoting wound healing.

4. Medical Material for Regeneration Containing Polymerized Peptide of Collagen-Like Peptide of the Invention As described above, with the polymerized peptide of the invention, there can be produced a gel, hydrogel or polymerized peptide thin membrane having a specific bioactivity or bioactivities by incorporating a motif(s) having a desired bioactivity or bioactivities, or by linking it via a linker. Alternatively, by not incorporating or binding a biologically active motif(s), there can be produced a gel, hydrogel or polymerized peptide thin membrane having no specific bioactivity i.e. exhibiting a low stimulus in vivo and having a high safety.

As for the gel, hydrogel or polymerized peptide thin membrane containing the polymerized peptide of the invention, the polymerized peptide endowed with a specific bioactivity or bioactivities can, for example, be prepared by incorporating into the peptide chains or binding to the peptide chains the binding motifs related to the above collagen receptors, thereby making it possible to endow such gel, hydrogel or polymerized peptide thin membrane with a binding activity or activities that are selectively bound to cells having related collagen receptors.

Cells having selective binding activities may be accumulated with these hydrogel or polymerized peptide thin membrane being used as a scaffold material. Here, due to, for example, the activities of the cytokine and chemokine released by these cells, a bioactivity such as an effect for promoting wound healing can, for example, be imparted to the tissue and/or cells around a site where the hydrogel or polymerized peptide thin membrane has been placed.

Here, for example, the gel, hydrogel or polymerized peptide thin membrane may be used as a medical material having a high selectivity to platelets, fibroblasts and/or corneal cells, preferably as a regenerative medical material, more preferably as a regenerative medical material for wound healing promotion. It is expected that platelets and/or fibroblasts may selectively bind to the medical material of the invention as a scaffold material, and that cytokine and/or chemokine may thus be released from these cells, thereby contributing to tissue regeneration such as wound healing.

Examples of a binding motif include a binding motif related to a collagen receptor selected from integrin, discoidin domain receptor (DDR) or heparan sulfate proteoglycan (HSPG); or a binding motif related to fibronectin-derived integrin αvβ3.

More specific examples of such motif include, but are not limited to -Gly-Phe-Hyp-Gly-Glu-Arg- (SEQ ID NO: 26) as a binding motif related to integrins; -Gly-Val-Met-Gly-Phe-Hyp- (SEQ ID NO: 27) as a binding motif related to discoidin domain receptors; -Lys-Gly-His-Arg-Gly-Phe- (SEQ ID NO: 28) as a binding motif amino acid sequence related heparan sulfate proteoglycans; and -Arg-Gly-Asp- as a binding motif related to fibronectin-derived integrin αvβ3.

EXAMPLE

Abbreviations used in examples are as follows.
Amino acid residues (all are L forms)
Arg (R): Arginine
Asp (D): Aspartic acid
Cys (C): Cysteine
Gln (Q): Glutamine
Gln (E): Glutamic acid
Gly (G): Glycine
His (H): Histidine
Hyp (O): 4-hydroxyproline
Lys (K): Lysine
Pro (P): Proline
Tyr (Y): Tyrosine
Ile (I): Isoleucine
Leu (L): Leucine
Met (M): Methionine
Phe (F): Phenylalanine
Ser (S): Serine
Val (V): Valine
Protective Groups
Fmoc: 9-fluorenylmethoxycarbonyl
tBu: test-butyl
Trt: Triphenyl methyl (trityl)
Pbf: 2,2,4,6,7-pentamethyldihydrobenzofuran-5-sulfonyl
Boc: tert-butoxycarbonyl
Resin
CTC: 2-chlorotrityl chloride
Reagents
BCA: Bicinchoninic acid
BSA: Bovine serum albumin
CHCA: α-cyano-4-hydroxycinnamate
DCM: Dichloromethane
DIC: N, N'-diisopropylcarbodiimide
DIEA: N,N-diisopropylethylamine
DMAP: N,N-dimethylaminopyridine
DMF: N,N-dimethylformamide
DMSO: Dimethylsulfoxide
DTNB: 5,5'-dithiobis-2-nitrobenzoic acid
DTT: Dithiothreitol
EDT: Ethanedithiol
EDTA: Ethylenediamine tetraacetic acid
FBS: Fetal bovine serum
HOBt: 1-hydroxybenzotriazole
MeCN: Acetonitrile
MeOH: Methanol
MOPS: 3-morpholinopropane sulfonic acid
NEM: N-ethylmaleimide
PBS: Phosphate buffered saline
PMSF: Phenylmethylsulfonylfluoride
SDS: Sodium dodecyl sulfate
TBS: Tris buffered saline
TFA: Trifluoroacetic acid
TMSO: Tetramethylene sulfoxide
Apparatus
RP-HPLC: Reversed-phase high performance liquid chromatography
MALDI-TOF MS: Matrix-assisted laser desorption/ionization time-of-flight mass spectrometer
Others
CD: Circular dichroism
DDR: Discoidin domain receptor
ECM: Extracellular matrix
FAK: Focal adhesion kinase (focal adhesion kinase)
HDF: Human dermal fibroblasts
HRP: Horseradish peroxidase
HSPG: Heparan sulfate proteoglycan
PEDF: Pigment epithelium-derived factor
SDS-PAGE: Sodium dodecyl sulfate-polyacrylamide gel electrophoresis
vWF: von Willebrand factor The examples of the invention that are described below are simply provided as examples, and shall not limit the technical scope of the present invention. The technical scope of the present invention is only limited by the descriptions in the scope of claims. The present invention may be modified, for example, elements may be added to the present invention, and the elements of the invention may also be deleted or even substituted without departing from the gist of the present invention.

Example 1

<Production of Single-Chain Peptide>
Materials and Methods
Peptide Synthesis
In this example, the peptides of the SEQ ID NOS. 1 to 22 listed in the following Table 1 were synthesized by solid-phase synthesis method, and then used.

TABLE 1

| Seq ID No | Abbreviation | Amino acid sequence |
|---|---|---|
| 1 | YCC2 | YCC(POG)$_6$PRG(POG)$_5$CCY |
| 2 | CC2 | CC(POG)$_6$PRG(POG)$_5$CC |
| 3 | CC1 | (POG)$_6$PRG(POG)$_5$CC |

TABLE 1-continued

| Seq ID No | Abbreviation | Amino acid sequence |
|---|---|---|
| 4 | C2 | C(POG)$_6$PRG(POG)$_5$C |
| 5 | CCC2 | CCC(POG)$_6$PRG(POG)$_5$CCC |
| 6 | GGGCCC | CCCGGG(POG)$_5$FOGERG(POG)$_5$GGGCCC |
| 7 | CCCC2 | CCCC(POG)$_6$PRG(POG)$_5$CCGC |
| 8 | Y2 | Y(POG)$_6$PRG(POG)$_5$Y |
| 9 | YCC2-Scr | YCCGPPOGGOPOGPPOGGOPOGRPOGPPOGGOPOGCCY |
| 10 | CCC2-GPOGPR (short) | CCC(POG)$_5$PRG(POG)$_4$CCC |
| 11 | CCC2-GFOGER (short) | CCC(POG)$_4$FOGERG(POG)$_4$CCC |
| 12 | YCC2-GFOGER | YCC(POG)$_5$FOGERG(POG)$_5$CCY |
| 13 | YCC2-GVMGFO | YCC(POG)$_5$PRGQOGVMGFOG(POG)$_5$CCY |
| 14 | YCC2-KGHRGF | YCC(POG)$_7$PKGHRGFSGLOG(POG)$_6$CCY |
| 15 | CCC2-GPOGPR | CCC(POG)$_7$PRG(POG)$_6$CCC |
| 16 | CCC2-GEOGER | CCC(POG)$_6$FOGERG(POG)$_6$CCC |
| 17 | CCC2-GVMGFO | CCC(POG)$_5$PRGOOGVMGFOG(POG)$_5$CCC |
| 18 | CCC2-KGHRGF | CCC(POG)$_5$PKGHRGESGLOG(POG)$_5$CCC |
| 19 | Soluble GFOGER | Ac-G(POG)$_4$FOGERG(POG)$_5$-NH$_2$ |
| 20 | Soluble GVMGFO | G(POG)$_4$PRGQOGVMGFOG(POG)$_4$-NH$_2$ |
| 21 | Soluble KGHRGF | G(POG)$_7$IKGHRGFSGLOG(POG)$_6$-NH$_2$ |
| 22 | RGD pep | GRGDS-NH$_2$ |
| 23 | CC2-GPOGPR (short) | CC(POG)$_5$PRG(POG)$_4$CC |
| 24 | C2-GPOGPR (short) | G(POG)$_5$PRG(POG)$_4$C |
| 25 | Soluble GPOGPR (short) | βA(POG)$_4$PRG(POG)$_5$ |

In Table 1, amino acid sequences are each expressed with single-letter code which is commonly used by those skilled in the art. However, "O" represents a 4-hydroxyproline residue, "Ac-" represents an acetylated amino terminus, "—NH$_2$" represents an amidated carboxy-terminus, and "βA" represents a β-alanine residue.

The peptide chain has a repeating sequence in which -(Xaa-Yaa-Gly)- as a basic unit for forming a triple-helical structure is repeated 10 to 17 times. Polymerization was designed in a way such that Cys residues were to be incorporated into both the amino and carboxy terminiof this basic sequence or into the vicinities thereof, and that a disulfide cross-linking (—S—S—) was to be formed by the oxidation of the thiol group (—SH) of the side chain. In Table 1, GFOGER (SEQ ID NO: 26) of the SEQ ID NOS. 12, 16 and 19, GVMGFO (SEQ ID NO: 27) of the SEQ ID NOS. 13, 17 and 20, and KGHRGF (SEQ ID NO: 28) of the SEQ ID NOS. 14, 18 and 21, respectively represent collagen binding motifs of integrins, discoidin domain receptors (DDRs), and heparan sulfate proteoglycans (HSPGs). Here, RGQOGVMGFO (SEQ ID NO: 37) and KGHRGFSGL (SEQ ID NO: 38) respectively represent binding motifs of vWF and PEDF. Further, there were designed Y2 (SEQ ID NO: 8) having no Cys residue, and YCC2-Scr (SEQ ID NO: 9) considered to have a random coil structure due to the absence of a repeating sequence of (Pro-Hyp-Gly).

Fmoc-amino acids which are Fmoc-Arg(Pbf)-OH, Fmoc-Cys(Trt)-OH, Fmoc-Gly-OH, Fmoc-Pro-OH and Fmoc-Tyr(tBu)-OH were purchased from Novabiochem (Merck Millipore Corporation, USA). Further, Wang resin was also purchased from Novabiochem. Other reagents used were of a grade as high as or higher than those ranked as special in the market. CTC resin was purchased from PEPTIDE INSTITUTE, INC. (Osaka). Ellman's reagent was prepared in a way such that DTNB was dissolved to a concentration of 9 mg/ml in 50 mM of a phosphate buffer solution (pH 8.4).

Apparatus and Device Used in Experiment

PD-10 empty column (GE Healthcare, USA) or Libra Tube (HiPep Laboratories, Kyoto) was used for solid-phase synthesis. Peptide was analyzed by HPLC C20A series (Shimadzu Corporation, Kyoto), and COSMOSIL 5C18 AR-II (NACALAI TESQUE, INC) was used as a column. Peptide was purified by LC 2000 Plus series (JASCO Corporation, Tokyo), and COSMOSIL 5C18 AR-II (NACALAI TESQUE, INC) or Cadenza CD-C18 (Imtakt Corporation, Kyoto) was used as a column. Peptide mass spectrometry was measured by Autoflex-III (Bruker Corporation, Germany). CD spectrum of peptide was measured by a circular dichroism spectrometer J-820 (JASCO Corporation). UV absorbance of Fmoc group was measured using an ultraviolet and visible spectrophotometer V-630 (JASCO Corporation). Temperature for peptide refolding was controlled by TaKaRa Thermal Cycler (TAKARA BIO INC., Shiga). Gel formation was determined using a stainless ball (diameter 1.5 mm, Funabe Co., Ltd., Hyogo). The cell-culturing dishes used were Nunc Cell-Culture/Petri Dishes (9 cm dish), Nunc MicroWell 96-Well Microplates (96 well plate) and Nunc Cell-Culture Treated Multidishes (6 well plate) (Thermo Fisher Scientific, Inc., USA). Cell was observed by a laser scanning confocal microscope FV1000, (Olympus Corporation, Tokyo). Visualization of Western blotting was performed using LAS-3000 (FUJIMEMBRANE Corporation, Tokyo).

Preparation of Peptide Chain by Solid-Phase Synthesis

Peptide was synthesized by an Fmoc-based method (publication of JP-A-2005-263784) which is commonly employed by those skilled in the art.

Purification of Peptide by RP-HPLC

Peptide was purified by RP-HPLC (LC 2000 Plus series, JASCO Corporation), with linear concentration gradients for elution of 0.05% (v/v) TFA-$H_2O$ and 0.05% (v/v) TFA-MeCN. A column i.d. was set to be 20 mm, a column temperature was set to be 60° C., a flow rate was set to be 5 ml/min, and a detection wavelength was set to be 220 nm. The column used was either COSMOSIL 5C18 AR-II (NACALAI TESQUE, INC) or Cadenza CD-C18 (Imtakt Corporation).

Purity Analysis of Peptide by RP-HPLC and Result Thereof

After purifying the peptide synthesized, RP-HPLC was employed to confirm the purity thereof. The peptide was eluted in a mobile phase with linear concentration gradients employing 0.05% TFA/$H_2O$ and 0.05% TFA/MeCN, and a concentration gradient when analyzing Soluble KGHRGF (SEQ ID NO: 21) was set to be 0.05% TFA/MeCN 0 to 30%/30 min, 30 to 90%/5 min, whereas a concentration gradient when analyzing other peptides was set to be 0.05% TFA/MeCN 10 to 40%/30 min, 40 to 90%/5 min. Further, a column temperature was set to be 60° C., and a measurement wavelength was set to be 220 nm.

FIG. 2A to FIG. 2D show results obtained after subjecting each peptide of YCC2 (SEQ ID NO: 1), CC2 (SEQ ID NO: 2), CC1 (SEQ ID NO: 3) and C2 (SEQ ID NO: 4) to the RP-HPLC analysis (results of RP-HPLC analysis of other peptides are now shown). In addition, the retention time of each peptide is shown in Table 2.

TABLE 2

(The below described "Peptide names" references SEQ ID NOS 1-5, 7, 9, 8, 12-14, 19-21, 10-11, 15-18 and 23-25, respectively, in order of appearance)

| Peptide name | Retention time (min) |
|---|---|
| YCC2 | 15.8 |
| CC2 | 13.3 |
| CC1 | 12.9 |
| C2 | 12.7 |
| CCC2 | 14.7 |
| CCCC2 | 15.8 |
| YCC2-Scr | 14.4 |
| Y2 | 13.7 |
| YCC2-GFOGER | 16.8 |
| YCC2-GVMGFO | 16.4 |
| YCC2-KGHRGF | 16.6 |
| Soluble GFOGER | 15.4 |
| Soluble GVMGFO | 13.3 |
| Soluble KGHRGF | 24.0 |
| CCC2-GPOGPR(short) | 14.0 |
| CCC2-GFOGER(short) | 15.7 |

TABLE 2-continued (The below described "Peptide names" references SEQ ID NOS 1-5, 7, 9, 8, 12-14, 19-21, 10-11, 15-18 and 23-25, respectively, in order of appearance)

| Peptide name | Retention time (min) |
|---|---|
| CCC2-GPOGPR | 14.4 |
| CCC2-GFOGER | 16.0 |
| CCC2-GVMGFO | 18.2 |
| CCC2-KGHRGF | 15.8 |
| CC2-GPOGPR (short) | 13.0 |
| C2-GPOGPR (short) | 12.0 |
| Soluble GPOGPR (short) | 10.6 |

Results of Mass Analysis of Peptide

Mass analysis of each of the abovementioned peptides synthesized and purified was performed by a MALDI-TOF MS. The calculated value and actual measured value of the mass of each of the peptides are shown in Table 3. CHCA was used as a matrix for preparing a measurement sample. From these results, it was confirmed that all the peptides were peptides intended.

TABLE 3

(The below described "Peptide names" references SEQ ID NOS 1-5, 7-9, 12-14, 19-21, 10-11, 15-18 and 22-25, respectively, in order of appearance)

| Peptide name | Calculated value | Actual measured value |
|---|---|---|
| YCC2 | 4004.7 [M] | 4005.3 [M + H]$^+$ |
| CC2 | 3678.6 [M] | 3679.7 [M + H]$^+$ |
| CC1 | 3472.5 [M] | 3473.0 [M + H]$^+$ |
| C2 | 3472.5 [M] | 3474.1 [M + H]$^+$ |
| CCC2 | 3884.6 [M] | 3885.5 [M + H]$^+$ |
| CCCC2 | 4090.6 [M] | 4091.6 [M + H]$^+$ |
| Y2 | 3592.6 [M] | 3593.3 [M + H]$^+$ |
| YCC2-Scr | 4004.7 [M] | 4005.5 [M + H]$^+$ |
| YCC2-GFOGER | 4086.7 [M] | 4087.9 [M + H]$^+$ |
| YCC2-GVMGFO | 4640.0 [M] | 4641.0 [M + H]$^+$ |
| YCC2-KGHRGF | 5435.4 [M] | 5435.9 [M + H]$^+$ |
| Soluble GFOGER | 3179.5 [M] | 3180.3 [M + H]$^+$ |
| Soluble GVMGFO | 3423.6 [M] | 3425.1 [M + H]$^+$ |
| Soluble KGHRGF | 4772.1 [M] (Average mass) | 4772.1 [M + H]$^+$ (Average mass) |
| CCC2-GPOGPR(short) | 3350.3 [M] | 3351.2 [M + H]$^+$ |
| CCC2-GFOGER(short) | 3432.3 [M] | 3434.0 [M + H]$^+$ |
| CCC2-GPOGPR | 4418.8 [M] | 4419.4 [M + H]$^+$ |
| CCC2-GFOGER | 4500.8 [M] | 4501.2 [M + H]$^+$ |
| CCC2-GVMGFO | 4519.8 [M] | 4520.0 [M + H]$^+$ |
| CCC2-KGHRGF | 4513.9 [M] | 4513.9 [M + H]$^+$ |
| RGD pep | 489.2 [M] | 490.2 [M + H]$^+$ |
| CC2-GPOGPR (short) | 3144.3 [M] | 3145.1 [M + H]+ |
| C2-GPOGPR (short) | 2938.3 [M] | 2939.8 [M + H]+ |
| Soluble GPOGPR (short) | 2803.3 [M] | 2804.4 [M + H]+ |

Example 2

<Evaluation of Triple Helix Structure in Collagen-Like Peptide>

Confirmation of triple-helical structure by observation of peptide conformation

The structure of the peptide was confirmed by CD spectrum (circular dichroism spectrometer J-820, JASCO Corporation). A peptide powder was dissolved in a degassed 0.05% TFA/$H_2O$ to prepare a solution of 1 mg/ml. After heating at 80° C. for 5 min, the solution was left to stand at 4° C. overnight to cause refolding as a measurement sample. CD spectrum was measured under the conditions of: temperature 4° C., 37° C., 80° C.; cell length 0.05 cm; sensitivity standard (100 mdeg); measurement wavelength 250 to 190 nm; data collection interval 0.2 nm; scanning speed 50 nm/min; response 0.5 sec; band width 1 nm; cumulated number 4. A signal obtained ($\theta_{obs}$) was expressed as a residue average molar ellipticity ($\theta_{mrw}$). $\theta_{mrw}$ was calculated by the following formula.

$$\theta_{mrw} = \frac{(\theta_{obs} \times \omega_{mrw})}{10 \times c \times l} \quad \text{[Formula 1]}$$

(In the above formula, mrw represents residue average molecular weight, c represents peptide concentration (mg/ml), and l represents cell length (cm).)

A thermal stability of the triple-helical structure was observed by monitoring $\theta_{mrw}$, 225 associated with a change in temperature. The measurement conditions were: 4 to 75° C. or 4 to 90° C.; cell length 0.05 cm; measurement wavelength 225 nm; data collection interval 0.5° C.; temperature gradient 18° C./h; sensitivity standard (100 mdeg); response 2 sec; band width 1 nm. It was determined that the triple-helical structure completely turned into a random coil structure in a region where the signal was linearly diminishing.

Results of CD Spectrum Measurement of Peptide

Figure 4A:
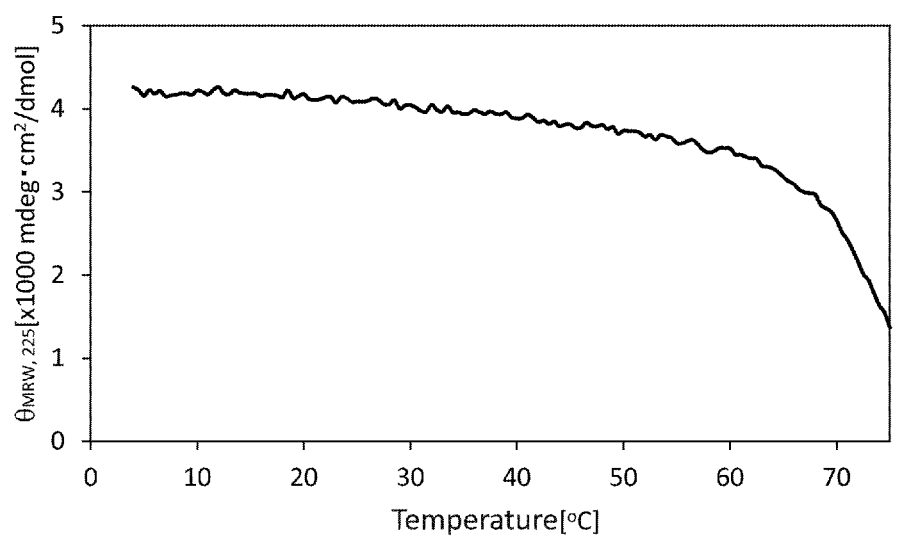
FIG. 4A shows 0225 of YCC2 (SEQ ID NO: 1) by changing the temperature.
Figure 4B:
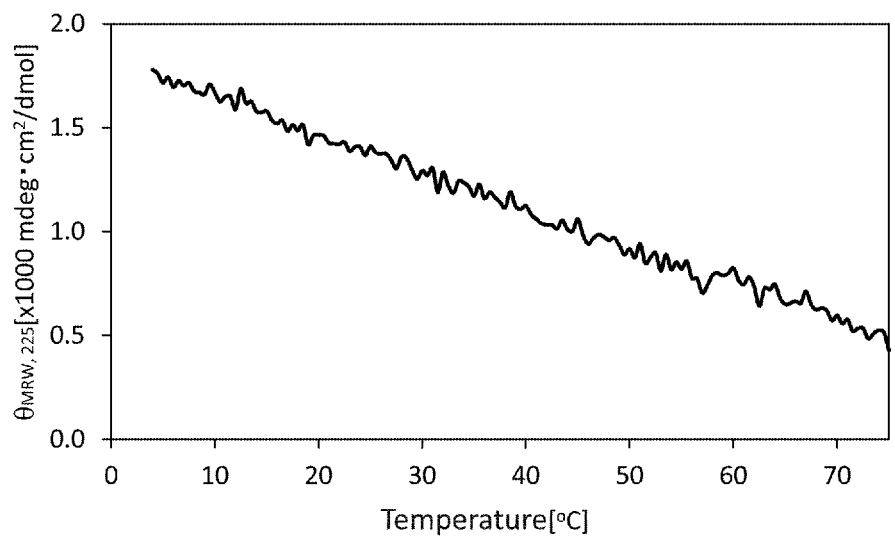
FIG. 4B shows 0225 of YCC2-Scr (SEQ ID NO: 9) by changing the temperature.

With regard to each peptide synthesized, the results obtained by measuring the CD spectra thereof at 4° C., 37° C. and 80° C. are shown in FIG. 3A to FIG. 3G. Further, with regard to YCC2 (SEQ ID NO: 1) and YCC2-Scr (SEQ ID NO: 9), FIG. 4A and FIG. 4B show results obtained by measuring CD spectrum intensities thereof at 225 nm (0225) as the temperature changes. From these measurement results, all the peptides other than YCC2-Scr (SEQ ID NO: 9) exhibited positive Cotton effects at about 225 nm only at 4° C. and 37° C. That is, it was observed that these peptides were each formed into the triple-helical structure at a temperature of 37° C. or lower, but were in denatured states at 80° C. Although CD spectrum was not measured on C2 (SEQ ID NO: 4), it was considered that C2 (SEQ ID NO: 4) was formed into the triple-helical structure as well due to the fact that all the peptides having the similar triple-helical skeletons were observed to have formed triple helixes. Meanwhile, with regard to YCC2-Scr (SEQ ID NO: 9), positive Cotton effects were observed at about 225 nm at all the temperatures measured. According to the results obtained by measuring the changes in 0225 at 225 nm as the temperature changed, while CC2 (SEQ ID NO: 2) was observed to have exhibited thermal denaturation at about 75° C., a linear functional decrease was observed with YCC2-Scr (SEQ ID NO: 9). From these findings, it was considered that collagen-like peptides other than YCC2-Scr (SEQ ID NO: 9) were each able to form a triple helix regardless of their terminus or internal sequences; and that although YCC2-Scr (SEQ ID NO: 9) did not form the triple-helical structure, it was formed into a polyproline II-type three-dimensional structure.

Example 3

<Gel Formation by Polymerization of Collagen-Like Peptide and Evaluation of Property Thereof>

By oxidatively cross-linking the abovementioned peptide having the triple-helical structure with DMSO as an oxidant, there was produced a gel containing a polymerized peptide prepared by polymerizing a collagen-like peptide. The progression of the polymerization reaction by oxidative cross-linking was observed by measuring the remaining thiol groups.

Measurements of Remaining Thiol Group in Oxidative Polymerization Reaction of Collagen-Like Peptide Degassed water was used to prepare a peptide solution having a concentration of 1.11% (w/v), and the solution was then put into a PCR tube. After heating this solution at 80° C. for 5 min, it was then left to sand still at 4° C. overnight. By adding DMSO to this solution, there was prepared a peptide solution having a final concentration of 10% DMSO, peptide 1% (w/v). The PCR tube was then filled with a mineral oil in a way such that the mineral oil covered the surface of the solution. In every measurement, the mineral oil was eliminated from the peptide solution to prepare a peptide solution for oxidation monitoring. Ellman's reagent was prepared in a way such that 9 mg/ml of DTNB was present in 50 mM of a phosphate buffer solution (pH 8.4). 33 mM phosphate buffer solution (pH 8.4) and Ellman's reagent 1.5 mg/ml were left to stand for 5 mM, then a light absorbance was then measured after a solution with a final concentration of peptide 0.167 mg/ml. Recorded were changes in absorbance with time, with a moment when DMSO was added being a starting point (0 hour). Since the Ellman's reagent generates 5-mercapto-2-nitrobenzoate ($\lambda$ max=412 nm, $\varepsilon$=1.55×10$^4$) depending on the amount of thiol groups (referred to as "SH groups" hereunder) in the peptide, measured was a absorbance at 412 nm. After the measurement, optical path length was compensated by measuring absorbance at 997 nm and 900 nm.

Figure 5:
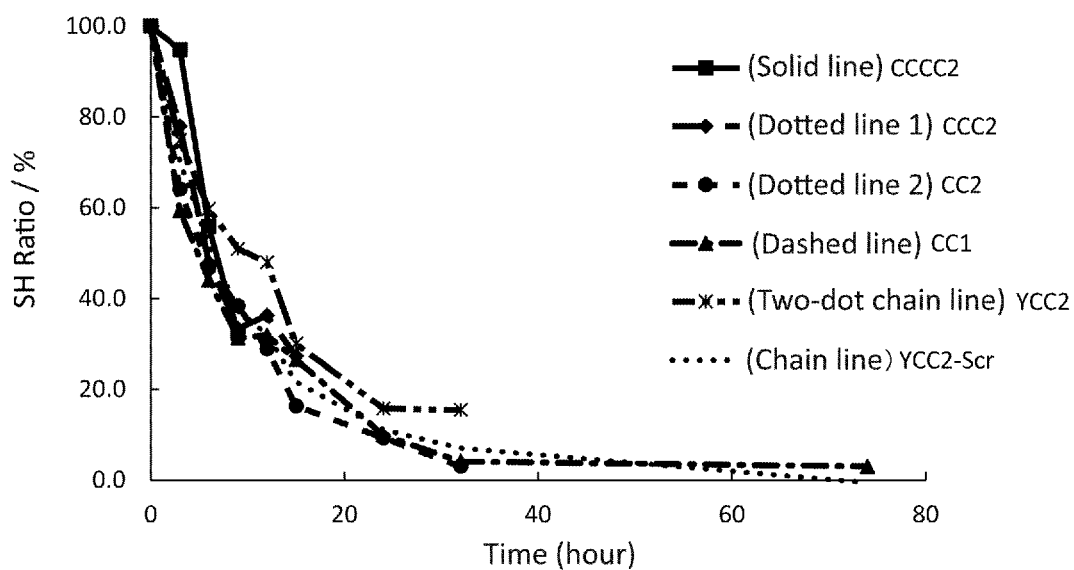
FIG. 5 shows time courses obtained by quantifying an SH amount in each peptide in polymerization reactions of CCCC2 (SEQ ID NO: 7), CCC2 (SEQ ID NO: 5), CC2 (SEQ ID NO: 2), CC1 (SEQ ID NO: 3), YCC2 (SEQ ID NO: 1) and YCC2-Scr (SEQ ID NO: 9).

Changes in ratio of SH amount with time are shown in FIG. 5, with the SH amount of each peptide at 0 hour being 100%. CCCC2 (SEQ ID NO: 7) turned into a gel in 12 hours, CCC2 (SEQ ID NO: 5) turned into a gel in 24 hours, CC2 (SEQ ID NO: 2) and YCC2 (SEQ ID NO: 1) turned into gels in 74 hours. Thus, quantitative data were not measured in the time period therebeyond. Each peptide had substantially exhibited a similar rate of reduction in the percentage of SH amount. Further, the ratio of SH amount in CC1 (SEQ ID NO: 3) and YCC2-Scr (SEQ ID NO: 9) which did not turn into a gel was approximately 0%. From the above results, it was indicated that the oxidation of most of the peptides had been completed by approximately 100% at the time when 74 hours had passed. Here, samples which did not turn into gels at the time when three days had passed were determined as peptides incapable of turning into gels.

Production of Polymerized Peptide Hydrogel of Collagen-Like Peptide and Evaluation of Stability Thereof Degassed water was used to prepare a peptide solution having a concentration of 1.11% (w/v) or 1.66% (w/v), and the solution was then put into a PCR tube. After heating this solution at 80° C. for 5 min using a polymerase chain reaction (PCR) machine (TaKaRa PCR Thermal Cycler, TAKARA BIO INC.), the solution was then left to stand at 4° C. overnight. By adding DMSO and water to this solution, there was prepared a peptide solution having a concentration of 10% DMSO, 0.1 to 1.5% (w/v). The PCR tube was then filled with a mineral oil in a way such that the mineral oil covered the liquid surface, followed by allowing the solution to stand at room temperature for a given period of time to achieve a gel. Then, gel formation was determined by looking at whether a stainless ball could be held by the gel.

Figure 6:
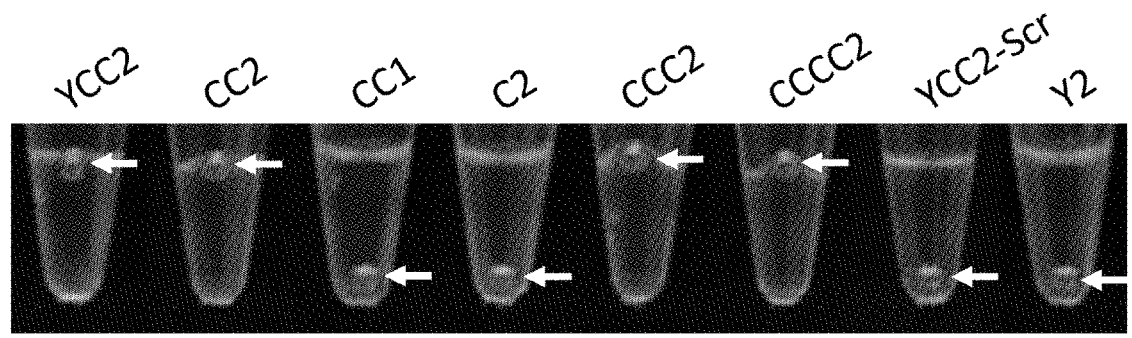
FIG. 6 shows a comparison result of a gel-forming capability of each peptide in hydrogels formed of YCC2 (SEQ ID NO: 1), CC2 (SEQ ID NO: 2), CC1 (SEQ ID NO: 3), C2 (SEQ ID NO: 4), CCC2 (SEQ ID NO: 5), CCCC2 (SEQ ID NO: 7), YCC2-Scr (SEQ ID NO: 9) and Y2 (SEQ ID NO: 8).

Evaluation Result of Gel-Forming Capability Depending on Change in Sequence of Peptide Chain The gel-forming capability of each peptide at a concentration of 1% (w/v) was evaluated, and the results thereof are shown in FIG. 6. A white arrow shows the position of a stainless ball. From these results, gel formation was observed with gels having not less than two Cys residues in the vicinities of both the amino terminus and carboxy terminus (see CC2 (SEQ ID NO: 2), CC1 (SEQ ID NO: 3) and C2 (SEQ ID NO: 4)). Further, gel was not formed with peptides having random coil structures (see YCC2 (SEQ ID NO: 1) and YCC2-Scr (SEQ ID NO: 9)). Therefore, it was indicated that the triple-helical structure was important for forming a gel. Further, the time spent in forming gel at 1% (w/v) is shown in Table 4.

TABLE 4

(The below described names reference SEQ ID NOS 7, 5, 2 and 1)

| Name | Time (hour) | | | | | |
|---|---|---|---|---|---|---|
|  | 9 | 12 | 15 | 24 | 32 | 74 |
| CCCC2 | X | ○ | ○ | ○ | ○ | ○ |
| CCC2 | X | X | X | ○ | ○ | ○ |
| CC2 | X | X | X | X | ○ | ○ |
| YCC2 | X | X | X | X | X | ○ |

○: Gelated
X: Failed to gelate

From the above results, it was indicated that the larger the amount of Cys residues contained in peptide, the shorter the gel formation time was. Further, it was indicated that peptides capable of turning into gels were CCCC2 (SEQ ID NO: 7), CCC2 (SEQ ID NO: 5), CC2 (SEQ ID NO: 2) and YCC2 (SEQ ID NO: 1).

Evaluation Results of Influence of Peptide Concentration on Gel Formation

The various concentrations to form gels containing the peptides (CCCC2 (SEQ ID NO: 7), CCC2 (SEQ ID NO: 5), CC2 (SEQ ID NO: 2) and YCC2 (SEQ ID NO: 1)) which formed gels at the concentration of 1% (w/v) were evaluated. Table 5 shows the evaluation results of their concentrations that are required for gel formation under oxidizing conditions: at room temperature; and for three days.

TABLE 5

(The below described names reference SEQ ID NOS 7, 5, 2 and 1)

| Name | Peptide concentration/% (w/v) | | | | | |
|---|---|---|---|---|---|---|
|  | 0.1 | 0.2 | 0.3 | 0.5 | 0.7 | 1.0 |
| CCCC2 | X | X | ○ | ○ | ○ | ○ |
| CCC2 | — | — | X | ○ | ○ | ○ |
| CC2 | — | — | X | X | X | ○ |
| YCC2 | — | — | X | X | X | ○ |

○: Gelated
X: Failed to gelate
—: Not tested

It was indicated that the peptides exhibited high gel forming capabilities in order of CCCC2 (SEQ ID NO: 7), CCC2 (SEQ ID NO: 5), CC2 (SEQ ID NO: 2) and YCC2 (SEQ ID NO: 1). Further, CCCC2 (SEQ ID NO: 7) turned into a gel even at a concentration of 0.3% (w/v).

Measurements of Hydrogel Stability

Measurements of Hydrogel Stability to Reduction Treatment

Figure 7:
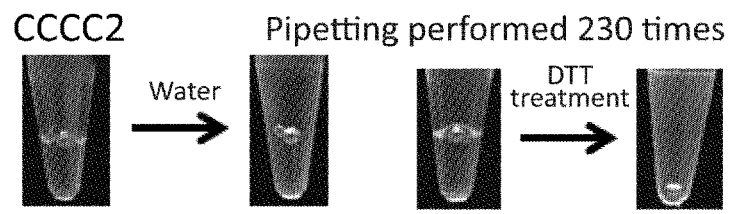
FIG. 7 shows a judgment result of a collapsibility of each of hydrogels formed of CCCC2 (SEQ ID NO: 7), CCC2 (SEQ ID NO: 5), CC2 (SEQ ID NO: 2), and YCC2 (SEQ ID NO: 1).
Figure 7:
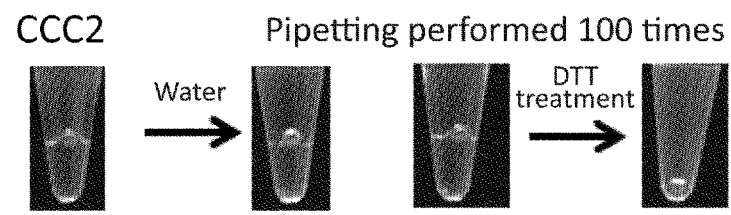
Figure 7:
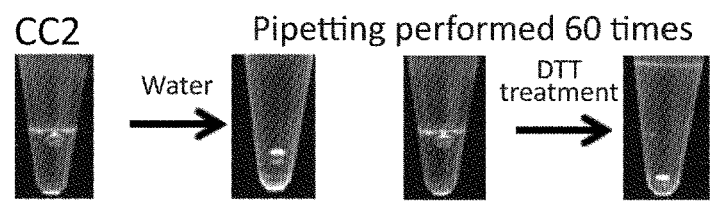
Figure 7:
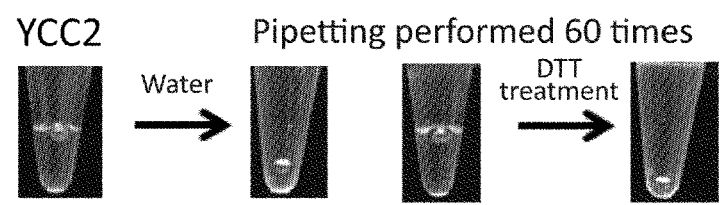

It was indicated that a hydrogel formed by using DMSO to oxidize a peptide having not less than two Cys residues in the vicinities of both the N- and C-terminals. There, verification was made on whether gel caused a collapse by breaking the disulfide cross-linking by a reduction treatment. A reducing solution of 100 μl (100 mM DTT, 50 mM phosphate buffer solution (pH 8.4)) or water was added to the hydrogel (30 μl) prepared. There was then exhibited a final concentration of peptide concentration 2.3 mg/ml, 2.3% DMSO 23 mM DTT, 12 mM phosphate buffer solution (pH 8.4) or 2.3 mg/ml, 2.3% DMSO. Then, pipetting procedure was respectively performed at a frequency of about 90 times/min and a volume of 100 μl/each time, using a yellow tip (up to 200 μl). The results thereof are shown in FIG. 7.

From these results, it was indicated that all the hydrogels as polymerized peptides completely caused collapse by the reduction treatment. Meanwhile, as a result of adding water, although gel collapse was not observed with CCCC2 (SEQ ID NO: 7) and CCC2 (SEQ ID NO: 5), gel collapse was observed with CC2 (SEQ ID NO: 2) and YCC2 (SEQ ID NO: 1).

Measurement of Thermal Stability of Hydrogel

After mounting the stainless ball on the hydrogel prepared, they were moved to a thermostatic device, and were left to stand for 10 min at various temperatures between 35° C. and 95° C. Whether gel collapse had occurred was determined by judging the sinking of the stainless ball.

Thermal Stability Measurement Results

Figure 8:
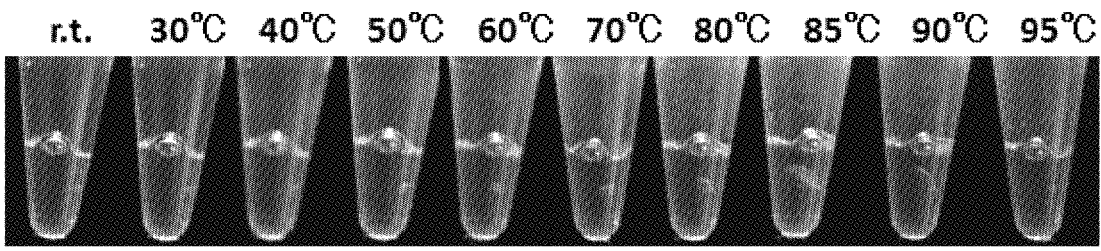
FIG. 8 shows thermal stability measurement results of the hydrogels formed of CCCC2 (SEQ ID NO: 7), CCC2 (SEQ ID NO: 5), CC2 (SEQ ID NO: 2), and YCC2 (SEQ ID NO: 1).
Figure 8:
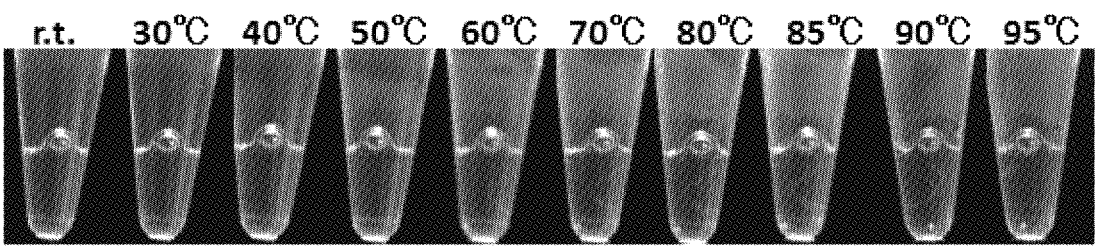
Figure 8:
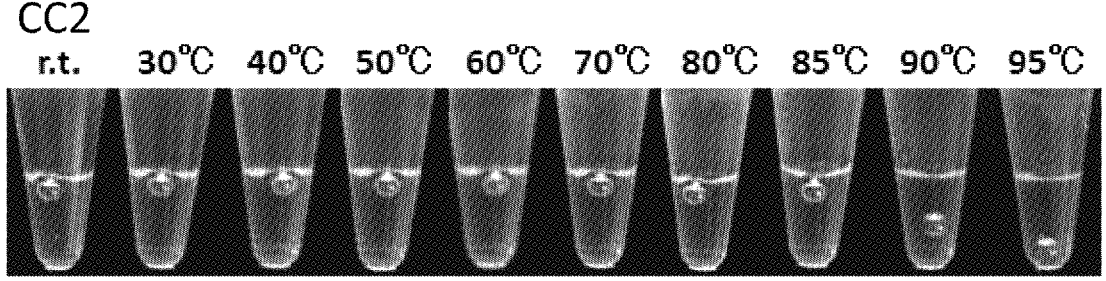
Figure 8:
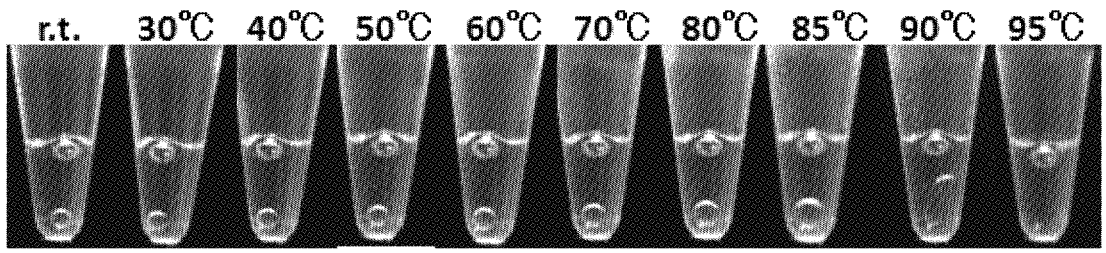

FIG. 8 shows the results obtained by measuring the thermal stability of a hydrogel produced using the 1% (w/v) peptide. From these results, as for hydrogels formed of CCCC2 (SEQ ID NO: 7), CCC2 (SEQ ID NO: 5) or YCC2 (SEQ ID NO: 1), the sinking of the stainless ball was not observed at temperatures not higher than 95° C. With regard to a hydrogel formed of CC2 (SEQ ID NO: 2), the stainless ball started to sink in a range of 85° C. to 90° C., and then completely sank at 95° C. Thus, it is considered that the triple-helical structure had stabilized in proportion to the number of disulfide bonds, which then led to higher denaturation temperatures of the peptides.

Example 4

<Production of Polymerized Peptide Thin Membrane and Evaluation of Strength Thereof>

YCC2 (SEQ ID NO: 1) was used to produce a polymerized peptide thin membrane. Degassed water was used to prepare a peptide solution having a concentration of 1.11% (w/v), and the solution was then put into a PCR tube. After heating this solution at 80° C. for 5 min, it was then left to stand at 4° C. overnight. By adding DMSO to this solution, there was prepared a peptide solution at a final concentration of 10% DMSO, 1.0% (w/v). This peptide solution was then put on a non-water absorbing substrate (paramembrane, silicon-processed hole glass, Teflon (registered trademark) plate). At that time, a PVDF membrane or a nylon mesh as a supporting material was disposed on the non-water absorbing substrate. The solution then turned into a gel after being left to stand for three days under room temperature and a wet condition (10% DMSO). Then, the condition was switched to a dry condition, and drying was performed at room temperature for three days. The most excellent combination of a non-water absorbing substrate and a supporting material was a combination of a Teflon (registered trademark) plate and a nylon mesh.

Production Results of Polymerized Peptide Thin Membrane

Figure 9:
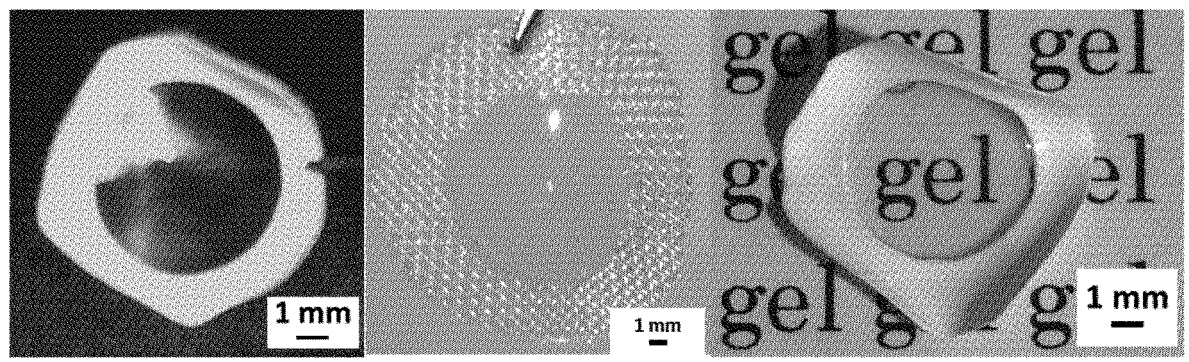
FIG. 9 shows a polymerized peptide thin membrane produced. Left: inner diameter 6 mm, peptide amount 1 mg; support PVDF membrane-, Center: inner diameter 10 mm, peptide amount 3 mg; support nylon mesh-, Right: inner diameter 6 mm, peptide amount 1 mg, support PVDF membrane.

A collagen-like polymerized peptide thin membrane made of the one formed of the YCC2 peptide (SEQ ID NO: 1), exhibited a significantly high transparency (FIG. 9).

Rehydration of Polymerized Peptide Thin Membrane

Water was added to the polymerized peptide thin membrane produced by the above method on a non-water absorbing membrane. After hydration for several minutes, water that had failed to be absorbed by the polymerized peptide thin membrane was collected and eliminated. In this way, there was prepared a rehydrated polymerized peptide hydrogel.

Rehydration result of polymerized peptide thin membrane

Figure 10:
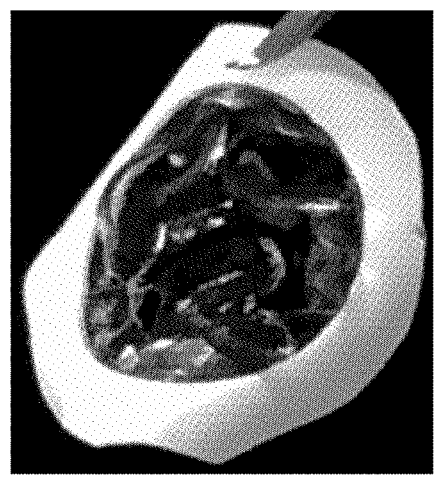
FIG. 10 is an appearance diagram showing a rehydrated polymerized peptide thin membrane.
Figure 11A:
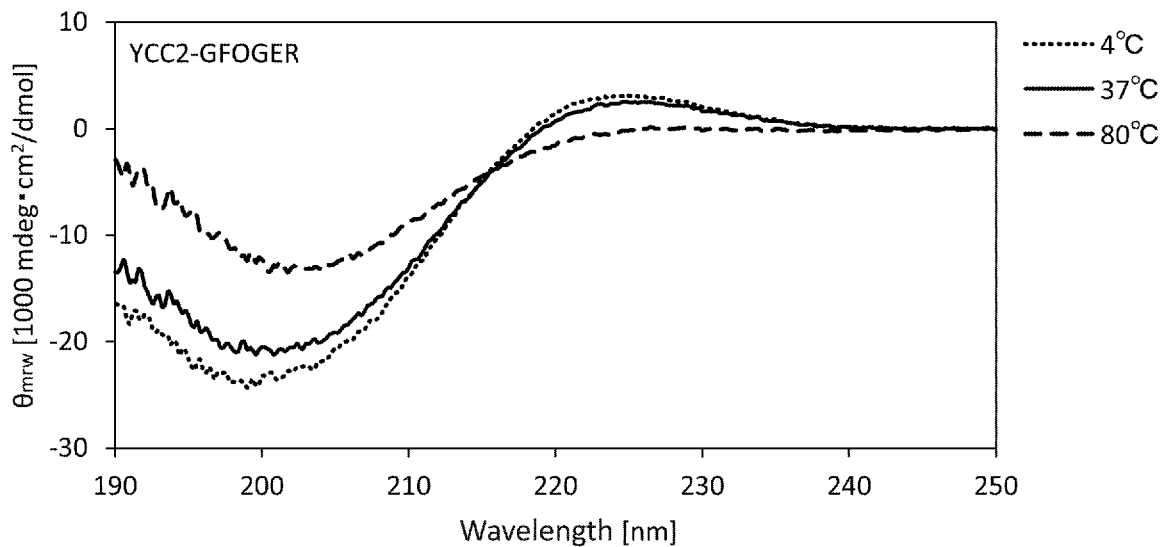
FIG. 11A shows CD spectra of a synthesized peptide incorporating a biologically active motif, at 4° C., 37° C. and 80° C.: CD spectrum of YCC2-GFOGER (SEQ ID NO: 12).
Figure 11B:
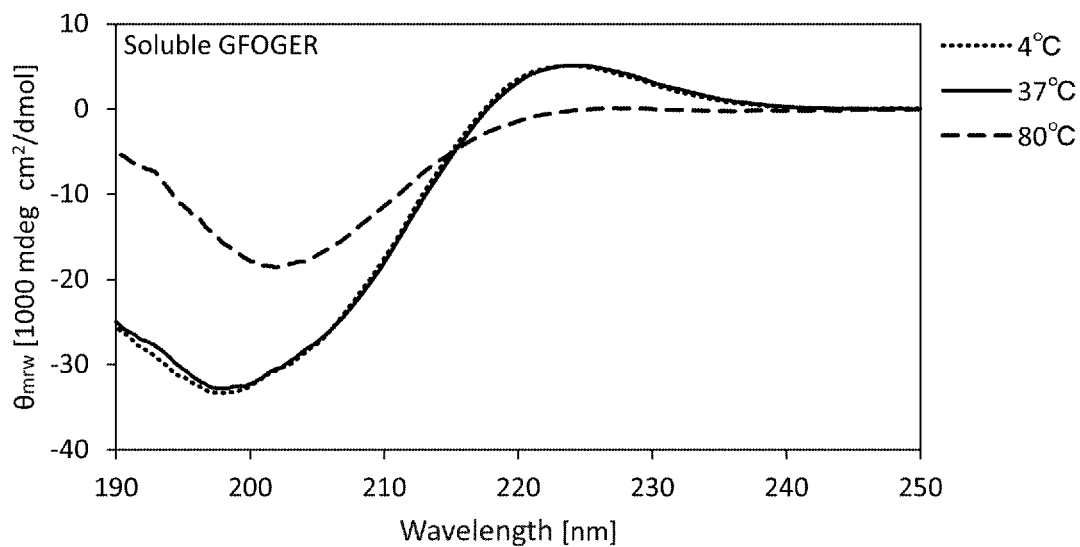
FIG. 11B shows CD spectra of a synthesized peptide incorporating a biologically active motif, at 4° C., 37° C. and 80° C.: CD spectrum of Soluble-GFOGER (SEQ ID NO: 19).
Figure 11C:
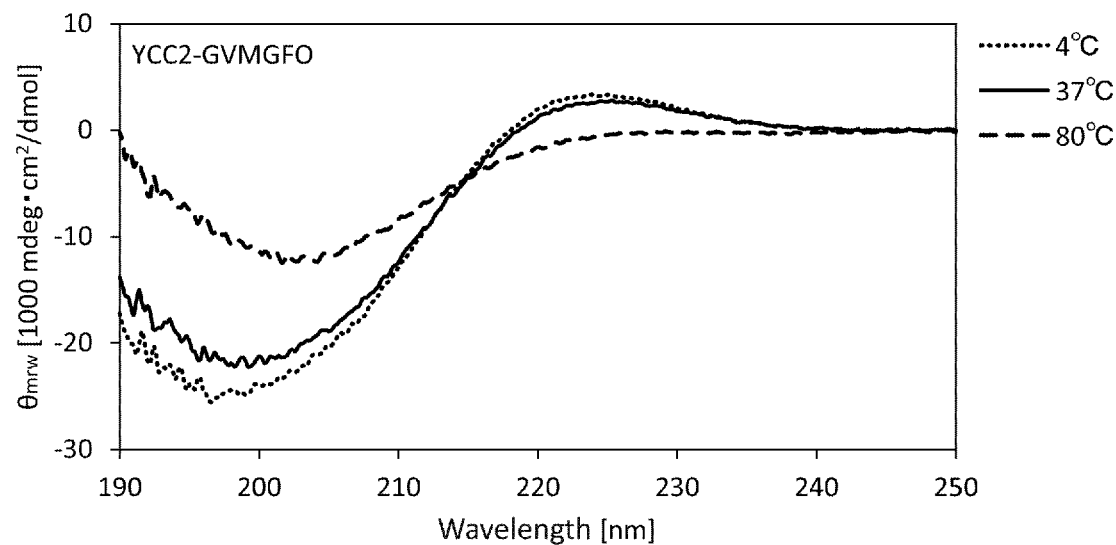
FIG. 11C shows CD spectra of a synthesized peptide incorporating a biologically active motif, at 4° C., 37° C. and 80° C.: CD spectrum of YCC2-GVMGFO (SEQ ID NO: 13) at 4° C., 37° C. and 80° C.
Figure 11D:
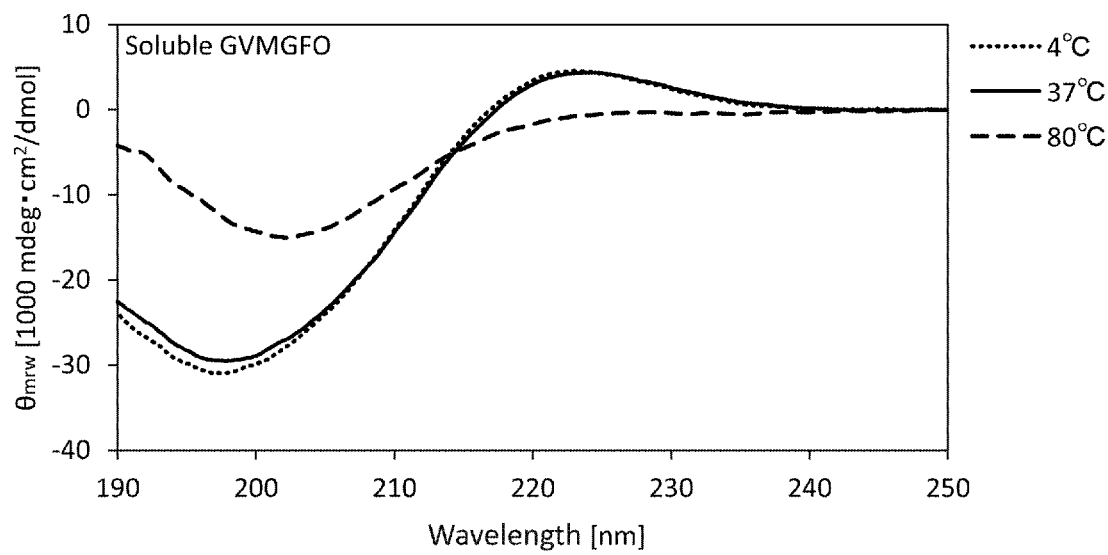
FIG. 11D shows CD spectra of a synthesized peptide incorporating a biologically active motif, at 4° C., 37° C. and 80° C.: CD spectrum of Soluble -GVMGFO (SEQ ID NO: 20).
Figure 11E:
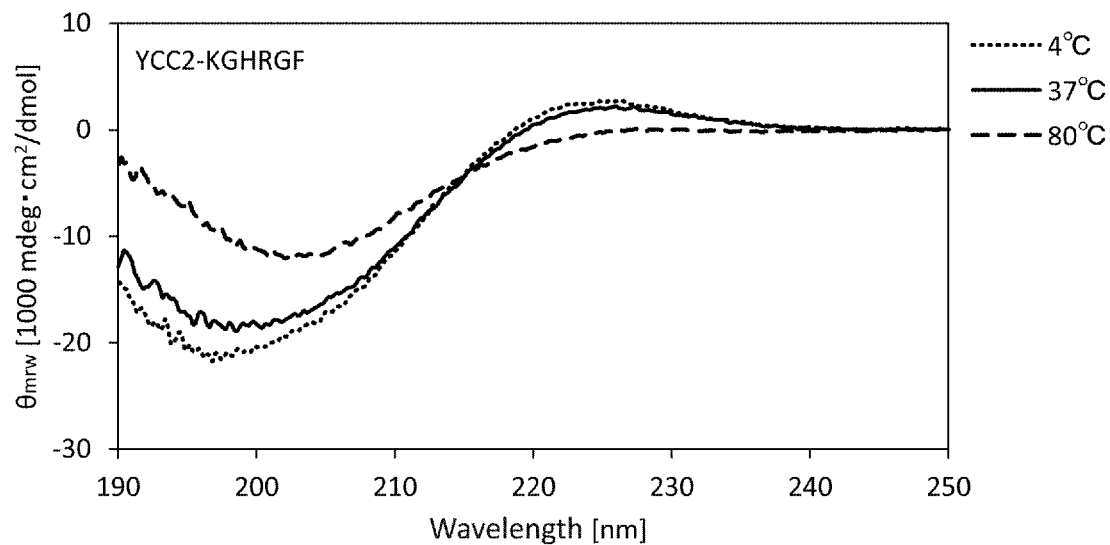
FIG. 11E shows CD spectra of a synthesized peptide incorporating a biologically active motif, at 4° C., 37° C. and 80° C.: CD spectrum of YCC2-KGHRGF (SEQ ID NO: 14).
Figure 11F:
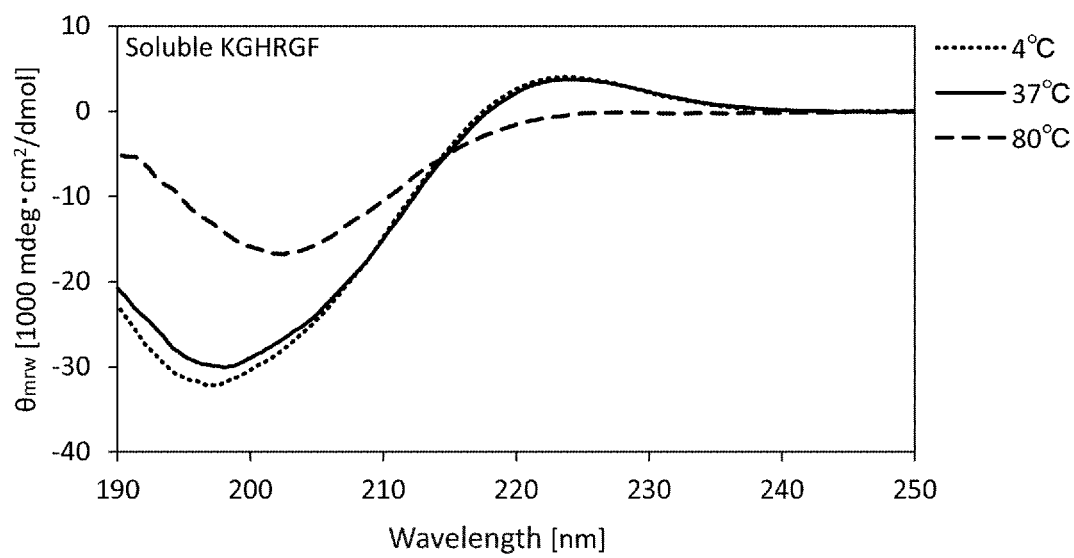
FIG. 11F shows CD spectra of a synthesized peptide incorporating a biologically active motif, at 4° C., 37° C. and 80° C.: CD spectrum of Soluble-KGHRGF (SEQ ID NO: 21).

FIG. 10 shows a result after obtaining the hydrogel of the rehydrated polymerized peptide. The hydrogel prepared by rehydration had a water-retaining amount smaller than that of hydrogel obtained without a procedure to dry, which caused peptide density to increase and thus made it possible to produce a hydrogel with a high strength.

Example 5

<Production of Laminated Polymerized Peptide Thin Membrane>

A laminated polymerized peptide thin membrane was produced by the following method, using a polymerized peptide produced by employing CCC2-GFOGER (short) (SEQ ID NO. 11).

(1) As is the case with example 4, the collagen-like peptide was dissolved in a degassed $H_2O$ (22.2 mg/ml), followed by heating and then gradually cooling it to form a triple helix.

(2) DMSO was added (10% DMSO, 20 mg/ml peptide), and oxidation occurs as a result of being left to stand, on a supporting material (diameter 1 cm circle), for about four days in a sealed container filled with 10% DMSO, thus forming a hydrogel.

(3) Drying as well as dehydration was performed in the atmosphere.

(4) A 10% DMSO, 20 mg/ml peptide solution prepared in the similar manner as (2) was laminated thereon, followed by performing oxidation for about four days in a sealed container filled with 10% DMSO.

(5) Drying as well as dehydration was performed in the atmosphere.

By rehydrating the polymerized peptide laminated thin membrane thus dried and then separating it from the supporting material, or by separating the polymerized peptide laminated thin membrane thus dried from the supporting material and then rehydrating it, there was prepared a polymerized peptide thin membrane with an improved strength.

Example 6

<Production and Evaluation of Polymerized Peptide Endowed with Bioactivity>

Production of polymerized peptide of collagen-like peptide having peptide chain incorporating biologically active motif YCC2-GFOGER (SEQ ID NO. 12), YCC2-GVMGFO (SEQ ID NO. 13) and YCC2-KGHRGF (SEQ ID NO. 14); and, as controls to these peptides, Soluble GFOGER (SEQ ID NO. 19), Soluble GVMGFO (SEQ ID NO. 20) and Soluble KGHRGF (SEQ ID NO. 21) which are peptides having no Cys residue in the vicinities of both the amino-terminus and carboxy-terminus, were synthesized by a method similar to that of example 2. And, as a result of measuring the CD spectrum of each peptide solution, the formation of the triple-helical structure was observed.

The measurement results of the CD spectra are shown in FIG. 11A to FIG. 11F. All the peptides exhibited positive Cotton effects at about 225 nm only at 4° C. and 27° C. That is, it was observed that these peptides were each formed into the triple-helical structure at a temperature of 37° C. or lower, but they could be denatured at 80° C. Further, these results indicate that the formation of the triple-helical structure at the temperature of 37° C. or lower is not associated with the existence or non-existence of the Cys residue in the primary structures of the peptide chains.

Next, a method similar to that of example 3 was employed to produce a gel containing a polymerized peptide of peptide chains incorporating these biologically active motifs. And, the gel was used in an evaluation of selective cell-binding activity that employs a cultured cell(s) described below.

Materials and Methods

Cell Culture

D-MEM High Glucose, D-MEM Low Glucose and 0.5% trypsin/EDTA were purchased from Wako Pure Chemical Industries, Ltd. (Osaka); FBS, penicillin. streptomycin (100×) were purchased from Invitrogen (Thermo Fisher Scientific corporation). Human mammary gland cancer (MDA-MB-231) was purchased from ATCC; Human skin fibroblasts (HDF) were purchased from Cell Applications. MDA-MB-231 was cultured using DMEM High Glucose (10% FBS, 100 Units/ml penicillin, 100 μg/ml streptomycin), and then maintained; and HDF was cultured using DMEM Low Glucose (10% FBS, 100 Units/ml penicillin, 100 μg/ml streptomycin), and then maintained. When used in cell adhesion assay and Western blotting, the cells were treated with 0.05% trypsin/EDTA, and then collected in a 15 ml tube to be subjected to centrifugal treatment at 1,200 rpm for four minutes. After the removal of the supernatant, the cells were suspended with an incubation medium by which the cells were incubated at 37° C. for 20 to 30 min and then recovered. Such cell suspension was used for cell adhesion assay and Western blotting.

Coating Cell Culture Dish with Peptide and Protein

Type I collagen (KOKEN CO., LTD, Tokyo) and BSA (Jackson Immuno Research Laboratories Inc., USA), in an aqueous solution as 30 μg/ml, were added to a 96-well plate (Nunc MicroWell 96-Well Microplates) by an amount of 50 μl/well, followed by drying the sample for two nights. Collagen-like peptides having no Cys residue were prepared as aqueous solutions of 1 to 3 mg/ml, and then heated at 95° C. for 5 min, followed by storing them at 4° C. overnight to form the triple-helical structure. Then, they were diluted to 30 μg/ml, and then added to a 96-well plate in an amount of 50 μl/well followed by drying them for two nights. Collagen-like peptides having Cys residues were dissolved in a degassed 0.05% (v/v) TFA aqueous solution, followed by preparing to a concentration of 300 μg/ml, and then heating the sample at 80° C. for 5 min. The samples were cooled in a gradual manner at a rate of 1° C./min until the temperature had reached 4° C., followed by storing the sample at 4° C. overnight to form the triple-helical structure. Then, they were diluted to 30 μg/ml in 30 mM MOPS buffer solution (pH 7.8) (Sigma-Aldrich: Sigma-Aldrich Japan, Tokyo), with 15% methanol, and then added to a 96-well plate by an amount of 50 μl/well to dry the sample for two nights. In the coating procedures using polymerized peptides incorporated various ligands, each peptide was dissolved in a degassed 0.05% (v/v) TFA aqueous solution (1 mg/ml), followed by heating it at 80° C. for 5 min, and then gradually cooling it at a rate of 1° C./min until 4° C. There, by storing the sample at 4° C. overnight, the triple-helical structure was formed. These peptides were mixed at various ratios, and diluted to a concentration of 20% (v/v) DMSO, total peptide concentration 0.3 mg/ml. Further, a mineral oil was layered on the peptide solution, and such peptide solution was then oxidized at room temperature until thiol could no longer be detected by Ellman's test. Then, this peptide solution was later diluted to 30 µg/ml with Milli Q water, and then added to a 96-well plate by an amount of 50 µl/well, then dried under air for two nights.

Cell Adhesion Assay

A 96-well plate coated with peptide or protein was blocked with 5 mg/ml of BSA thermally denatured at 60 to 70° C., then incubated at 37° C. for 1 to 2 hours. Washing was then carried out after removing the BSA solution, using PBS (10 mM phosphate buffer solution (pH 7.4), 137 mM NaCl, 2.7 mM KCl (Sigma Aldrich)). An MDA-MB-231 cell suspension (40-60×$10^3$ cells/well) or an HDF cell suspension (4-10×$10^3$ cells/well) was then added and incubated at 37° C. for 30 to 180 min. Then, after removing floating cells along with the medium, the samples were washed with PBS, and 4% (v/v) p-formaldehyde/phosphate buffer (pH 7.4) (Wako Pure Chemical Industries, Ltd.) was then employed to fix adherent cells, followed by stained with 2% crystal violet/MeOH (Wako Pure Chemical Industries, Ltd.). The stained cells were then observed using the laser scanning confocal microscope FV1000 (Olympus Corporation).

Western Blotting

A 6-well plate coated with peptide or protein was blocked with BSA (5 mg/ml) thermally denatured at 60 to 70° C., and incubated at 37° C. for 1 to 2 hours. The BSA solution was removed and washed the samples by PBS. An MDA-MB-231 cell suspension (50×$10^3$ cells/well) was then added and incubated at 37° C. for 90 min. The medium was removed, then cells were lysed by adding SDS sample buffer (50 mM Tris-HCl (pH 6.7), 2% SDS, 10% glycerol, 1 µg/ml pepstatin A, 1 µg/ml leupeptin, 1 mM PMSF, 2 mM NEM, 1 mM $Na_3VO_4$, 10 mM NaF) to the cells. They were then collected in a 1.5 ml tube, heated at 95° C. for 5 min and provided as an SDS-PAGE sample. The quantity of proteins in the SDS-PAGE sample prepared was determined by BCA method. Each sample was added to 10% (w/v) acrylamide gel in an amount of 30 µg/well, and separated by SDS-PAGE. The proteins prepared by separation were transcribed to a nitrocellulose membrane (GE Healthcare). Then, they were blocked overnight by immersion in a 5% (w/v) blocking solution prepared using a skim milk (Wako Pure Chemical Industries, Ltd.) and TBS (50 mM Tris-HCl (pH 7.4), 150 mM NaCl). A primary antibody diluted solution (1:1, 000) (anti-FAK mouse antibody (Merck Millipore Corporation, USA), anti-pFAK (pTyr397) rabbit antibody (Invitrogen) or anti-β-actin mouse antibody (Sigma Aldrich)) was added and left to stand for two to three hours. After removing the primary antibody, the nitrocellulose membrane immersed in TBS-T (0.1% Tween-20) was shaken for 10 to 20 min After repeating this three times, a secondary antibody diluted solution (1:1,000) (antimouse antibody goat antibody-HRP conjugate (Promega KK, Tokyo), antirabbit antibody goat antibody-HRP conjugate (Santa Cruz Biotechnologies Inc., USA) was added thereto, followed by leaving it to stand for 30 min After removing the secondary antibody, the nitrocellulose membrane immersed in TBS-T was shaken for 10 to 20 min After repeating this three times, chemical luminescence was caused by using Western blotting kitPlus (Pierce; Thermo Fisher Scientific Inc.), and visualized and quantified by LAS-3000 (FUJIMEMBRANE Corporation).

Observation Result of Cell Adhesion to Integrin Binding Sequence

Figure 12A:
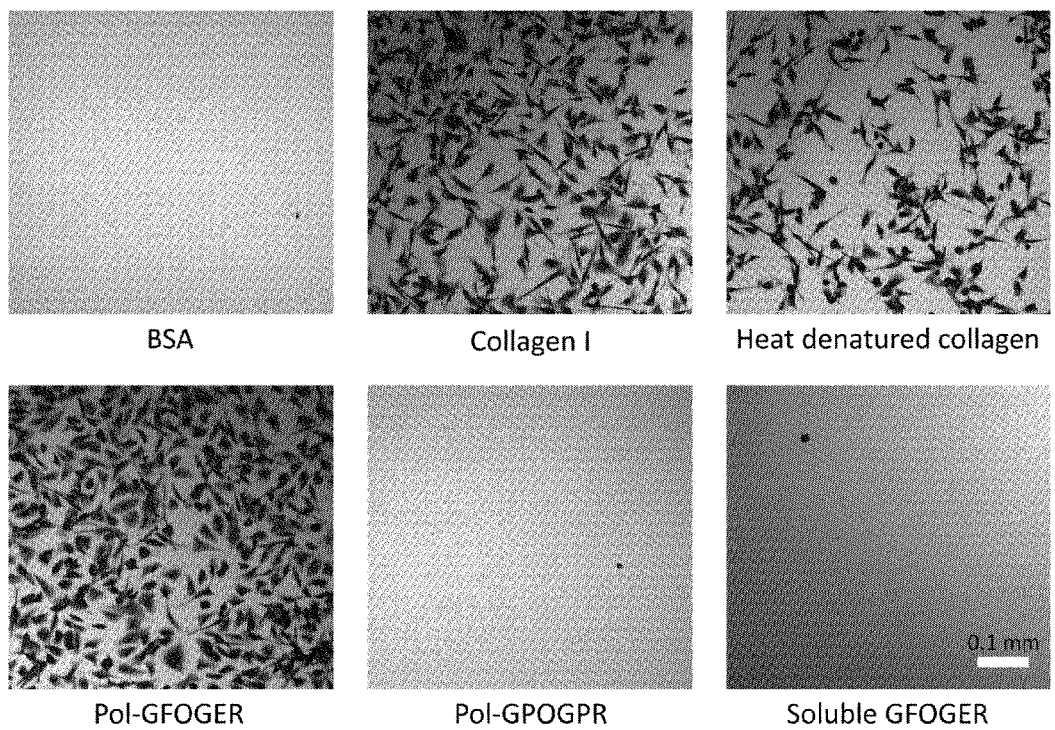
FIG. 12A is a series of microscope observation images for evaluating the adhesion capability of human fibroblasts to a gel containing a polymerized peptide of a collagen-like peptide having a GFOGER sequence motif (SEQ ID NO: 26), the images being presented as comparison results on: collagen I (Collagen I), denatured collagen (Heat denatured collagen), polymerized peptide incorporating GFOGER (SEQ ID NO: 26) (Pol-GFOGER ("GFOGER" disclosed as SEQ ID NO: 26)), polymerized peptide incorporating GPOGPR (SEQ ID NO: 40) (Pol-GPOGPR ("GPOGPR" disclosed as SEQ ID NO: 40)) and soluble GFOGER (SEQ ID NO: 26) (Soluble GFOGER (SEQ ID NO: 19)).
Figure 12B:
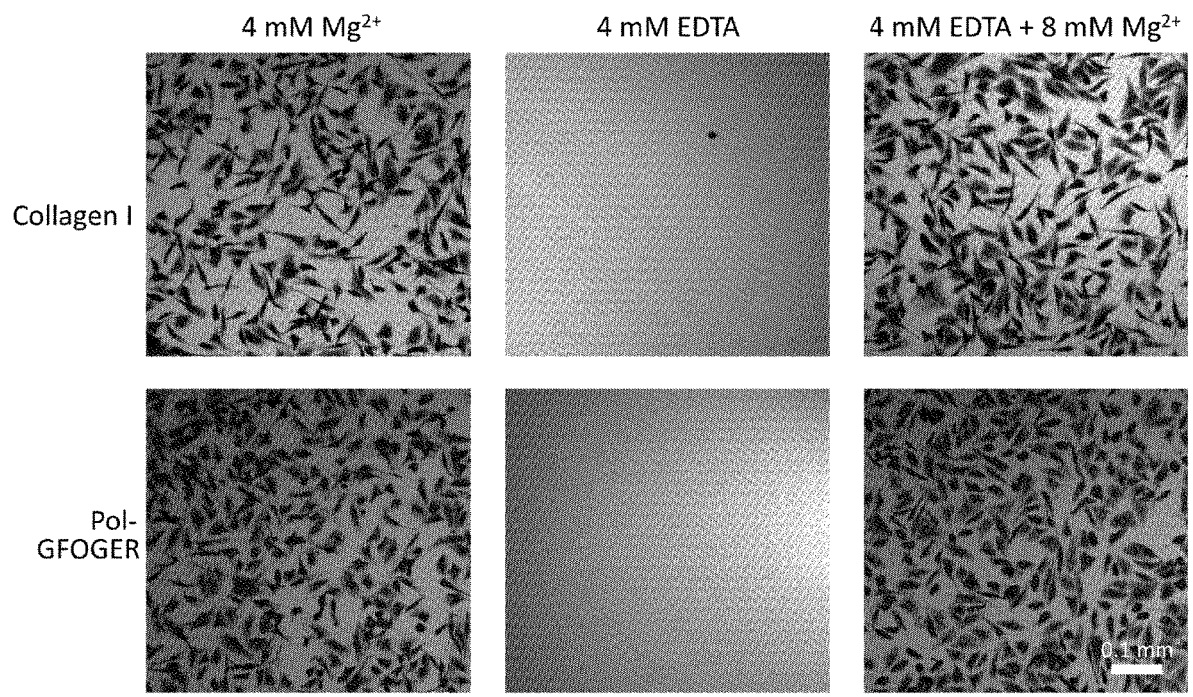
FIG. 12B shows a result obtained by comparing the adhesion capability of human fibroblasts to a gel formed of a polymerized peptide (Pol-GFOGER ("GFOGER" disclosed as SEQ ID NO: 26)) of a collagen-like peptide having a GFOGER sequence motif (SEQ ID NO: 26) with an adhesion capability in the case of type I collagen (Collagen I; positive control). Presented are microscope observation images as study results of Mg ion requirement and inhibitory activity by EDTA addition.

A 96-well plate was coated with each of BSA; type I collagen; YCC2 polymerized peptide (SEQ ID NO: 1) (Pol-GPOGPR ("GPOGPR" disclosed as SEQ ID NO: 40)); YCC2-GFOGER (SEQ ID NO: 12) polymerized peptide (Pol-GFOGER ("GFOGER" disclosed as SEQ ID NO: 26)); and a peptide (Soluble GFOGER (SEQ ID NO: 19)) that contains ligands, and does not form a polymerized peptide, followed by observing and comparing cell adhesion after culturing MDA-MB-231 (FIG. 12A and FIG. 12B). With regard to YCC2 (SEQ ID NO: 1) and YCC2-GFOGER (SEQ ID NO: 12), triple helices were formed under a reducing condition, then diluted with a basic buffer which constituted an oxidation condition. In this way, the peptides were oxidized on the 96-well plate such that disulfide cross-linking was accomplished.

Significant cell adhesion was observed with the type I collagen, gelatin and Pol-GFOGER ("GFOGER" disclosed as SEQ ID NO: 26). In contrast, cell adhesion was not observed with BSA, Pol-GPOGPR ("GPOGPR" disclosed as SEQ ID NO: 40) and soluble GFOGER (SEQ ID NO: 26) (FIG. 12A).

Further, inhibition of cell adhesion caused by integrin was observed with the type I collagen and Pol-GFOGER ("GFOGER" disclosed as SEQ ID NO: 26) due to EDTA. As a result of adding 4 mM EDTA to each of the type I collagen and Pol-GFOGER ("GFOGER" disclosed as SEQ ID NO: 26), cell adhesion was inhibited. Meanwhile, in an experimental group where 4 mM EDTA and 8 mM $Mg^{2+}$ were added, the inhibitory effect by EDTA disappeared, and significant cell adhesion was exhibited (FIG. 12B).

From this result, MDA-MB-231 caused cell adhesion dependent on the internal sequence of Pol-GFOGER ("GFOGER" disclosed as SEQ ID NO: 26). Moreover, such cell adhesion was inhibited by EDTA, and then restored by $Mg^{2+}$, which indicated that this cell adhesion was a type of cell adhesion dependent on integrin. From these findings, it was indicated that YCC2 (SEQ ID NO: 1) could be utilized as a scaffold base material for cell culturing, and that by incorporating into the internal sequence of YCC2 (SEQ ID NO: 1) various receptor binding motifs that are contained in natural collagens, it became possible to induce cell adhesion specific to a target receptor.

Results of Signal Input Via Integrin

Figure 13A:
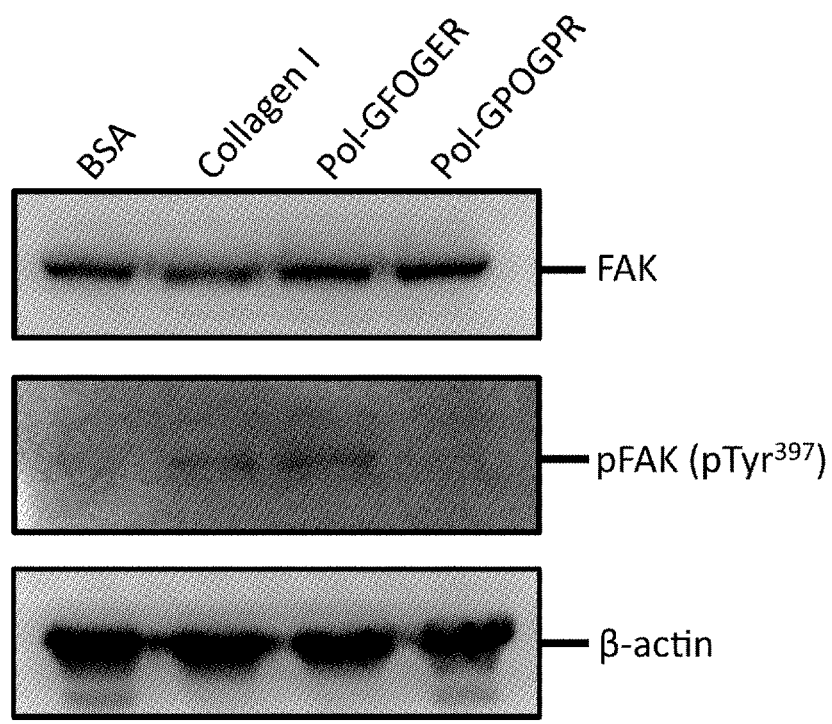
FIG. 13A shows results of Western blotting, the results being presented as comparison results comparing the gel (Pol-GFOGER ("GFOGER" disclosed as SEQ ID NO: 26)) formed of the polymerized peptide of the collagen-like peptide having the GFOGER sequence motif (SEQ ID NO: 26) with collagen I (Collagen I; positive control) and GPOGPR motif (SEQ ID NO: 40) (Pol-GPOGPR ("GPOGPR" disclosed as SEQ ID NO: 40)) in terms of signal of FAK phosphorylation by integrin.
Figure 13B:
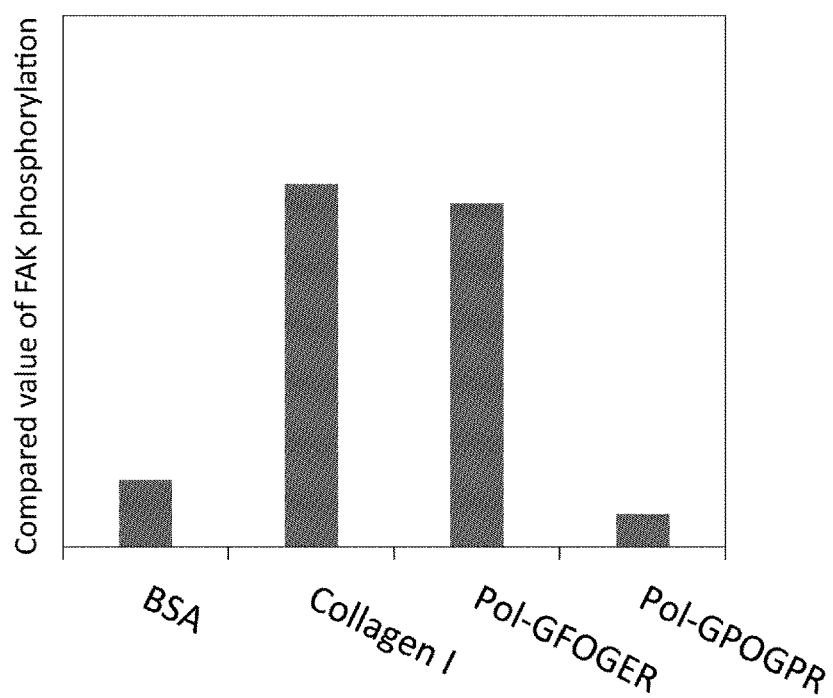
FIG. 13B shows comparison results comparing the gel (Pol-GFOGER ("GFOGER" disclosed as SEQ ID NO: 26)) formed of the polymerized peptide of the collagen-like peptide having the GFOGER sequence motif (SEQ ID NO: 26) with collagen I (Collagen I; positive control) and GPOGPR motif (SEQ ID NO: 40) (Pol-GPOGPR ("GPOGPR" disclosed as SEQ ID NO: 40)) in terms of signaling of FAK phosphorylation by integrin: results comparing impacts on FAK phosphorylation.

A 96-well plate was coated with BSA, type I collagen, YCC2-GFOGER (SEQ ID NO: 12) polymerized peptide (Pol-GFOGER ("GFOGER" disclosed as SEQ ID NO: 26)) and YCC2 polymerized peptide (SEQ ID NO: 1) (Pol-GPOGPR ("GPOGPR" disclosed as SEQ ID NO: 40)), then MDA-MB-231 was cultured for 90 min. At that time, with regard to YCC2 (SEQ ID NO: 1) and YCC2-GFOGER (SEQ ID NO: 12), triple helices were formed under a reducing condition, and then diluted by using a basic buffer which constituted an oxidation condition. In this way, the peptides were oxidized on the 96-well plate such that disulfide cross-linking was allowed to accomplish, and that coating could thus be carried out. FIG. 13A shows results of Western blotting of the cultured cells, using FAK and pFAK (pTyr397). Further, the band strength of pFAK (pTyr397) to that of FAK was analyzed with an image analysis software Image J, and the numerical results thereof are shown in FIG. 13B. While phosphorylation of FAK was not observed with the cells cultured on Pol-GPOGPR ("GPOGPR" disclosed as SEQ ID NO: 40), a same degree of phosphorylation was observed between the cells cultured on Pol-GFOGER ("GFOGER" disclosed as SEQ ID NO: 26) and the ones cultured on the type I collagen. From this result, it was indicated that by incorporating the ligand of integrin into the peptide sequence, not only cell adhesion by integrin was able to be induced, but the inputs of intracellular signals were made possible as well. Here, other than integrin, it was considered that inputs of signals specific to receptors were possible even when incorporating motifs of ligands of DDR and HSPG.

Figure 14A:
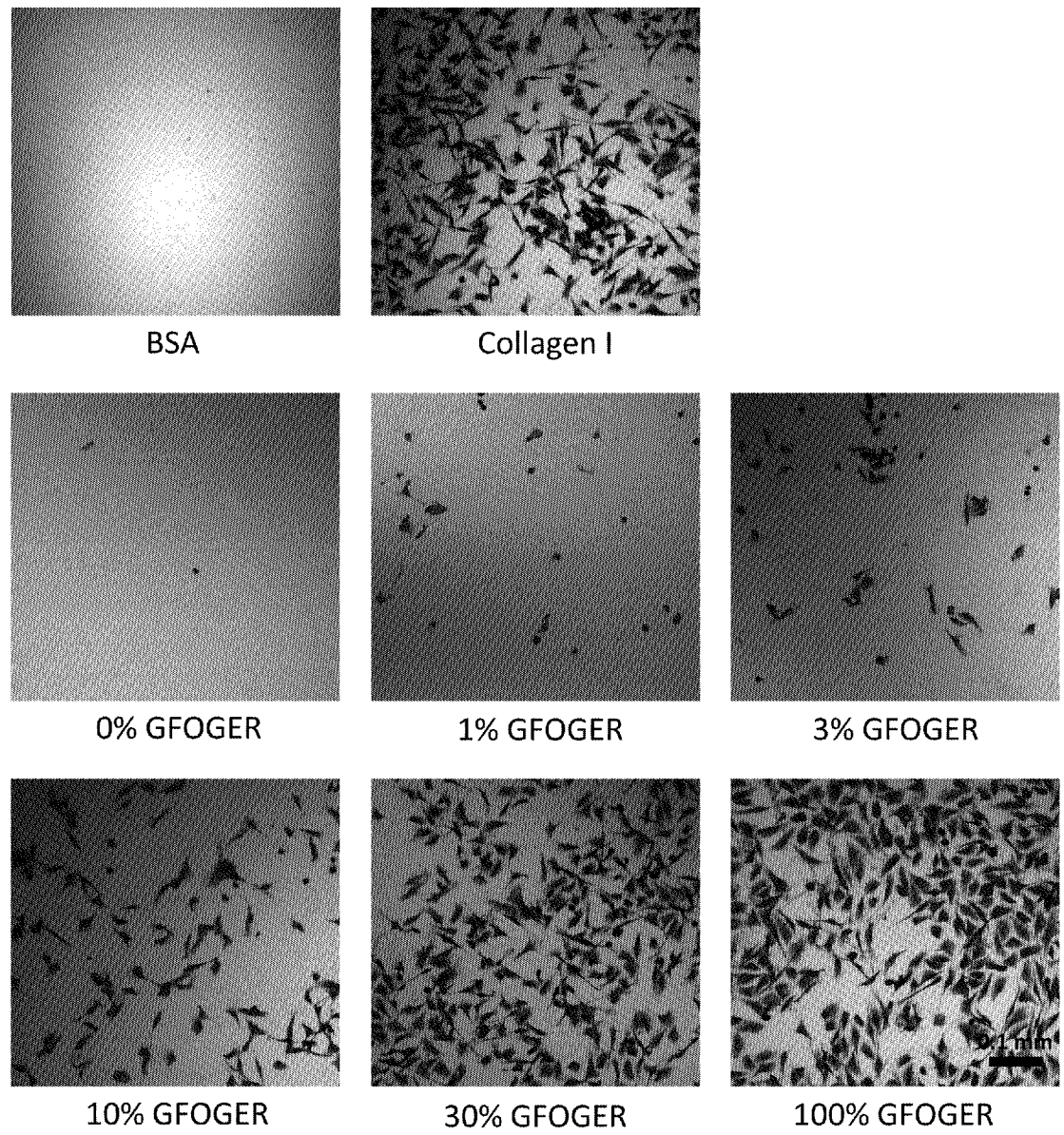
FIG. 14A is a series of microscope observation images comparing the polymerized peptide (Pol-GFOGER ("GFOGER" disclosed as SEQ ID NO: 26)) of the collagen-like peptide having the GFOGER sequence motif (SEQ ID NO: 26) with collagen I (Collagen I) and GPOGPR motif (SEQ ID NO: 40) (Pol-GPOGPR ("GPOGPR" disclosed as SEQ ID NO: 40)) in terms of change in the number of adherent cells due to a change in presence ratio of a binding motif amount therein.
Figure 14B:
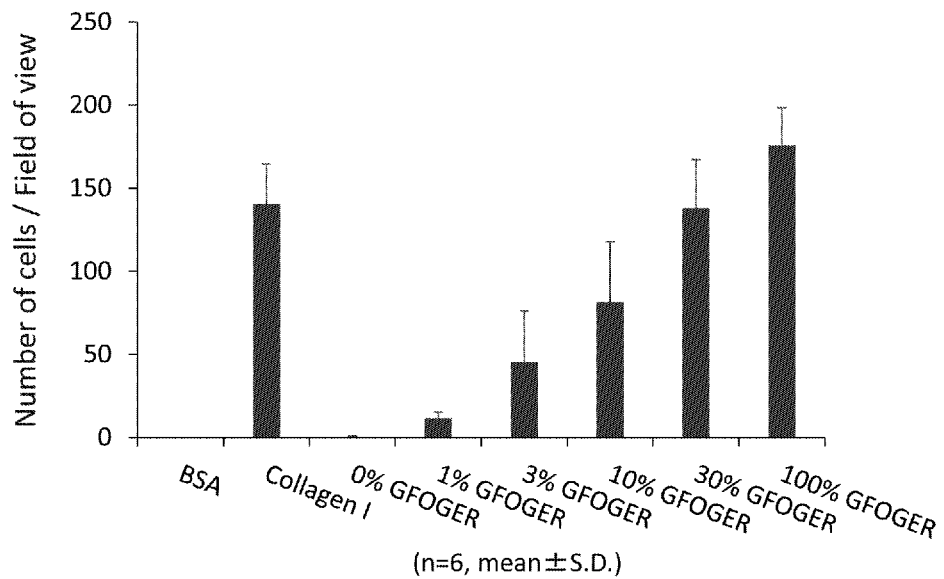
FIG. 14B shows measurement results of the numbers of adherent cells, the results comparing the polymerized peptide (Pol-GFOGER ("GFOGER" disclosed as SEQ ID NO: 26)) of the collagen-like peptide having the GFOGER sequence motif (SEQ ID NO: 26) with collagen I (Collagen I) and GPOGPR motif (SEQ ID NO: 40) (Pol-GPOGPR ("GPOGPR" disclosed as SEQ ID NO: 40)) in terms of change in the number of adherent cells according to a change in the presence ratio of binding motif amount therein.
Figure 14C:
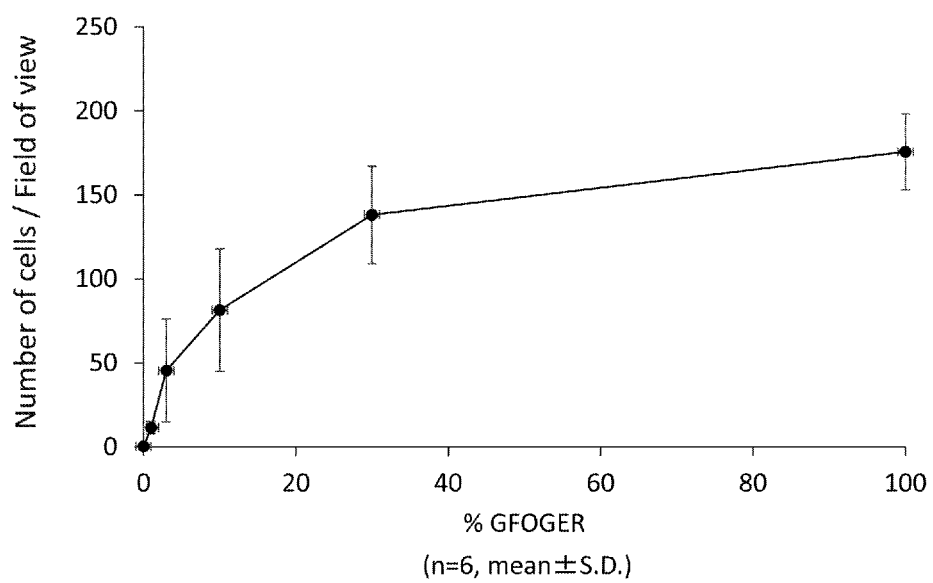
FIG. 14C shows a result obtained by evaluating the change in the number of adherent cells according to the change in the presence ratio of binding motif amount in the polymerized peptide (Pol-GFOGER ("GFOGER" disclosed as SEQ ID NO: 26)) of the collagen-like peptide having the GFOGER sequence motif (SEQ ID NO: 26). There is shown a dose-response curve of GFOGER sequence motif (SEQ ID NO: 26) presence ratio with respect to the number of adherent cells.

Observation Result of Change in Cell Adhesion Capability Dependent on Ligand Content A 96-well plate was coated with BSA, type I collagen, a thermally denatured type I collagen (gelatin) and a polymerized peptide of YCC2 (SEQ ID NO: 1) and YCC2-GFOGER (SEQ ID NO: 12) prepared by mixing at various ratios by weight, followed by culturing MDA-MB-231 on this plate at 37° C. under a condition of 5% $CO_2$ for 180 min With regard to YCC2 (SEQ ID NO: 1) and YCC2-GFOGER (SEQ ID NO: 12), triple helices were formed under a reducing condition, followed by mixing them at various ratios by weight, and then diluting them with a basic buffer to oxidize and copolymerize them, coating thus coated on the 96-well plate. After culturing the cells, adherent cells were fixed and stained, and the observation results thereof are shown in FIG. 14A. Further, the number of the adherent cells was calculated, and the comparison results thereof are shown in FIG. 14B and FIG. 14C.

The number of the adherent cells increased depending on the ratio of the GFOGER motif (SEQ ID NO: 26) present. A 100% GFOGER (SEQ ID NO: 26) group exhibited a higher number of the adherent cells than that of the type I collagen (FIG. 14B).

From these results, there was a tendency that MDA-MB-231 was able to sensitively detect the ligand of integrin, and that the number of adherent cells had logarithmically increased with respect to the contained amount of the ligand of integrin.

Therefore, it is considered that by adjusting the amount of the ligand contained in the polymerized peptide, the number of the adherent cells can be controlled, and various environments for cell culturing can be reproduced. Further, while a collagen having a molecular weight of about 300 kDa has one integrin-binding site, a triple-helical peptide of about 12 kDa, in the case of YCC2-GFOGER (SEQ ID NO: 12), contains one integrin-binding site. Thus, it is considered that when identical masses of a collagen and a mixed polymerized peptide of YCC2 (SEQ ID NO: 1) and YCC2-GFOGER (SEQ ID NO: 12) are coated, the same degree of integrin-binding sites as that of the collagen may be contained when the content of YCC2-GFOGER (SEQ ID NO: 12) is about 4%. However, as a result of comparing the collagen and the polymerized peptide of the collagen-like peptide in view of the number of the adherent cells, there was exhibited the same level of cell adhesion capability as that of the collagen when the content of YCC2-GFOGER (SEQ ID NO: 12) was 30%. It is considered that such difference is either a difference in coating efficiency between coating using the collagen and coating using the subject peptide, or attributed to the fact that the collagen has not only integrin, but multiple binding motifs to receptors. By employing the polymerized peptide of the subject invention, it is possible to obtain the number of ligands per unit area that is necessary or sufficient for triggering a cell's activities such as proliferation and differentiation.

Cell Adhesion with Respect to Ligand Sequences of Different Receptors

Figure 15A:
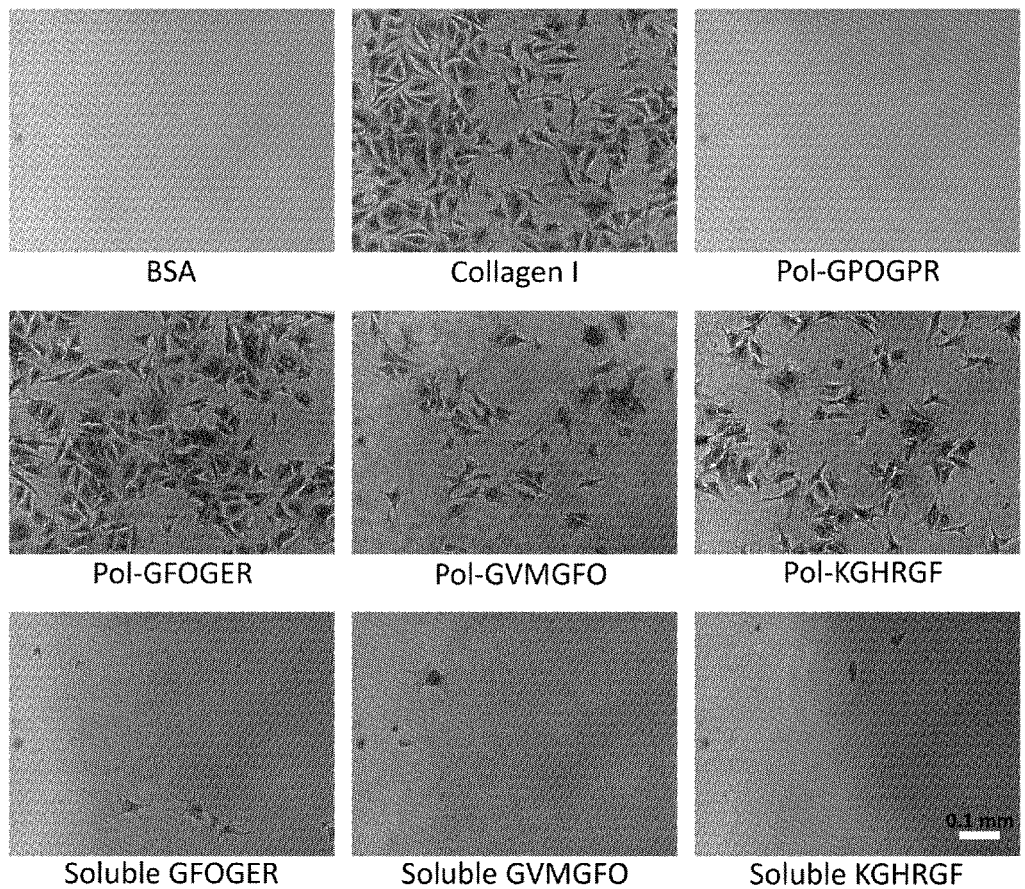
FIG. 15A is a series of microscope observation images for comparing gels of polymerized peptides having GFOGER sequence motif (SEQ ID NO: 26), GVMGFO sequence motif (SEQ ID NO: 27) or KGHRGF sequence motif (SEQ ID NO: 28) (which are respectively referred to as Pol-GFOGER ("GFOGER" disclosed as SEQ ID NO: 26), Pol-GVMGFO ("GVMGFO" disclosed as SEQ ID NO: 27) and Pol-KGHRGF ("KGHRGF" disclosed as SEQ ID NO: 28)) with a polymerized peptide (Pol-GPOGPR ("GPOGPR" disclosed as SEQ ID NO: 40)) containing no binding motif, type I collagen (Collagen I), soluble GFOGER (SEQ ID NO: 26) (Soluble GFOGER (SEQ ID NO: 19)), soluble GVMGFO (SEQ ID NO: 27) (Soluble GVMGFO (SEQ ID NO: 20)) and soluble KGHRGF (SEQ ID NO: 28) (Soluble KGHRGF (SEQ ID NO: 21)) in terms of adhesion of human fibroblasts.
Figure 15B:
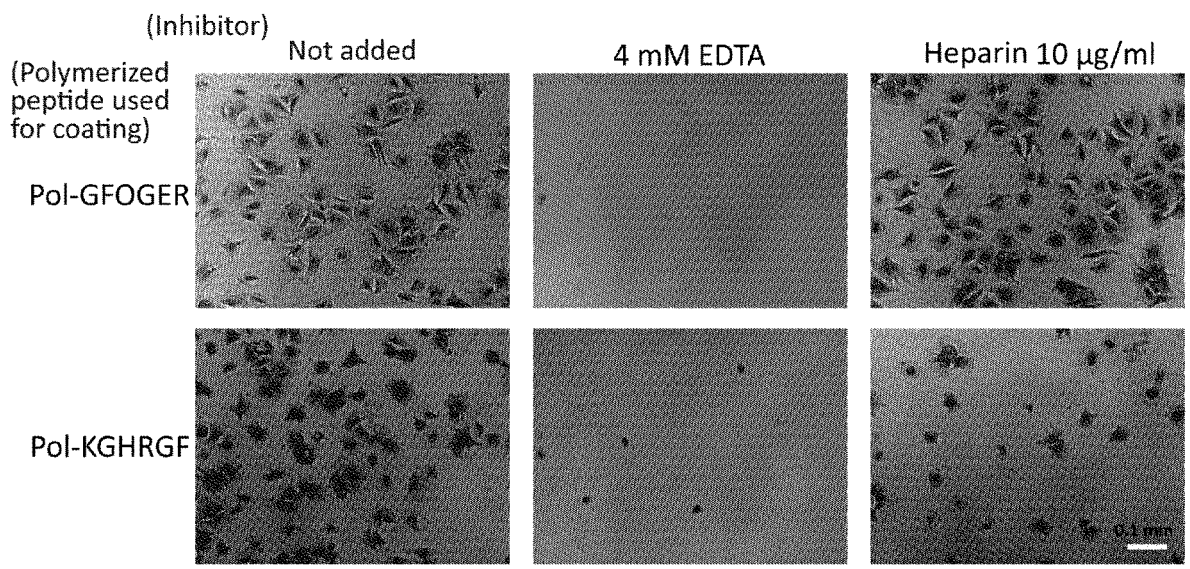
FIG. 15B is a series of microscope observation images that are presented as evaluation results of inhibitory effects of EDTA and heparin on human fibroblasts adhesion in the cases of polymerized peptides incorporating GFOGER (SEQ ID NO: 26) and KGHRGF (SEQ ID NO: 28) (which are respectively referred to as Pol-GFOGER ("GFOGER" disclosed as SEQ ID NO: 26) and Pol-KGHRGF ("KGHRGF" disclosed as SEQ ID NO: 28)).
Figure 15C:
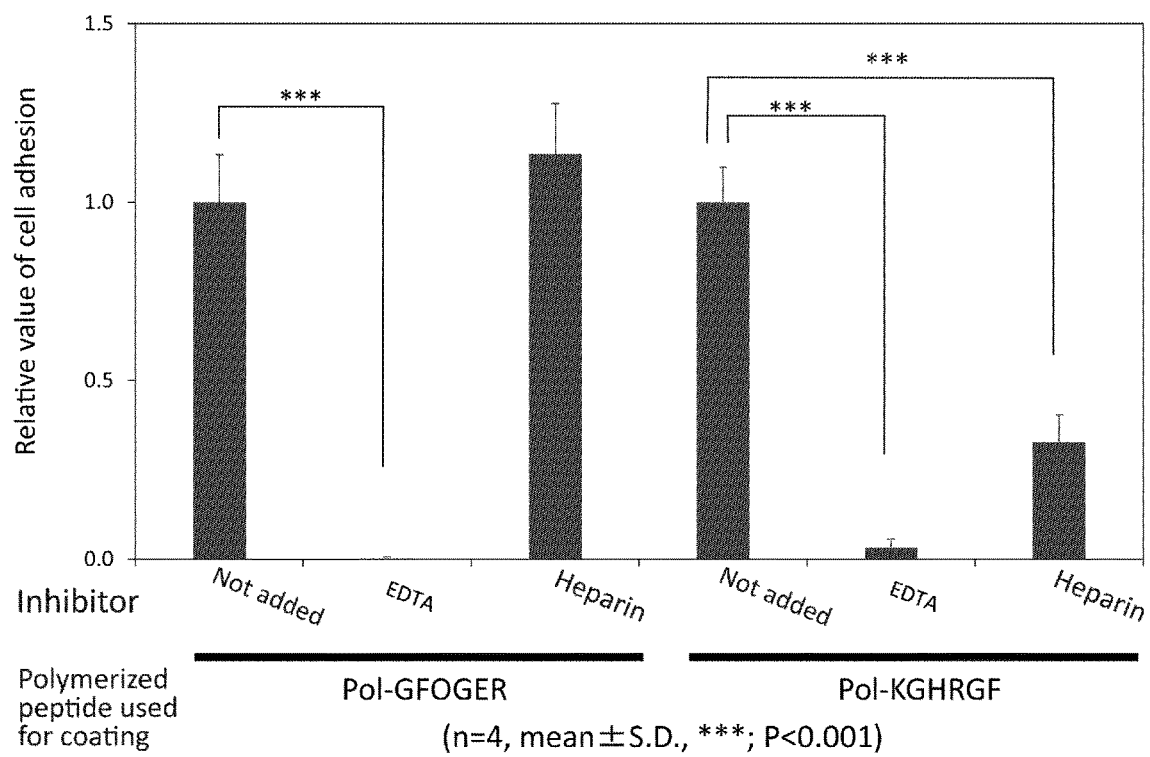
FIG. 15C shows a result obtained by measuring the number of cells with regard to the inhibitory effects of EDTA and heparin that are shown in FIG. 15B.

A 96-well plate was coated with BSA, type I collagen, YCC2 polymerized peptide (SEQ ID NO: 1) (Pol-GPOGPR ("GPOGPR" disclosed as SEQ ID NO: 40)), YCC2-GFOGER (SEQ ID NO: 12) polymerized peptide (Pol-GFOGER ("GFOGER" disclosed as SEQ ID NO: 26)), YCC2-GVMGFO (SEQ ID NO: 13) polymerized peptide (Pol-GVMGFO ("GVMGFO" disclosed as SEQ ID NO: 27)), YCC2-KGHRGF (SEQ ID NO: 14) polymerized peptide (Pol-KGHRGF ("KGHRGF" disclosed as SEQ ID NO: 28)), Soluble GFOGER (SEQ ID NO: 19), Soluble GVMGFO (SEQ ID NO: 20) and Soluble KGHRGF (SEQ ID NO: 21), followed by culturing HDF on this plate at 37° C. under a condition of 5% $CO_2$ for 60 min. At that time, with regard to YCC2-GFOGER (SEQ ID NO: 12), YCC2-GVMGFO (SEQ ID NO: 13) and YCC2-KGHRGF (SEQ ID NO: 14), triple helixes were formed under a reducing condition. Then, a basic buffer was used to dilute them to cause oxidation on the 96-well plate under an oxidation condition and polymerization to take place as well, thereby completing coating. After culturing the cells, the cells were fixed and stained, and the observation results thereof are shown in FIG. 15A. Further, studies were made on whether cell adhesion to Pol-GFOGER ("GFOGER" disclosed as SEQ ID NO: 26) and Pol-KGHRGF ("KGHRGF" disclosed as SEQ ID NO: 28) might be inhibited by EDTA or heparin which is known to specifically bind to KGHRGF (SEQ ID NO: 28) in the triple-helical sequence. These results are shown in FIG. 15B and FIG. 15C.

Cellular adhesion was observed with the type I collagen, Pol-GFOGER ("GFOGER" disclosed as SEQ ID NO: 26), Pol-GVMGFO ("GVMGFO" disclosed as SEQ ID NO: 27) and Pol-KGHRGF ("KGHRGF" disclosed as SEQ ID NO: 28). Particularly, a significant adhesion was observed with the type I collagen group and Pol-GFOGER ("GFOGER" disclosed as SEQ ID NO: 26). In contrast, cellular adhesion was not observed with Soluble GFOGER (SEQ ID NO: 19), Soluble GVMGFO (SEQ ID NO: 20) and Soluble KGHRGF (SEQ ID NO: 21) (FIG. 15A). Further, with respect to cell adhesion in the case of Pol-GFOGER ("GFOGER" disclosed as SEQ ID NO: 26), while EDTA exhibited an inhibitory effect, heparin did not exhibit an inhibitory effect. Meanwhile, with respect to cell adhesion in the case of Pol-KGHRGF ("KGHRGF" disclosed as SEQ ID NO: 28), both EDTA and heparin exhibited an inhibitory effect on cell adhesion (FIG. 15B).

In the above results, while cell adhesion was not observed with Pol-GPOGPR ("GPOGPR" disclosed as SEQ ID NO: 40), it was observed with Pol-GFOGER ("GFOGER" disclosed as SEQ ID NO: 26), Pol-GVMGFO ("GVMGFO" disclosed as SEQ ID NO: 27) and Pol-KGHRGF ("KGHRGF" disclosed as SEQ ID NO: 28). Further, while cell adhesion to Pol-GFOGER ("GFOGER" disclosed as SEQ ID NO: 26) was inhibited only by EDTA, cell adhesion to Pol-KGHRGF ("KGHRGF" disclosed as SEQ ID NO: 28) was significantly inhibited by both EDTA and heparin (two-sided test of Student's t-test). That is, it was indicated that by incorporating a ligand sequence capable of binding to a receptor into the sequence of YCC2 (SEQ ID NO: 1) that forms the triple helix, it became possible to induce cell adhesion by a particular receptor, thereby allowing the subject invention to be utilized for collagen-binding receptors in a versatile manner.

Figure 16A:
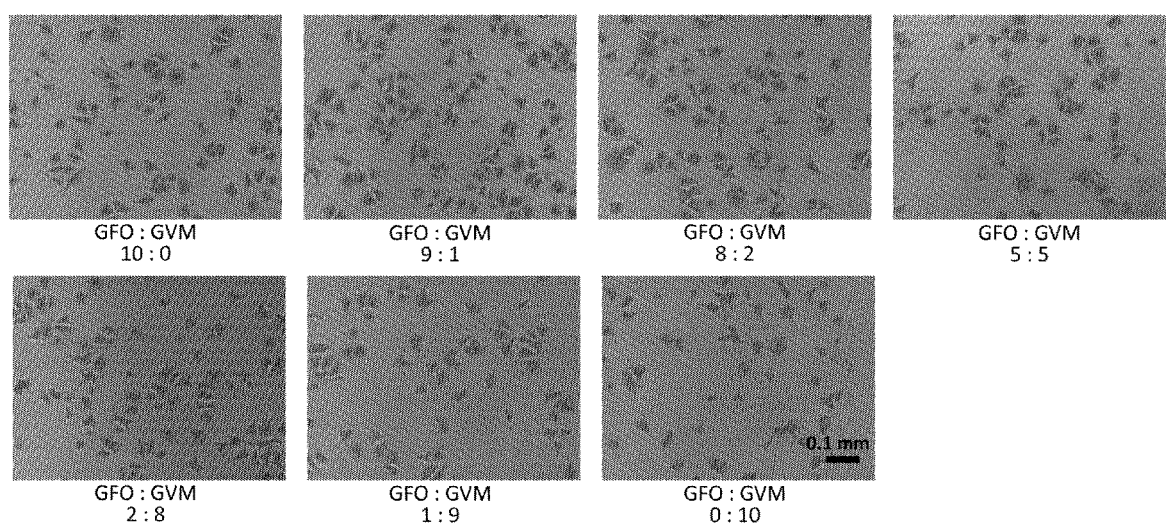
FIG. 16A is a series of microscope observation images that are presented as study results of cell adhesion in the cases of gels of polymerized peptides containing and combining multiple binding motifs which are GFOGER sequence motif (SEQ ID NO: 26) (GFO) and GVMGFO sequence motif (SEQ ID NO: 27) (GVM) at various content ratios.
Figure 16B:
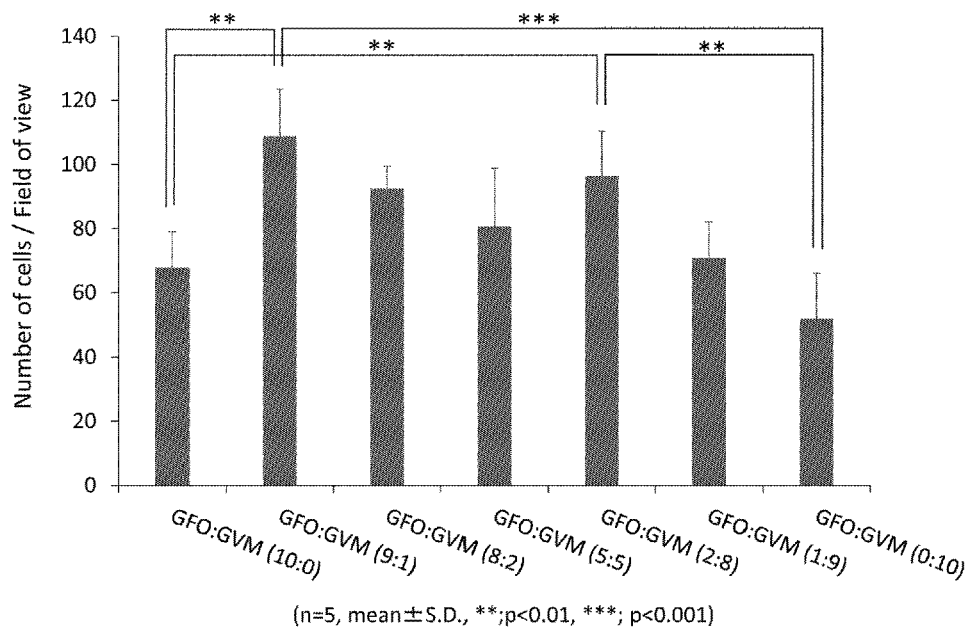
FIG. 16B shows a result obtained by calculating the number of adherent cells, the result being presented as a study result of cell adhesion in the cases of gels of the polymerized peptides containing and combining multiple binding motifs which are GFOGER sequence motif (SEQ ID NO: 26) (GFO) and GVMGFO sequence motif (SEQ ID NO: 27) (GVM).

Observation Result of Cell Adhesion with Respect to Polymerized Peptide Containing Multiple Ligands YCC2-GFOGER (SEQ ID NO: 12) and YCC2-GVMGFO (SEQ ID NO: 13) were mixed together at various ratios to be copolymerized to obtain a polymerized peptide. A 96-well plate was then coated with such polymerized peptide, followed by culturing HDF on the such plate. Here, a state of cell adhesion and a result obtained by counting the number of adherent cells are shown in FIG. 16A and FIG. 16B.

As compared to the number of adherent cells with respect to a polymerized peptide only having GFOGER (SEQ ID NO: 26) as a ligand of integrin or only having GVMGFO (SEQ ID NO: 27) as a ligand of DDR, the number of adherent cells in the case of mixing GFOGER (SEQ ID NO: 26) and GVMGFO (SEQ ID NO: 27) was observed to have a trend of increasing overall.

By employing the peptide of the present invention that has two Cys residues at each of the two termini of the peptide, there can be produced a hydrogel having, as a basic structure, the triple-helical structure typical of a collagen. Since the hydrogel forming capability of the peptide of the invention is not dependent on the amino acids in the triple helix sequence, it is possible to incorporate into the sequence forming triple helix various amino acid sequences that satisfy (Xaa-Yaa-Gly) n. Specifically, by incorporating into the sequence forming triple helix GFOGER (SEQ ID NO: 26) as a binding sequence of integrin, GVMGFO (SEQ ID NO: 27) as a binding sequence of DDR or KGHRGF (SEQ ID NO: 28) as a binding sequence of HSPG, it is possible to induce cell adhesion specific to sequence. Further, by incorporating a motif of a ligand of a particular receptor into the peptide sequence of the present invention, signal input by a target receptor becomes possible. The peptide of the present invention is superior in that by copolymerizing peptides having various sequences, ligands can be mixed in a quantitative way. The peptide of the invention and the gel thereof can be provided as a tool for controlling cells' activities such as stretching, proliferation and differentiation. Further, by processing the collagen-like peptide hydrogel produced by using the peptide of the invention into the form of a sheet, it can be used as an adhesion prevention material for organs, a suture material and a wound dressing that are required after surgery. And, by culturing appropriate cells on this sheet, there can also be produced an artificial cornea and a cell sheet such as an artificial myocardial membrane that can be transplanted into the body.

Example 7

<Production of Polymerized Peptide with RGD Motif Linked to Side Chain of Peptide Chain by Linker, and Evaluation of Cellular Adhesion>

Next, there was produced a polymerized peptide of a collagen-like peptide with a biologically active motif linked to the side chain of the peptide chain via a linker; and a gel containing it, for the purpose of evaluating the adhesion of human fibroblasts.

(1) Production of Polymerized Peptide with RGD Motif Linked to Side Chain of Peptide Chain by Linker, and a Gel Thereof CCC2-KGHRGF (SEQ ID NO: 18) was synthesized by a method similar to that of example 2. After forming triple helix with such CCC2-KGHRGF (SEQ ID NO: 18) at 1.11 mg/ml, DMSO was added to the concentration of 10%, and a mineral oil was then layered thereon, followed by oxidized and polymerized at room temperature for a week. Next, the polymerized peptide employing CCC2-KGHRGF (SEQ ID NO: 18) was diluted to 30 µg/ml, and a 96-well plate was then coated with such polymerized peptide overnight. Then, the solution was removed, followed by adding thereto 1 mg/ml BS (PEG)$_5$ (by Pierce, catalog No. 21581) dissolved in a 5 mg/ml NaHCO$_3$ aqueous solution, and then reacted at room temperature for about an hour to bind the linker. Next, there was added 10 mM ethanolamine (EA) or 100 µg/ml RGD pep (SEQ ID NO. 22) dissolved in a 5 mg/ml NaHCO$_3$ aqueous solution, followed by allowing reaction to link CCC2-KGHRGF (SEQ ID NO: 18) to the linker at room temperature for about an hour.

(2) Evaluation of Adhesion of Human Fibroblasts 5 mg/ml BSA was added to a gel linked with the above RGD motif, to perform blocking for about an hour. Next, a human fibroblast (HDF) suspension was added thereto and cultured at 37° C. for about an hour, followed by removing floating cells along with the medium, and then performing washing using PBS. Adherent cells were then fixed with 4% p-formaldehyde, followed by performing 2% crystal violet staining, and washing the sample with water, then dried in air. After air drying, microscopic observation was carried out, and there was evaluated a binding ability of HDF to the RGD motif linked to such polymerized peptide via a linker.

(3) Evaluation Result of Adhesion of Fibroblasts to Gel Bonded to RGD Motif

Figure 17:
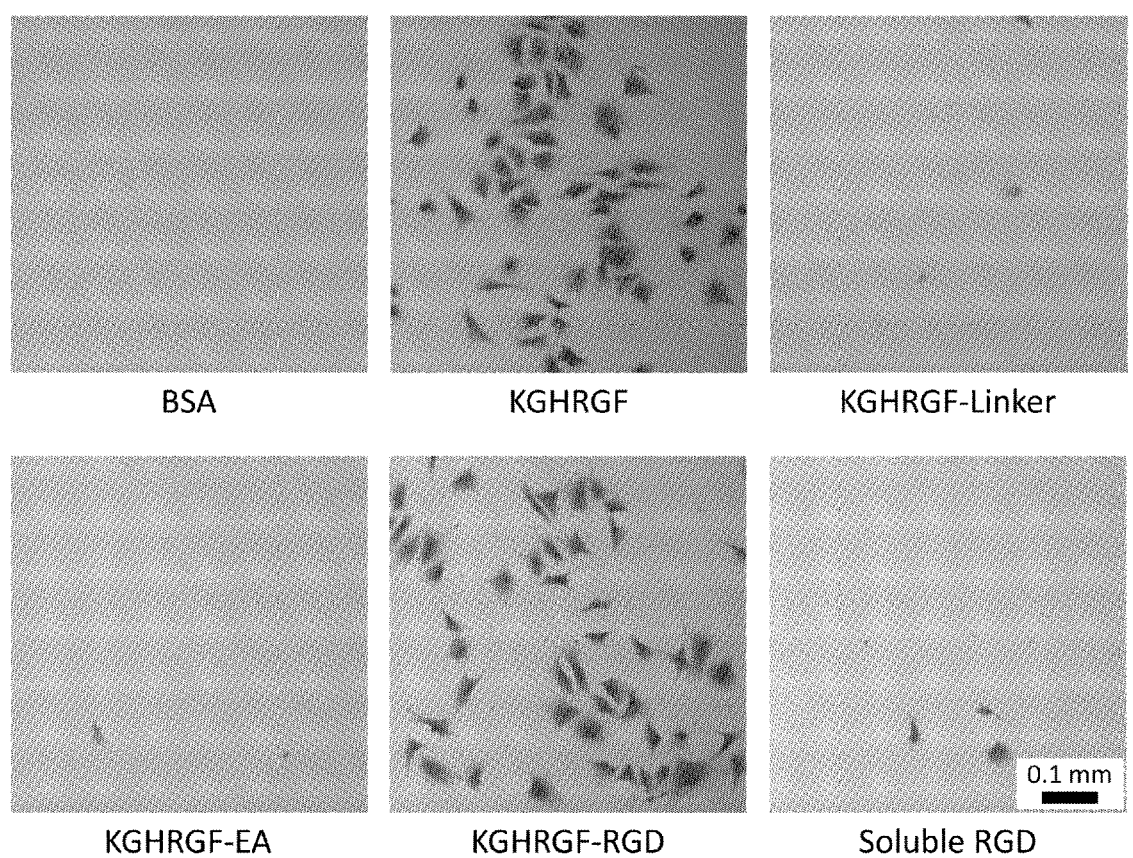
FIG. 17 is a series of microscope observation images that are presented as study results of the adhesion of human fibroblasts in the case of a gel of a polymerized peptide binding RGD motif to the side chain of a single-chain peptide via a linker.

As is the case with example 5, the adhesion of HDF was exhibited by a gel (KGHRGD (SEQ ID NO: 41)) of a polymerized peptide in which a linker was not linked to KGHRGF (SEQ ID NO: 18). In contrast, the adhesion of HDF was not exhibited by a polymerized peptide (KGHRGF-linker ("KGHRGF" disclosed as SEQ ID NO: 18)) of a peptide in which a linker was linked to KGHRGF (SEQ ID NO: 18). The adhesion of HDF was exhibited by a polymerized peptide (KGHRGF-RGD ("KGHRGF" disclosed as SEQ ID NO: 18 and "RGD" disclosed as SEQ ID NO: 22)) in which the RGD motif was further linked to this linker. Moreover, the binding ability of HDF was not exhibited (FIG. 17), when employing a soluble peptide (soluble RGD) having the RGD motif, as a control.

From the above results, it can be considered that by modifying KGHRGF (SEQ ID NO: 18), a cellular adhesion to KGHRGF (SEQ ID NO: 18) by heparan sulfate of syndecan was lost, and that by modifying the side chain of Lys with RGD, a cell adhesion activity thereto by integrin was endowed.

From the above results, it was indicated that a desired cellular adhesion could be endowed even in a polymerized peptide in which a motif was linked to the side chain of a peptide chain via a linker.

Example 8

<Cell Adhesion Assay with Polymerized Gel Combining Multiple Kinds of Functions>

There were combined a triple-chain peptide formed by peptides which were CCC2-GPOGPR (short) (SEQ ID NO: 10), CC2-GPOGPR (short) (SEQ ID NO: 23) and C2-GPOGPR (short) (SEQ ID NO: 24) as peptide chains for controlling the stiffness of a gel; and a triple-chain peptide formed by CCC2-GFOGER (short) (SEQ ID NO: 11) as a peptide chain having a biologically active motif, and a gel of a polymerized peptide was produced by oxidative cross-linking. Then, there was evaluated an effect of such gel on the cell aggregation activity of human dermal fibroblasts.

1. Evaluation of Adhesion Activity of Human Dermal Fibroblasts in Gel Mixed with GFOGER Motif (SEQ ID NO: 26) Containing CCC2-GFOGER (Short) (SEQ ID NO: 11)

In the beginning, a triple-chain peptide containing a small amount of CCC2-GFOGER (short) (SEQ ID NO: 11) having a human dermal fibroblast adhesion capability was added to a triple-chain peptide containing peptide chain CCC2-GPOGPR (short) (SEQ ID NO: 10) in order to produce a gel by cross-linking and polymerization, followed by evaluating the adhesion of human dermal fibroblasts in the gel and a cell aggregation associated with the intercellular interaction.

Experimental Methods

CCC2-GPOGPR (short) (SEQ ID NO. 10), CC2-GPOGPR (short) (SEQ ID NO. 23) or C2-GPOGPR (short) (SEQ ID NO. 24) was respectively dissolved in a degassed ultrapure water, followed by heating it at 80° C. for 5 min, and then stranded at 4° C. overnight to form triple helix. These were mixed at various ratios, and DMSO was then added thereto in a way such that a final concentration became 10%, followed by adding them into a 96-well plate by 50 µL each. At that time, a triple-chain peptide containing CCC2-GFOGER (short) (SEQ ID NO. 11) of a weight ratio 1% was added to all the peptide mixture liquids, and those to which the triple-chain peptide was not added were recited as "Ligand-free." This plate was then left to stand Mill in a container filled with 10% DMSO for four days or longer to turn the peptide solution into a gel. These gels were able to dilute DMSO by immersion in a cell culture medium overnight, and then used in the following experiments employing cells. Here, type I collagen was used as a positive control.

The human dermal fibroblasts (HDF) were stripped with 0.05% trypsin/EDTA, followed by centrifuged at 800 rpm in a 15 mL tube to collect the cells. The cells collected were then resuspended with a culture medium containing a cell staining reagent (Cell tracker green CMFDA, Life Technologies Japan Ltd.), followed by incubating them at 37° C. for 20 to 30 min, and then provided to the assay. HDFs ($10 \times 10^3$ cells/well) resuspended in D-MEM (1% FBS, penicillin, streptomycin) were seeded into the gel prepared in the 96-well plate, followed by culturing them at 37° C. for three hours. These were then observed by a confocal microscope.

Experimental Results

Figure 18A:
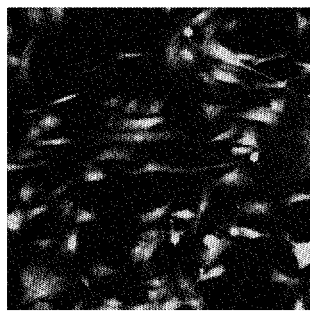
FIG. 18A is a series of photographs showing a result of cell adhesion assay employing a multifunctional gel prepared by mixing thereinto two kinds of peptides with different properties which are a peptide chain CCC2-GPOGPR (short) (SEQ ID NO: 10) for controlling the stiffness (stiffness) of the gel and a peptide chain CCC2-GFOGER (short) (SEQ ID NO: 11) having a biologically active motif. A fluorescence microscope was used to observe the adhesion and aggregation of human dermal fibroblasts to the gel, with type I collagen being a positive control, and a polymerized gel containing no CCC2-GFOGER (short) (SEQ ID NO: 11) being a negative control.
Figure 18A:
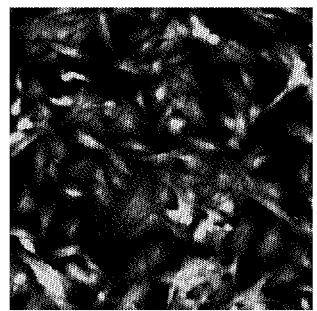
Figure 18A:
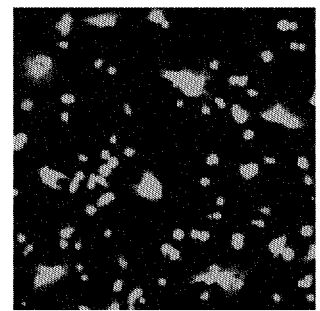

FIG. 18A shows results obtained by comparing the adhesion to human dermal fibroblasts in the case of a polymerized peptide-containing gel produced by gel formation after mixing a collagen with the triple-chain peptide of CCC2-GFOGER (short) (SEQ ID NO: 11) of a weight ratio 1%; the adhesion to human dermal fibroblasts in the case of a polymerized peptide-containing gel produced by gel formation after mixing the gel (ligand free) prepared by cross-linking and polymerizing only the triple-chain peptide of CCC2-GPOGPR (short) (SEQ ID NO: 10) with the triple-chain peptide of CCC2-GFOGER (short) (SEQ ID NO: 11) of a weight ratio 1%; and the adhesion to human dermal fibroblasts in the case of a polymerized peptide-containing gel produced by gel formation after mixing the triple-chain peptide of CCC2-GPOGPR (short) (SEQ ID NO: 10) with the triple-chain peptide of CCC2-GFOGER (short) (SEQ ID NO: 11) of a weight ratio 1%.

In the case of the gel containing the triple-chain containing the collagen and CCC2-GFOGER (short) (SEQ ID NO: 11), there was confirmed an observation image where each human dermal fibroblast elongated and adhered respectively. However, in the case of the gel (ligand free) produced by oxidatively cross-linking only the triple-chain peptide of CCC2-GPOGPR (short) (SEQ ID NO: 10), there was only observed a fractional level of cell adhesion (FIG. 18A).

2. Evaluation of Cell Aggregation Activity of Human Dermal Fibroblasts in Polymerized Gel Produced by Combining Triple-Chains Containing Peptide Chains with Different Numbers of Cysteine Residues Next, peptide chains with different numbers of cysteine residues were employed, and then using gels of various composition ratios that are made of triple-chain peptides containing these peptide chains, compared and evaluated were a gel-forming capability and cell adhesion capability with regard to gels containing the triple-chain peptide of CCC2-GFOGER (short) (SEQ ID NO: 11) of the weight ratio 1%.

Experimental Results

Two different triple-chain peptides among triple-chain peptides each containing CCC2-GPOGPR (short) (SEQ ID NO: 10), CC2-GPOGPR (short) (SEQ ID NO: 23) and C2-GPOGPR (short) (SEQ ID NO: 24) were combined together at a composition ratio of 9:1, 7:3, 5:5, 3:7 or 1:9, and mixed in a solvent. Further, as is the case with the above experiment, the triple-chain peptide containing CCC2-GFOGER (SEQ ID NO: 16) of the weight ratio of 1% was added, followed by producing gels prepared by polymerizing the triple-chain peptides by oxidative cross-linking, and then using a method similar to that of the above experiments to evaluate the cell aggregation of human dermal fibroblasts adhering to these gels.

Experimental Results

With regard to gels whose composition ratios of CC2-GPOGPR (short) (SEQ ID NO: 23): C2-GPOGPR (short) (SEQ ID NO: 24) are 7:3, 5:5, 3:7 and 1:9, and gels whose composition ratios of CCC2 (short) (SEQ ID NO: 5): C2-GPOGPR (short) (SEQ ID NO: 24) are 3:7 and 1:9, gel formation did not cause even after adding DMSO as an oxidative cross-linking agent.

Figure 18B:
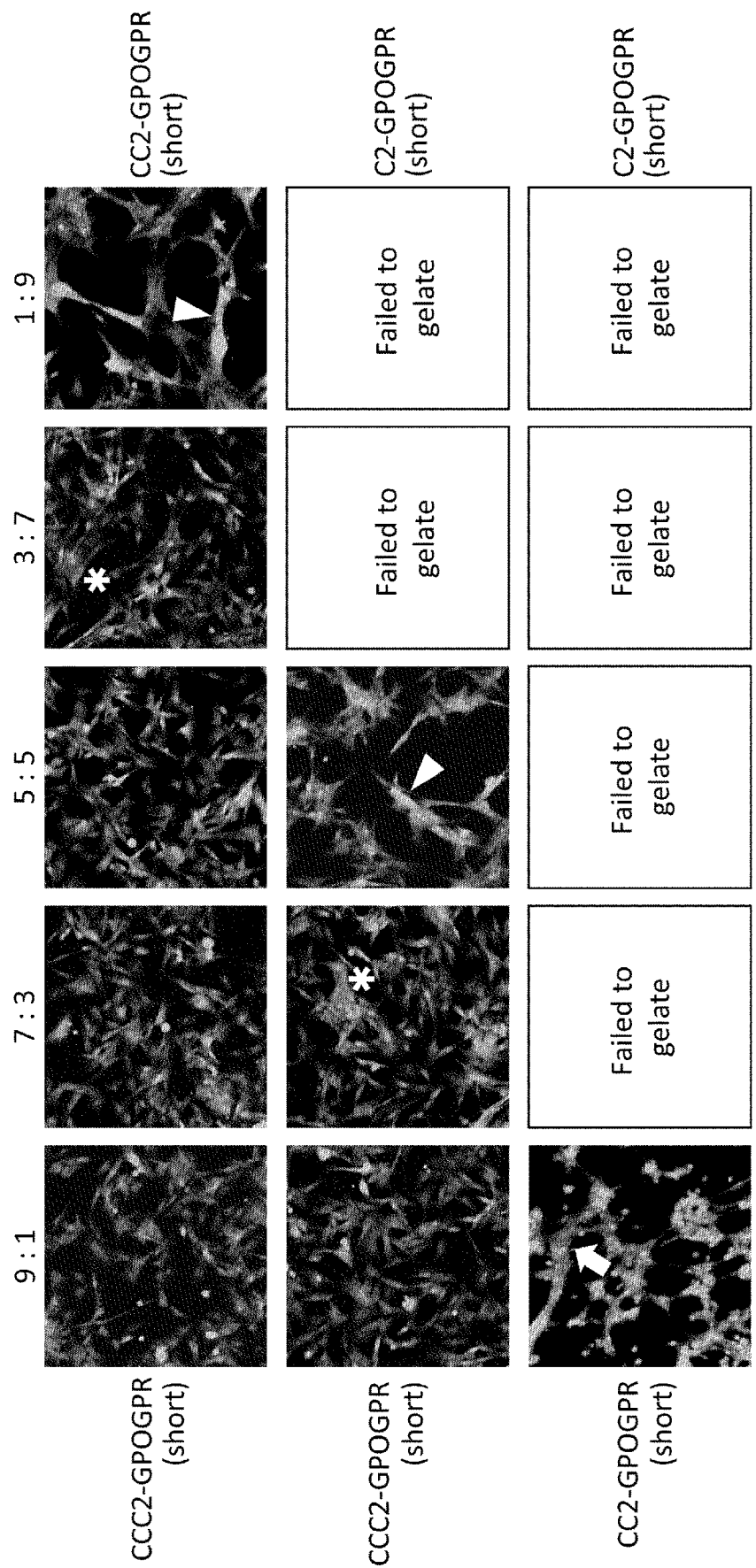
FIG. 18B is a series of photographs showing a result of cell adhesion assay employing a multifunctional gel prepared by mixing thereinto two kinds of peptides with different properties which are the peptide chain for controlling the stiffness of the gel and the peptide chain having a biologically active motif. Prepared were gels with the two components combined together at various composition ratios which were 9:1, 7:3, 5:5, 3:7 and 1:9, and the cell aggregation of the human dermal fibroblasts adhering to such gels was evaluated.

Meanwhile, as for the composition ratios of peptide chains with which a gel-forming capability was observed, there were confirmed (1) an observation image (arrow in FIG. 18B) showing a formation of an aggregate exhibiting a strong intercellular adhesion, and that the individual cells seemed to cause no progression, (2) an observation image (* in FIG. 18B) where several cells adhered while being aggregated, (3) an observation image (Δ in FIG. 18B) where aggregations containing several cells aggregated even more, and (4) an observation image where most of the cells respectively elongated and adhered (FIG. 18B, observation images of CCC2-GPOGPR (short) (SEQ ID NO: 10): CC2-GPOGPR (short) (SEQ ID NO: 23)=9:1, 7:3, 5:5, and CCC2-GPOGPR (short) (SEQ ID NO: 10): C2-GPOGPR (short) (SEQ ID NO: 24)=9:1).

From these results, it was found that as the composition ratio of CC2-GPOGPR (short) (SEQ ID NO: 23) or C2-GPOGPR (short) (SEQ ID NO: 24) to CCC2-GPOGPR (short) (SEQ ID NO: 10) increased, the interactions between the cells became stronger in a way such that the individual cells did not, but exhibit a morphological aspect of cell where the cells gathered together and aggregated (FIG. 18B, marked "*"). Further, the aggregation of the cells were observed in a more significant manner in the case of gels prepared by mixing CC2-GPOGPR (short) (SEQ ID NO: 23) and C2-GPOGPR (short) (SEQ ID NO: 24).

That is, when employing peptide chains with small numbers of cysteine residues, the gel-forming capability would decrease, and the cell adhesion capability was improved. In contrast, there was observed a tendency that when employing peptide chains with large numbers of cysteine residues, gel formation became easy, and the individual cells strongly adhered to the gels and elongated.

These changes in the activities of the cells indicated that by producing a gel by mixing peptides with different numbers of cysteines, it became possible to control the tolerability (stiffness) of such gel, control the bioactivity expressions of such gel, and improve the biocompatibilities of such gel.

Example 9

<In Vivo Implantation Experiment>

A gel prepared by rehydrating a gel thin membrane was transplanted into a living body, and the changes of such gel in vivo were studied and evaluated.

1. Production and Rehydration of Gel Thin Membrane

A triple-chain peptide containing CCC2-GPOGPR (short) (SEQ ID NO. 10) and a triple-chain peptide containing soluble GPOGPR (short) (SEQ ID NO. 25) were mixed together at a ratio of 1:1, followed by using DMSO to oxidatively cross-linking them to produce a gel containing a polymerized peptide. This gel was dried, and then stored at room temperature for a week or longer. The gel was then rehydrated with saline immediately before use. At that time, a PVDF (polyvinylidene fluoride) membrane free from biodegradation was produced as a supporting material used as a marker for a transplantation position, the membrane was then used in the following in vivo implantation experiment.

2. In Vivo Implantation Experiments

A collagen-like polymerized peptide thin membrane was transplanted into the dorsal subcutaneous region of C57BL6 mice (male, 8 weeks old). In the implantation experiment, under inhalant anesthesia by isoflurane, the dorsal regions of the mice were dehaired, and a skin incision of a size of about 2 cm was then made thereon. A pair of mosquito forceps was inserted through the incision to create a subcutaneous pocket, followed by inserting the collagen-like polymerized peptide thin membrane into this subcutaneous pocket to complete the implantation operation, and then using a nylon thread for suture and closure.

The mice were sacrificed 10 days after the transplantation, and 30 days after the transplantation, followed by removing their tissues, fixed with 10% formalin solution, preparing a paraffin section, stained with hematoxylin-eosin, and then histologically investigated by optical microscopy.

Figure 19A:
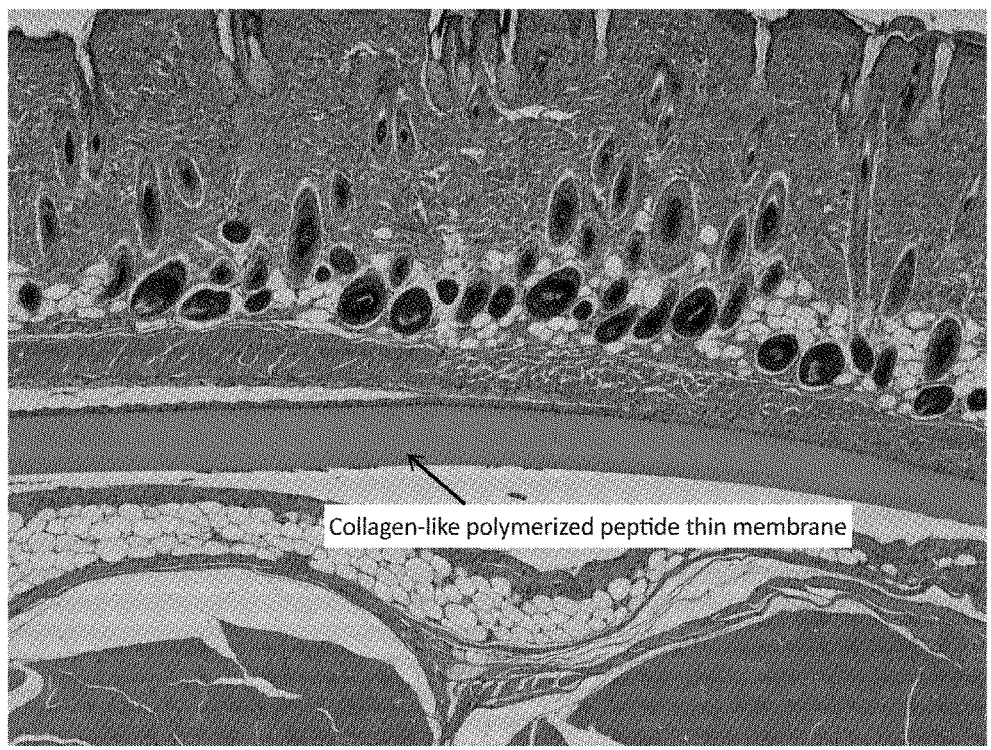
FIG. 19A shows a result obtained by evaluating the biodegradability of a collagen-like polymerized peptide thin membrane in vivo after transplantation. Presented is a microscope photograph showing a dorsal subcutaneous tissue observed 10 days after implanting the collagen-like polymerized peptide thin membrane into the dorsal subcutaneous region of a mouse, the dorsal subcutaneous tissue was stained with hematoxylin-eosin.
Figure 19B:
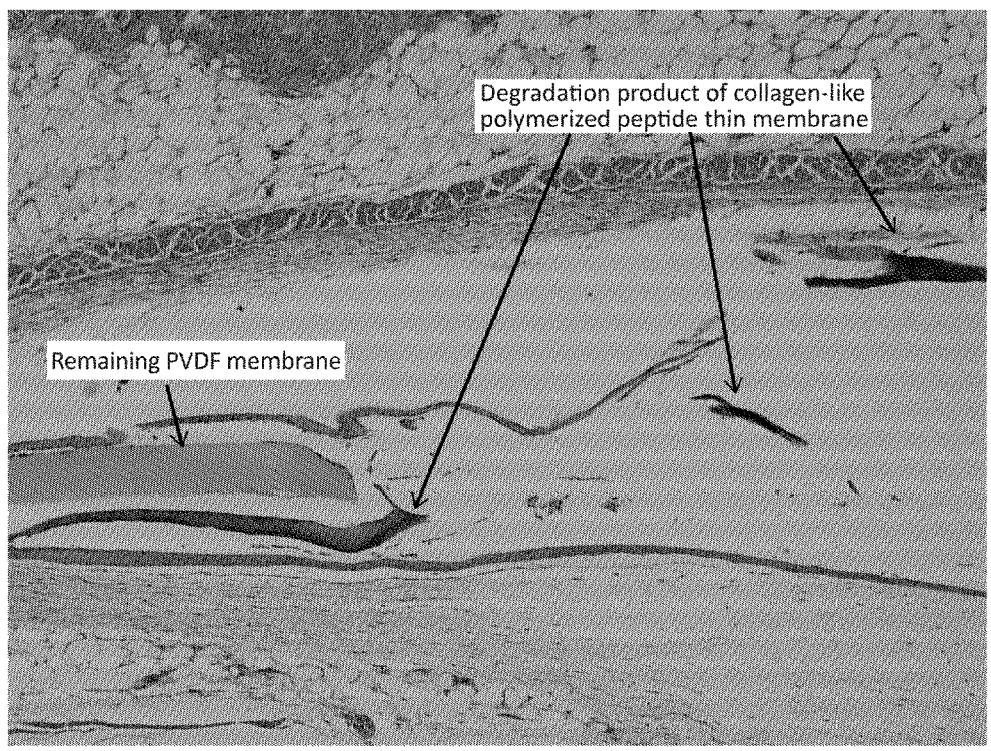
FIG. 19B is a microscopic photograph showing a dorsal subcutaneous tissue observed 30 days after implanting the collagen-like polymerized peptide thin membrane into the dorsal subcutaneous region of a mouse, the dorsal subcutaneous tissue was stained with hematoxylin-eosin. PVDF was used as a supporting material for confirming the transplantation site due to the fact that it does not cause biodegradability.

As a result, adhesion of fibroblasts was observed on the surface of the thin membrane (FIG. 19A) 10 days after the transplantation; the collagen-like polymerized peptide thin membrane was degraded and absorbed, and the thinning of the membrane thickness was observed, 30 days after the transplantation (FIG. 19B). At this point of time, inflammatory cell infiltration in the subcutaneous regeneration area was minimal, foreign body giant cell infiltration was not observed therein, and the level of fibrosis was similar to that in the case of a natural collagen. Meanwhile, a foreign-body reaction involving foreign body giant cell infiltration was partially observed on the periphery of the PVDF membrane as the supporting material. In this way, the biological compatibility of the collagen-like polymerized peptide was confirmed.

From these results, it was indicated that by leaving the gel or polymerized peptide thin membrane that contains the polymerized peptide of the invention between organs and skin or between organs and organs at the time of surgery, the gel or thin membrane could be used as a medical material such as a material for organ adhesion prevention, a suture material, a dressing material for region of wound and a material for promoting wound healing. The medical material of the invention thus placed gradually become soluble and degraded, and then disappear, due to peptidase and phagocytes such as macrophage that are present in vivo. Therefore, no further surgery is required to remove such medical material, thus resulting in advantages of imposing a smaller burden on the prognosis of a patient, and thereby improving QOL (Quality of life).

Further, since the medical material of the present invention is an artificially produced collagen-like peptide, it differs from natural collagens in that it carries a low risk of viral infection and microbial infection. Furthermore, since the medical material of the invention is cross-linked by the disulfide bond, the material does not denature even after being subjected to a heating treatment. That is, the medical material of the invention has an advantage that sterilization can be performed by heating.

---

The invention claimed is:

1. A gelling agent comprising at least one kind of a polymerized peptide that has, as a polymerization unit, a triple-chain peptide having a triple-helical structure, and is polymerized by oxidative cross-linking, wherein peptide chains composing the triple-chain peptide are identical to or different from one another, and each peptide chain has:
one or more triple helix forming peptidyl groups each having a repeating structure in which -(Xaa-Yaa-Gly)- as a basic unit is repeated at least 5 times; and one or more cross-link forming peptidyl groups each comprising at least two cysteine (Cys) residues within 6 residues from each of an amino-terminus and a carboxy-terminus, and wherein each of Xaa and Yaa is independently selected from a proline (Pro or P) residue, a hydroxyproline (Hyp or O) residue, an arginine (Arg or R) residue, a lysine (Lys or K) residue, a valine (Val or V) residue, a leucine (Leu or L) residue, an isoleucine (Ile or I) residue, a serine (Ser or S) residue, a threonine (Thr or T) residue, an alanine (Ala or A) residue, a glycine (Gly or G) residue, an N-isobutyl glycine residue, a phenylalanine (Phe or F) residue, a methionine (Met or M) residue, a glutamate (Glu or E) residue, an aspartate (Asp or D) residue, an asparagine (Asn or N) residue, a glutamine (Gln or Q) residue, a histidine (His or H) residue, a tryptophan (Trp or W) residue or a tyrosine (Tyr or Y) residue, the proline residue may be modified by an amino group or fluorine atom.

2. The gelling agent according to claim 1, comprising at least one kind of the polymerized peptide polymerized with the peptide chains selected from the group consisting of the following (i) to (iii):
   (i) a peptide chain comprising at least one of the triple helix forming peptidyl group (s) and at least one of the cross-link forming peptidyl group(s);
   (ii) a peptide chain comprising at least one of the triple helix forming peptidyl group(s), at least one of the cross-link forming peptidyl group(s) and at least one peptidyl group(s) having a motif having a bioactivity; and
   (iii) a peptide chain comprising at least one of the triple helix forming peptidyl group (s), at least one of the cross-link forming peptidyl group(s), and at least one peptidyl group(s) having an amino acid residue linking a biologically active motif to a side chain thereof via a linker.

3. The gelling agent according to claim 2, comprising at least one kind of a copolymerized peptide produced by combining not less than two kinds of the biologically active motifs.

4. A method for producing the gelling agent as set forth in claim 1, comprising:
   dissolving into a solvent identical or different peptide chains each having a repeating structure in which (Xaa-Yaa-Gly) as a basic unit is repeated at least 5 times, comprising at least two cysteine (Cys) residues within 6 residues from each of an amino-terminus and a carboxy-terminus;

forming a triple-chain peptide having a triple-helical structure comprised of three of the peptides, by self-assembly; and performing polymerization by oxidative cross-linking with the triple-chain peptide being a polymerization unit, wherein each of Xaa and Yaa is independently selected from a pro line (Pro or P) residue, a hydroxyproline (Hyp or O) residue, an arginine (Arg or R) residue, a lysine (Lys or K) residue, a valine (Val or V) residue, a leucine (Leu or L) residue, an isoleucine (lie or I) residue, a serine (Ser or S) residue, a threonine (Thr or T) residue, an alanine (Ala or A) residue, a glycine (Gly or G) residue, an N-isobuty glycine residue, a phenylalanine (Phe or F) residue, a methionine (Met or M) residue, a glutamate (Glu or E) residue, an aspartate (Asp or D) residue, an asparagine (Asn or N) residue, a glutamine (Gin or Q) residue, a histidine (His or H) residue, a tryptophan (Trp or W) residue or a tyrosine (Tyr or Y) residue, the proline residue may be modified by an amino group or fluorine atom.

5. A gel comprising at least one kind of the gelling agents as set forth in claim 1.

6. The gel according to claim 5, comprising a gelling agent prepared by combining at least two kinds of triple-chain peptides with the triple-chain peptide as set forth in claim 1 being a polymerization unit.

7. The gel according to claim 5, further comprising at least one kind of a triple-chain peptide comprising no cysteine residue.

8. The gel according to claim 5, wherein the gel is a hydrogel used as a base material for culturing selected cells.

9. A polymerized peptide thin membrane produced by drying the gel as set forth in claim 5.

10. A regenerative medical material comprising the gel as set forth in claim 5 or the polymerized peptide thin membrane as set forth in claim 9.

11. The regenerative medical material according to claim 10, wherein the regenerative medical material is a composition for promoting wound healing.

* * * * *

UNITED STATES PATENT AND TRADEMARK OFFICE
CERTIFICATE OF CORRECTION

PATENT NO. : 10,851,152 B2
APPLICATION NO. : 15/579286
DATED : December 1, 2020
INVENTOR(S) : Takaki Koide et al.

Page 1 of 1

It is certified that error appears in the above-identified patent and that said Letters Patent is hereby corrected as shown below:

In the Claims

Column 92, Claim 4, Lines 13 and 14 replace "isoleucine (lie or I)" with -- isoleucine (Ile or I) --

Column 92, Claim 4, Lines 16 and 17 replace "N-isobuty glycine residue" with -- N-isobutyl glycine residue --

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*